(12) United States Patent
Abate et al.

(10) Patent No.: US 9,487,581 B2
(45) Date of Patent: Nov. 8, 2016

(54) ANTI-CTLA-4 ANTIBODY COMPOSITIONS

(75) Inventors: Justin Abate, Chesterfield, MO (US); Kevin Muthurania, Chesterfield, MO (US); Sandeep Nema, Chesterfield, MO (US); Satish Singh, Chesterfield, MO (US); Carrie Elliott, Seattle, WA (US); Tapan Das, Chesterfield, MO (US)

(73) Assignee: Pfizer Inc., New York, NY (US)

( * ) Notice: Subject to any disclaimer, the term of this patent is extended or adjusted under 35 U.S.C. 154(b) by 1866 days.

(21) Appl. No.: 11/817,894

(22) PCT Filed: Mar. 2, 2006

(86) PCT No.: PCT/US2006/007555
§ 371 (c)(1),
(2), (4) Date: Apr. 18, 2008

(87) PCT Pub. No.: WO2006/096491
PCT Pub. Date: Sep. 14, 2006

(65) Prior Publication Data
US 2009/0130119 A1    May 21, 2009

Related U.S. Application Data

(60) Provisional application No. 60/659,766, filed on Mar. 8, 2005, provisional application No. 60/728,165, filed on Oct. 19, 2005, provisional application No. 60/752,712, filed on Dec. 20, 2005, provisional application No. 60/762,456, filed on Jan. 26, 2006.

(51) Int. Cl.
*A61K 39/395* (2006.01)
*C07K 16/24* (2006.01)
*A61K 39/00* (2006.01)

(52) U.S. Cl.
CPC ......... *C07K 16/243* (2013.01); *A61K 39/3955* (2013.01); *A61K 39/39591* (2013.01); *A61K 2039/505* (2013.01); *C07K 2317/21* (2013.01)

(58) Field of Classification Search
None
See application file for complete search history.

(56) References Cited

U.S. PATENT DOCUMENTS

| 4,597,966 | A | 7/1986 | Zolton et al. |
|---|---|---|---|
| 5,654,403 | A | 8/1997 | Smith et al. |
| 5,792,838 | A | 8/1998 | Smith et al. |
| 5,804,557 | A | 9/1998 | Cleland et al. |
| 6,171,586 | B1 | 1/2001 | Lam et al. |
| 6,267,958 | B1 | 7/2001 | Andya et al. |
| 6,682,736 | B1 | 1/2004 | Hanson et al. |
| 2003/0118583 | A1 | 6/2003 | Emery et al. |
| 2003/0138417 | A1 | 7/2003 | Kaisheva et al. |
| 2003/0190316 | A1 | 10/2003 | Kakuta et al. |
| 2004/0038878 | A1 | 2/2004 | Tanikawa et al. |
| 2004/0057951 | A1 | 3/2004 | Bednar et al. |
| 2005/0214278 | A1 | 9/2005 | Kakuta et al. |
| 2006/0008415 | A1* | 1/2006 | Kaisheva et al. ............ 424/1.49 |
| 2006/0088523 | A1* | 4/2006 | Andya et al. .............. 424/133.1 |
| 2006/0182740 | A1 | 8/2006 | Yang et al. |
| 2007/0048332 | A1* | 3/2007 | Oliver et al. .............. 424/204.1 |
| 2008/0248047 | A1* | 10/2008 | Das et al. ................. 424/142.1 |
| 2008/0292639 | A1* | 11/2008 | Shen et al. ................ 424/158.1 |
| 2009/0110681 | A1* | 4/2009 | Carroll .............. A61K 39/3955 424/139.1 |
| 2009/0117103 | A1* | 5/2009 | Devalaraja et al. ....... 424/133.1 |
| 2010/0119517 | A1* | 5/2010 | Burgess .................... 424/141.1 |

FOREIGN PATENT DOCUMENTS

| AR | P 06 01 00793 | 3/2006 |
|---|---|---|
| AR | P 06 01 00794 | 3/2006 |
| AR | P 06 01 00796 | 3/2006 |
| CA | 2600608 | 9/2006 |
| EP | 0612251 B1 | 12/1997 |
| EP | 1262193 | 12/2002 |
| JP | 2002-537226 | 11/2002 |
| JP | 2006-249085 | 9/2006 |
| KR | 10-2004-0085185 | 10/2004 |
| RU | 1438240 C | 3/1996 |
| WO | WO 97/45140 | 12/1997 |
| WO | WO 00/37504 | 6/2000 |
| WO | WO01/14424 A2 | 3/2001 |
| WO | WO03/039485 A2 | 5/2003 |
| WO | WO2004/007520 A2 | 1/2004 |
| WO | WO2004/091658 | 10/2004 |
| WO | WO2006/044908 | 4/2006 |
| WO | WO 2006/096461 | 9/2006 |
| WO | WO 2006/096488 | 9/2006 |
| WO | WO 2006/096490 | 9/2006 |

OTHER PUBLICATIONS

Rudikoff et al., Proc Natl Acad Sci USA 79: 1979-1983, 1982.*
Kussie et al., J. Immunol. 152: 146-152, 1994.*
Chen et al., EMBO J., 14: 2784-2794, 1995.*
Colman, Research in Immunology 145: 33-36, 1994.*
Hodi,F., et al., "Biologic Activity of Cytotoxic T Lymphocyte-Associated Antigen 4 Antibody Blockade in Previously Vaccina . . . "PNAS, Apr. 15, 2003, 4712-4717, vol. 100, No. 8.
Pistillo, M., et al, :Molecular Characterization and Applications of Recombinant scFv Antibodies to CD152 Co-Stimulatory Molecu . . . Tissue Antigens, Mar. 2000, 229-238, vol. 55.
Daugherty, Al, et al, "Formulation and Delivery Issues for Monoclonal Antibody Therapeutics," Advanced Drug Delivery Reviews, 2006, 686-706, 58.
Chen, B., et al, "Influence of Histidine on the Stability and Physical Properties of a Fully Human . . . " Pharmaceutical Research, Dec. 2003, 1952-1960, vol. 20, No. 12.
Wang, "Instability, stabilization, and formulation of liquid protein pharmaceuticals," *International Journal of Pharmaceutics* 185 (2):129-188 (1999).

(Continued)

*Primary Examiner* — Phillip Gambel
(74) *Attorney, Agent, or Firm* — Ropes & Gray LLP

(57) ABSTRACT

The present invention provides for novel compositions of anti-CTLA-4 antibodies comprising a chelating agent. Also provided are method of treating diseases and conditions with novel compositions of CTLA-4 antibodies, including various neoplasia conditions.

20 Claims, 12 Drawing Sheets

(56) References Cited

OTHER PUBLICATIONS

Camacho et al., "Novel therapies targeting the immune system: CTLA4 blockade with tremelimumab (CP-675,206), a fully human monoclonal antibody," Expert Opin. Investig. Drugs 17(3):371-385 (2008).

Canniff et al., "CP-675,205 anti-CTLA4 antibody clinical candidate enhances IL-2 production in cancer patient T cells in vitro regardless of tumor type or stage of disease," Proc Am Assoc Cancer Res 45:Abstract 709 (2004).

Cranmer et al., "The Role of the CTLA4 Blockade in the Treatment of Malignant Melanoma," Cancer Investigation 25:613-631 (2007).

Hamilton et al., "Human IgG Subclass Measurements in the Clinical Laboratory," Clin. Chem. 33(10):1707-1725 (1987).

O'Day et al., "Targeting Cytotoxic T-Lymphocyte Antigen-4 (CTLA-4): A Novel Strategy for the Treatment of Melanoma and Other Malignancies," Cancer 110(12):2614-2627 (2007).

Perchiacca et al., "Engineering Aggregation-Resistant Antibodies," Annu. Rev. Chem. Biomol. Eng. 3:263-286 (2012).

Frokjaer and Hovgaard, *"Pharmaceutical Formulation Development of Peptides and Proteins,"* Taylor & Francis Limited (2000).

Tsai et al., "Formulation design of acidic fibroblast growth factor," *Pharm Research* 10(5): 649-659 (1993).

Ruiz et al., "Long-term stabilization of recombinant human interferon alpha 2b in aqueous solution without serum albumin," *Int. Journal of Pharmaceutics* 264:57-72 (2003).

Wang et al., "Antibody structure, instability, and formulation," *J Pharm Sci.* 96(1):1-26 (2007).

\* cited by examiner

FIG. 11A

Ticilimumab (11.2.1) Heavy Chain DNA (SEQ ID NO: 1)

| | | | | | |
|---|---|---|---|---|---|
| atggagtttg | ggctgagctg | ggtttcctc | gttgctcttt | taagaggtgt | ccagtgtcag | 60 |
| gtgcagctgg | tggagtctgg | gggaggcgtg | gtccagcctg | ggaggtccct | gagactctcc | 120 |
| tgtgcagcgt | ctggattcac | cttcagtagc | tatggcatgc | actgggtccg | ccaggctcca | 180 |
| ggcaagggc | tggagtgggt | ggcagttata | tggtatgatg | aagtaataa | atactatgca | 240 |
| gactccgtga | agggccgatt | caccatctcc | agagacaatt | ccaagaacac | gctgtatctg | 300 |
| caaatgaaca | gcctgagagc | cgaggacacg | gctgtgtatt | actgtgcgag | agatccgagg | 360 |
| ggagctaccc | tttactacta | ctactacggt | atggacgtct | ggggccaagg | gaccacggtc | 420 |
| accgtctcct | cagcctccac | caagggccca | tcggtcttcc | cctggcgcc | ctgctccagg | 480 |
| agcacctccg | agagcacagc | ggccctgggc | tgcctggtca | aggactactt | ccccgaaccg | 540 |
| gtgacggtgt | cgtggaactc | aggcgctctg | accagcggcg | tgcacacctt | cccagctgtc | 600 |
| ctacagtcct | caggactcta | ctccctcagc | agcgtggtga | ccgtgccctc | cagcaacttc | 660 |
| ggcacccaga | cctacacctg | caacgtagat | cacaagccca | gcaacaccaa | ggtggacaag | 720 |
| acagttgagc | gcaaatgttg | tgtcgagtgc | ccaccgtgcc | cagcaccacc | tgtggcagga | 780 |
| ccgtcagtct | tcctcttccc | cccaaaaccc | aaggacaccc | tcatgatctc | ccggaccct | 840 |
| gaggtcacgt | gcgtggtggt | ggacgtgagc | cacgaagacc | ccgaggtcca | gttcaactgg | 900 |
| tacgtggacg | gcgtggaggt | gcataatgcc | aagacaaagc | cacgggagga | gcagttcaac | 960 |
| agcacgttcc | gtgtggtcag | cgtcctcacc | gttgtgcacc | aggactggct | gaacggcaag | 1020 |
| gagtacaagt | gcaaggtctc | caacaaaggc | ctcccagccc | ccatcgagaa | aaccatctcc | 1080 |
| aaaaccaaag | ggcagccccg | agaaccacag | gtgtacaccc | tgcccccatc | ccgggaggag | 1140 |
| atgaccaaga | accaggtcag | cctgacctgc | ctggtcaaag | gcttctaccc | cagcgacatc | 1200 |
| gccgtggagt | gggagagcaa | tgggcagccg | gagaacaact | acaagaccac | acctcccatg | 1260 |
| ctggactccg | acggctcctt | cttcctctac | agcaagctca | ccgtggacaa | gagcaggtgg | 1320 |
| cagcagggga | acgtcttctc | atgctccgtg | atgcatgagg | ctctgcacaa | ccactacacg | 1380 |
| cagaagagcc | tctccctgtc | tccgggtaaa | tga | | | 1413 |

FIG. 11B

Ticilimumab (11.2.1) Heavy Chain Protein (SEQ ID NO: 2)

```
[QVQLVESGGG VVQPGRSLRL SCAASGFTFS SYGMHWVRQA PGKGLEWVAV IWYDGSNKYY    60
ADSVKGRFTI SRDNSKNTLY LQMNSLRAED TAVYYCARDP RGATLYYYYY GMDVWGQGTT   120
VTVSS]ASTKG PSVFPLAPCS RSTSESTAAL GCLVKDYFPE PVTVSWNSGA LTSGVHTFPA   180
VLQSSGLYSL SSVVTVPSSN FGTQTYTCNV DHKPSNTKVD KTVERKCCVE CPPCPAPPVA   240
GPSVFLFPPK PKDTLMISRT PEVTCVVVDV SHEDPEVQFN WYVDGVEVHN AKTKPREEQF   300
NSTFRVVSVL TVVHQDWLNG KEYKCKVSNK GLPAPIEKTI SKTKGQPREP QVYTLPPSRE   360
EMTKNQVSLT CLVKGFYPSD IAVEWESNGQ PENNYKTTPP MLDSDGSFFL YSKLTVDKSR   420
WQQGNVFSCS VMHEALHNHY TQKSLSLSPG K                                  451
```

The variable region (SEQ ID NO:5) is depicted [between brackets] and the CDRs are underlined. CDR1 is indicated by SEQ ID NO:7, CDR2 by SEQ ID NO:8, and CDR3 by SEQ ID NO:9.

SEQUENCE LISTING

<160> NUMBER OF SEQ ID NOS: 18

<210> SEQ ID NO 1
<211> LENGTH: 1413
<212> TYPE: DNA
<213> ORGANISM: Homo sapiens

<400> SEQUENCE: 1

```
atggagtttg gctgagctg ggttttcctc gttgctcttt taagaggtgt ccagtgtcag    60
gtgcagctgg tggagtctgg gggaggcgtg gtccagcctg gaggtccct gagactctcc   120
tgtgcagcgt ctggattcac cttcagtagc tatggcatgc actgggtccg ccaggctcca   180
ggcaaggggc tggagtgggt ggcagttata tggtatgatg aagtaataa atactatgca   240
gactccgtga agggccgatt caccatctcc agagacaatt ccaagaacac gctgtatctg   300
caaatgaaca gcctgagagc cgaggacacg gctgtgtatt actgtgcgag agatccgagg   360
ggagctaccc tttactacta ctactacggt atggacgtct ggggccaagg gaccacggtc   420
accgtctcct cagcctccac caagggccca tcggtcttcc ccctggcgcc ctgctccagg   480
agcacctccg agagcacagc ggccctgggc tgcctggtca aggactactt ccccgaaccg   540
gtgacggtgt cgtggaactc aggcgctctg accagcggcg tgcacacctt cccagctgtc   600
ctacagtcct caggactcta ctccctcagc agcgtggtga ccgtgccctc agcaacttc    660
ggcacccaga cctacacctg caacgtagat cacaagccca gcaacaccaa ggtggacaag   720
acagttgagc gcaaatgttg tgtcgagtgc ccaccgtgcc cagcaccacc tgtggcagga   780
ccgtcagtct tcctcttccc cccaaaaccc aaggacaccc tcatgatctc ccggacccct   840
gaggtcacgt gcgtggtggt ggacgtgagc cacgaagacc ccgaggtcca gttcaactgg   900
tacgtggacg gcgtggaggt gcataatgcc aagacaaagc cacgggagga gcagttcaac   960
agcacgttcc gtgtggtcag cgtcctcacc gttgtgcacc aggactggct gaacggcaag  1020
gagtacaagt gcaaggtctc caacaaaggc ctcccagccc ccatcgagaa aaccatctcc  1080
aaaaccaaag ggcagccccg agaaccacag gtgtacaccc tgcccccatc ccgggaggag  1140
atgaccaaga accaggtcag cctgacctgc ctggtcaaag gcttctaccc cagcgacatc  1200
gccgtggagt gggagagcaa tgggcagccg gagaacaact acaagaccac acctcccatg  1260
ctggactccg acggctcctt cttcctctac agcaagctca ccgtggacaa gagcaggtgg  1320
cagcagggga acgtcttctc atgctccgtg atgcatgagg ctctgcacaa ccactacacg  1380
cagaagagcc tctccctgtc tccgggtaaa tga                               1413
```

<210> SEQ ID NO 2
<211> LENGTH: 451
<212> TYPE: PRT
<213> ORGANISM: Homo sapiens

<400> SEQUENCE: 2

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110
```

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 3
<211> LENGTH: 714
<212> TYPE: DNA
<213> ORGANISM: Homo sapiens

<400> SEQUENCE: 3
atggacatga gggtcccgc tcagctcctg gggctcctgc tactctggct ccgaggtgcc      60
agatgtgaca tccagatgac ccagtctcca tcctcctgt ctgcatctgt aggagacaga     120

-continued

```
gtcaccatca cttgccgggc aagtcagagc attaacagct atttagattg gtatcagcag    180
aaaccaggga aagcccctaa actcctgatc tatgctgcat ccagtttgca aagtggggtc    240
ccatcaaggt tcagtggcag tggatctggg acagatttca ctctcaccat cagcagtctg    300
caacctgaag attttgcaac ttactactgt caacagtatt acagtactcc attcactttc    360
ggccctggga ccaaagtgga aatcaaacga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta gtga          714
```

<210> SEQ ID NO 4
<211> LENGTH: 214
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 125
<212> TYPE: PRT
<213> ORGANISM: Homo sapiens

<400> SEQUENCE: 5

Gln Val Gln Leu Val Glu Ser Gly Gly Gly Val Val Gln Pro Gly Arg

```
                1               5                   10                  15
Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
                100                 105                 110

Asp Val Trp Gly Gln Gly Thr Thr Val Thr Val Ser Ser
            115                 120                 125
```

<210> SEQ ID NO 6
<211> LENGTH: 107
<212> TYPE: PRT
<213> ORGANISM: Homo sapiens

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
                20                  25                  30

Leu Asp Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys
                100                 105
```

<210> SEQ ID NO 7
<211> LENGTH: 10
<212> TYPE: PRT
<213> ORGANISM: Homo sapiens

<400> SEQUENCE: 7

```
Gly Phe Thr Phe Ser Ser Tyr Gly Met His
1               5                   10
```

<210> SEQ ID NO 8
<211> LENGTH: 15
<212> TYPE: PRT
<213> ORGANISM: Homo sapiens

<400> SEQUENCE: 8

```
Val Ile Trp Tyr Asp Gly Ser Asn Lys Tyr Tyr Ala Asp Ser Val
1               5                   10                  15
```

<210> SEQ ID NO 9
<211> LENGTH: 16
<212> TYPE: PRT
<213> ORGANISM: Homo sapiens

-continued

<400> SEQUENCE: 9

Asp Pro Arg Gly Ala Thr Leu Tyr Tyr Tyr Tyr Gly Met Asp Val
1               5                   10                  15

<210> SEQ ID NO 10
<211> LENGTH: 11
<212> TYPE: PRT
<213> ORGANISM: Homo sapiens

<400> SEQUENCE: 10

Arg Ala Ser Gln Ser Ile Asn Ser Tyr Leu Asp
1               5                   10

<210> SEQ ID NO 11
<211> LENGTH: 7
<212> TYPE: PRT
<213> ORGANISM: Homo sapiens

<400> SEQUENCE: 11

Ala Ala Ser Ser Leu Gln Ser
1               5

<210> SEQ ID NO 12
<211> LENGTH: 9
<212> TYPE: PRT
<213> ORGANISM: Homo sapiens

<400> SEQUENCE: 12

Gln Gln Tyr Tyr Ser Thr Pro Phe Thr
1               5

<210> SEQ ID NO 13
<211> LENGTH: 364
<212> TYPE: PRT
<213> ORGANISM: Homo sapiens

<400> SEQUENCE: 13

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
                20                  25                  30

Ala Val Val Leu Ala Ser Ser Arg Gly Ile Ala Ser Phe Val Cys Glu
            35                  40                  45

Tyr Ala Ser Pro Gly Lys Ala Thr Glu Val Arg Val Thr Val Leu Arg
        50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
                100                 105                 110

Thr Gly Leu Tyr Ile Cys Lys Val Glu Leu Met Tyr Pro Pro Pro Tyr
            115                 120                 125

Tyr Leu Gly Ile Gly Asn Gly Thr Gln Ile Tyr Val Ile Asp Pro Glu
        130                 135                 140

Pro Cys Pro Asp Ser Asp Leu Glu Gly Ala Pro Ser Val Phe Leu Phe
145                 150                 155                 160

Pro Pro Lys Pro Lys Asp Thr Leu Met Ile Ser Arg Thr Pro Glu Val
                165                 170                 175

-continued

```
Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Thr Pro Glu Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 14
<211> LENGTH: 12
<212> TYPE: PRT
<213> ORGANISM: Homo sapiens

<400> SEQUENCE: 14

Met His Val Ala Gln Pro Ala Val Val Leu Ala Ser
1               5                   10

<210> SEQ ID NO 15
<211> LENGTH: 120
<212> TYPE: PRT
<213> ORGANISM: Homo sapiens

<400> SEQUENCE: 15

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys
        115                 120
```

```
<210> SEQ ID NO 16
<211> LENGTH: 11
<212> TYPE: PRT
<213> ORGANISM: Homo sapiens

<400> SEQUENCE: 16

Met His Val Ala Gln Pro Ala Val Val Leu Ala
1               5                   10

<210> SEQ ID NO 17
<211> LENGTH: 15
<212> TYPE: PRT
<213> ORGANISM: Homo sapiens

<400> SEQUENCE: 17

Gly Leu Glu Trp Val Ala Val Ile Trp Tyr Asp Gly Ser Asn Lys
1               5                   10                  15

<210> SEQ ID NO 18
<211> LENGTH: 10
<212> TYPE: PRT
<213> ORGANISM: Homo sapiens

<400> SEQUENCE: 18

Gly Leu Glu Trp Val Ala Val Ile Trp Tyr
1               5                   10
```

US 9,487,581 B2

ANTI-CTLA-4 ANTIBODY COMPOSITIONS

CROSS-REFERENCE TO RELATED PATENTS AND PATENT APPLICATIONS

This application claims the benefit of U.S. Provisional Patent Application Ser. No. 60/659,766 filed Mar. 8, 2005; U.S. Provisional Patent Application Ser. No. 60/728,165 filed Oct. 19, 2005; U.S. Provisional Patent Application Ser. No. 60/752,712 filed Dec. 20, 2005; and U.S. Provisional Patent Application Ser. No. 60/762,456 filed Jan. 26, 2006, all of which are incorporated by reference herein in their entireties.

REFERENCE TO SEQUENCE LISTING

A revised sequence listing in .txt format is being submitted electronically via EFS-Web. The .txt file contains a sequence entitled "PC33042A_SequenceListing.txt" created on Aug. 22, 2011 and having a size of 17 KB. The sequence listing contained in this .txt file is part of the specification and is herein incorporated by reference in its entirety.

BACKGROUND OF THE INVENTION

Cytotoxic T lymphocyte antigen-4 ("CTLA-4") is a member of the immunoglobulin ("Ig") superfamily of proteins. CTLA-4 acts to down regulate T-cell activation and maintain immunologic homeostasis. Blockade of CTLA-4 (e.g., by use of CTLA-4 antibodies) has been shown in animal models to improve the effectiveness of cancer immunotherapy.

Antibodies that bind to and inhibit the activity of CTLA-4 have been reported in the literature. For example, U.S. Pat. No. 6,682,736 assigned to Pfizer, Inc. and Abgenix, Inc., reports several human monoclonal antibodies to CTLA-4, including a CTLA-4 antibody having the heavy and light chain amino acid sequences of antibody 11.2.1, now known as Ticilimumab™. A hybridoma cell line producing antibody 11.2.1 was deposited under ATCC Accession No. PTA-5169. U.S. Pat. No. 5,977,318 assigned to Bristol-Myers Squibb Company, reports another monoclonal antibody, which recognizes and binds the extracellular domain of CTLA-4, thereby preventing the binding of CTLA-4 to the B7 antigen. U.S. Published Application No. 20050201994 assigned to Medarex, Inc. reports several human sequence antibodies to CTLA-4, including one now referred to as Ipilimumab™.

One possible mode of administering such CTLA-4 antibodies is by parenteral administration. For example, U.S. Pat. No. 6,682,736 reports an anti-CTLA-4 antibody intravenous formulation that is a sterile liquid solution containing anti-CTLA-4 antibodies, 20 mM sodium acetate, 0.2 mg/ml polysorbate 80, and 140 mM sodium chloride at pH 5.5.

Like other protein formulations, CTLA-4 antibody formulations are subject to the same concerns regarding chemical and physical degradation of the antibody in the formulation over time. In general, CTLA-4 antibody formulations should exhibit acceptable chemical and physical stability under the expected range of storage and use conditions, i.e., the CTLA-4 antibody formulation should have a sufficient shelf life yet remain biologically active. Given the time and resources necessary to produce a CTLA-4 antibody product, formulations that reduce product loss are desirable. Accordingly, the present application discloses novel CTLA-4 antibody formulations that exhibit improved chemical and/or physical stability relative to CTLA-4 antibody formulations previously disclosed in the literature.

SUMMARY

In one aspect, the present invention provides a liquid pharmaceutical composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a chelating agent.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody is an IgG2 antibody.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody is a human antibody.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody comprises a $V_H$ amino acid sequence that utilizes a human $V_H$ 3-33 germline gene.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody has a $V_H$ amino acid sequence that comprises human FR1, FR2, and FR3 sequences that utilize a human $V_H$ 3-33 gene family operably linked in frame with a CDR1, a CDR2, and a CDR3 sequence.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody is an isolated antibody.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody is a recombinant antibody.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody specifically binds to a conformational epitope on the human CTLA-4 polypeptide.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody comprises a heavy chain amino acid sequence with at least 95% sequence identity to SEQ ID NO: 2 and a light chain amino acid sequence with at least 95% sequence identity to SEQ ID NO: 4.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody comprises a heavy chain amino acid sequence with at least 99% sequence identity to SEQ ID NO: 2 and a light chain amino acid sequence with at least 99% sequence identity to SEQ ID NO: 4.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody comprises a heavy chain amino acid sequence that comprises the variable region of SEQ ID NO: 2 and a light chain amino acid sequence that comprises the variable region SEQ ID NO: 4.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody comprises a heavy chain variable region amino acid sequence that comprises SEQ ID NO: 5 and a light chain variable region amino acid sequence that comprises the comprises SEQ ID NO: 6.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody comprises a heavy chain amino acid sequence comprising SEQ ID NO: 2 and a light chain amino acid sequence comprising SEQ ID NO: 4.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the C-terminal lysine of the heavy chain of the antibody is not present.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody comprises a monoclonal IgG2 anti-CTLA-4 antibody having the heavy and light chain amino acid sequences of antibody 11.2.1.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody has the same heavy and light chain amino acid sequences as the antibody produced by hybridoma cell line 11.2.1.4 deposited under ATCC Accession No. PTA-5169.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody is ticilimumab.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the chelating agent is selected from the group consisting of aminopolycarboxylic acids, hydroxyaminocarboxylic acids, EDTA salts and derivatives, N-substituted glycines, deferoxamine derivatives and mixtures thereof.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the chelating agent is selected from the group consisting of ethylenediaminetetraacetic acid, diethylenetriamine pentaacetic acid 5, nitrilotriacetic acid, N-2-acetamido-2-iminodiacetic acid, bis(aminoethyl) glycolether, N,N,N',N'-tetraacetic acid, trans-diaminocyclohexane tetraacetic acid, glutamic acid, aspartic acid, N-hydroxyethyliminodiacetic acid, N,N-bis-hydroxyethylglycine, N-(trishydroxymethylmethyl) glycine, glycylglycine, 2-(2-amino-2-oxoethyl) aminoethane sulfonic acid, deferoxamine, deferoxamine mesylate, dipotassium edetate, disodium edetate, edetate calcium disodium, sodium edetate, trisodium edetate, potassium edetate, citric acid, sodium citrate, anhydrous citric acid, trisodium-citrate-dihydrate, niacinamide, sodium desoxycholate, and mixtures thereof.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the chelating agent is EDTA.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, further comprising a buffer.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, further comprising a buffer, wherein the buffer is selected from the group consisting of acetate, succinate, gluconate, citrate, histidine, acetic acid, phosphate, phosphoric acid, ascorbate, tartaric acid, maleic acid, glycine, lactate, lactic acid, ascorbic acid, imidazole, bicarbonate and carbonic acid, succinic acid, sodium benzoate, benzoic acid, gluconate, edetate, acetate, malate, imidazole, tris, phosphate, and mixtures thereof.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, further comprising a buffer, wherein the buffer comprises histidine.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, further comprising histidine, wherein the histidine comprises L-histidine or D-histidine.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, further comprising histidine, wherein the histidine comprises L-histidine.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition contains a concentration of antibodies ranging from about 0.1 to about 200 mg/ml.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition contains a concentration of antibodies of about 20 mg/ml.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least two excipients selected from the group consisting of tonicity agents, surfactants, and buffers.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises a tonicity agent, a surfactant and a buffer.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises a tonicity agent, an antioxidant, a surfactant and a buffer.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the tonicity agent comprises a saccharide.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the tonicity agent comprises at least one excipient that is selected from the group consisting of fructose, glucose, mannose, sorbose, xylose, lactose, maltose, sucrose, dextran, pullulan, dextrin, cyclodextrins, soluble starch, hydroxyethyl starch, water-soluble glucans, and mixtures thereof.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the tonicity agent comprises a polyol.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the polyol comprises is selected from the group consisting of mannitol, trehalose, sorbitol, erythritol, isomalt, lactitol, maltitol, xylitol, glycerol, lactitol, propylene glycol, polyethylene glycol, inositol, and mixtures thereof.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the tonicity agent comprises a non-reducing sugar.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the tonicity agent comprises a non-reducing sugar, wherein the non-reducing sugar comprises at least one excipient that is selected from the group consisting of sucrose, trehalose, and mixtures thereof.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the tonicity agent comprises a non-reducing sugar, wherein the non-reducing sugar is trehalose.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the surfactant is selected from the group consisting of polysorbates, poloxamers, tritons, sodium dodecyl sulfate, sodium laurel sulfate, sodium octyl glycoside, laurylsulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine, myristamidopropyl-dimethylamine, palmidopropyl-dimethylamine, isostearamidopropyl-dimethylamine, sodium methyl cocoyl-taurate, disodium methyl oleyl-taurate, dihydroxypropyl PEG 5 linoleammonium chloride, polyethylene glycol, polypropylene glycol, and mixtures thereof.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the surfactant is selected from the group consisting of polysorbate 20, polysorbate 21, polysorbate 40, polysorbate 60, polysorbate 61, polysorbate 65, polysorbate 80, polysorbate 81, polysorbate 85, and mixtures thereof.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the surfactant is polysorbate 80.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises at least one excipient selected from the group consisting of tonicity agents, surfactants, and buffers, wherein the buffer comprises histidine.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises polysorbate 80.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the composition further comprises trehalose.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the composition has a pH from about 5.0 to about 6.5.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the concentration of histidine is between about 1 mM to about 50 mM.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the concentration of histidine is about 20 mM.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the concentration of polysorbate 80 is between about 0.01 mg/ml to about 10 mg/ml.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the concentration of polysorbate 80 is about 0.2 mg/ml.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the concentration of EDTA is between about 0.001 mg/ml to about 10 mg/ml.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the concentration of EDTA is about 0.1 mg/ml.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the concentration of trehalose is between about 10 mg/ml to about 100 mg/ml.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the concentration of trehalose is about 84 mg/ml.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the composition comprises from about 0.1 mg/ml to about 100 mg/ml of antibody; from about 0.001 mg/ml to about 1.0 mg/ml of EDTA; from about 1 mM to about 50 mM of histidine; from about 0.01 mg/ml to about 10 mg/ml of polysorbate 80; and from about 10 mg/ml to about 100 mg/ml of trehalose.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; wherein the composition comprises histidine, trehalose, polysorbate 80 and EDTA, wherein the composition comprises: about 20 mg/ml of antibody; about 0.1 mg/ml of EDTA; about 20 mM of histidine; about 0.2 mg/ml of polysorbate 80; and about 84 mg/ml of trehalose.

The present invention also provides a composition comprising at least one antibody wherein the antibody comprises a heavy chain amino acid sequence comprising SEQ ID NO: 2 and a light chain amino acid sequence comprising SEQ ID NO: 4, wherein the antibody binds to human CTLA-4; and a chelating agent, and the antibody is stable at a temperature of about 5° C. for at least about 26 weeks.

The present invention also provides a composition comprising at least one antibody wherein the antibody comprises a heavy chain amino acid sequence comprising SEQ ID NO: 2 and a light chain amino acid sequence comprising SEQ ID NO: 4, wherein the antibody binds to human CTLA-4; and a chelating agent, and the antibody is stable at a temperature of about 25° C. for at least about 26 weeks.

The present invention also provides a composition comprising at least one antibody wherein the antibody comprises a heavy chain amino acid sequence comprising SEQ ID NO: 2 and a light chain amino acid sequence comprising SEQ ID NO: 4, wherein the antibody binds to human CTLA-4; and a chelating agent, and the antibody is stable at a temperature of about 40° C. for at least about 26 weeks.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody is stable during at least one cycle of freezing and thawing of the composition.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein the antibody is stable during at least six cycles of freezing and thawing of the composition.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein when the composition is stored for a period of about 24 weeks at a temperature of about 40° C., the decrease between an aggregate chromatogram peak area for the composition and an aggregate chromatogram peak area for an otherwise identical composition lacking the chelating agent that is stored for a period of about 24 weeks at a temperature of about 40° C., is at least about 2%.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein when the composition is stored for a period of about 24 weeks at a temperature of about 40° C., the decrease between an aggregate chromatogram peak area for the composition and an aggregate chromatogram peak area for an otherwise identical composition lacking the chelating agent that is stored for a period of about 24 weeks at a temperature of about 40° C., is at least about 2%, wherein the chromatographic separation comprises SE-HPLC.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein when the composition is stored for a period of about 24 weeks at a temperature of about 40° C., the decrease between an aggregate chromatogram peak area for the composition and an aggregate chromatogram peak area for an otherwise identical composition lacking the chelating agent that is stored for a period of about 24 weeks at a temperature of about 40° C., is at least about 2%, wherein ultraviolet detection is used to measure the amount of antibodies that have aggregated.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein when the composition is stored for a period of about 24 weeks at a temperature of about 40° C., the decrease between an aggregate chromatogram peak area for the composition and an aggregate chromatogram peak area for an otherwise identical composition lacking the chelating agent that is stored for a period of about 24 weeks at a temperature of about 40° C., is at least about 2%, wherein the ultraviolet detection is performed at 214 nanometers.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein when the composition is stored for a period of about 24 weeks at a temperature of about 40° C., the decrease between an aggregate chromatogram peak area for the composition and an aggregate chromatogram peak area for an otherwise identical composition lacking the chelating agent that is stored for a period of about 24 weeks at a temperature of about 40° C., is at least about 2%, wherein after the composition is stored for a period of about 24 weeks at a temperature of about 40° C., the composition remains substantially clear and colorless.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein when the composition is stored for a period of about 24 weeks at a temperature of about 40° C., the decrease between an aggregate chromatogram peak area for the composition and an aggregate chromatogram peak area for an otherwise identical composition lacking the chelating agent that is stored for a period of about 24 weeks at a temperature of about 40° C., is at least about 2%, wherein when the composition is stored for a period of about 24 weeks at a temperature of about 40° C., the total percent oxidation of methionine residues at amino acid position 432 is reduced by an amount that is equal to or greater than 2.2%, as determined after enzymatic digestion with Lysyl Endopeptidase followed by separation with reversed phase HPLC, when compared to the antibodies in a composition that is free of a chelating agent.

The present invention also provides a composition comprising at least one antibody comprising an amino acid sequence that is at least 90% identical to a heavy chain amino acid sequence shown in SEQ ID NO: 2, and further comprising an amino acid sequence that is at least 90% identical to a light chain amino acid sequence shown in SEQ ID NO: 4, wherein the antibody binds to human CTLA-4; and a chelating agent, wherein when the composition is stored for a period of about 24 weeks at a temperature of about 40° C., the decrease between an aggregate chromatogram peak area for the composition and an aggregate chromatogram peak area for an otherwise identical composition lacking the chelating agent that is stored for a period of about 24 weeks at a temperature of about 40° C., is at least about 2%, wherein when the composition is stored for a period of about 24 weeks at a temperature of about 40° C., the total percent oxidation of methionine residues at amino acid position 256 is reduced by an amount that is equal to or greater than 4.2%, as determined after enzymatic digestion with Lysyl Endopeptidase followed by separation with reversed phase HPLC, when compared to the antibodies in a composition that is free of a chelating agent.

The present invention also provides a composition comprising at least one antibody consisting essentially of an amino acid sequence that is at least 90% identical to a heavy chain amino acid sequence shown in SEQ ID NO: 2, and further consisting essentially of an amino acid sequence that is at least 90% identical to a light chain amino acid sequence shown in SEQ ID NO: 4, wherein the antibody binds to human CTLA-4; and a chelating agent.

The present invention also provides a composition comprising at least one antibody consisting of an amino acid sequence that is at least 90% identical to a heavy chain amino acid sequence shown in SEQ ID NO: 2, and further consisting of an amino acid sequence that is at least 90% identical to a light chain amino acid sequence shown in SEQ ID NO: 4, wherein the antibody binds to human CTLA-4; and a chelating agent.

The present invention also provides a method for preparing a stable liquid pharmaceutical composition comprising mixing monoclonal anti-CTLA-4 antibodies with a pharmaceutically acceptable chelating agent in an amount which reduces instability of the antibody, wherein when the composition is stored for a period of about 24 weeks at a temperature of about 40° C.; the decrease between an aggregate chromatogram peak area for the stable liquid pharmaceutical composition comprising monoclonal anti-CTLA-4 antibodies and the chelating agent; and an aggregate chromatogram peak area for an otherwise identical composition lacking the chelating agent that is stored for a period of about 24 weeks at a temperature of about 40° C., is at least about 2%.

The present invention also provides a method for stabilizing monoclonal anti-CTLA-4 antibodies in a liquid pharmaceutical composition comprising forming a liquid composition comprising the antibodies and a pharmaceutically acceptable chelating agent, wherein when the composition is stored for a period of about 24 weeks at a temperature of about 40° C.; the decrease between an aggregate chromatogram peak area for the stable liquid pharmaceutical composition comprising monoclonal anti-CTLA-4 antibodies and the chelating agent; and an aggregate chromatogram peak area for an otherwise identical composition lacking the chelating agent that is stored for a period of about 24 weeks at a temperature of about 40° C., is at least about 2%.

The present invention also provides a method for the treatment of a neoplasia condition in a subject, comprising administering to the subject a liquid pharmaceutical composition comprising: a therapeutically effective amount of monoclonal anti-CTLA-4 antibody ticilimumab; and a pharmaceutically acceptable chelating agent.

The present invention also provides a method for the treatment of a neoplasia condition in a subject, comprising administering to the subject a liquid pharmaceutical composition comprising: a therapeutically effective amount of monoclonal anti-CTLA-4 antibody ticilimumab; and a pharmaceutically acceptable chelating agent, wherein the composition is administered to the subject intravenously.

The present invention also provides a method for the treatment of a neoplasia condition in a subject, comprising administering to the subject a liquid pharmaceutical composition comprising: a therapeutically effective amount of monoclonal anti-CTLA-4 antibody ticilimumab; and a pharmaceutically acceptable chelating agent, wherein the subject is in need of the treatment of a neoplasia condition.

The present invention also provides a method for the treatment of a neoplasia condition in a subject, comprising administering to the subject a liquid pharmaceutical composition comprising: a therapeutically effective amount of monoclonal anti-CTLA-4 antibody ticilimumab; and a pharmaceutically acceptable chelating agent, wherein the neoplasia condition is a cancer that is selected from the group consisting of brain, squamous cell, bladder, gastric, pancreatic, breast, head, neck, esophageal, prostate, colorectal, lung, renal, kidney, ovarian, gynecological and thyroid cancer.

The present invention also provides a kit for preparing a liquid composition of a stabilized antibody comprising: a first container comprising monoclonal anti-CTLA-4 antibody ticilimumab in solution, and a second container comprising a pharmaceutically acceptable chelating agent.

The present invention also provides an article of manufacture comprising a container which holds a mixture of at least one anti-CTLA-4 antibody having the heavy and light chain amino acid sequences of ticilimumab, and a chelating agent.

The present invention also provides a liquid pharmaceutical composition comprising monoclonal anti-CTLA-4 antibodies and a pharmaceutically acceptable chelating agent, wherein the molar concentration of the antibodies range from about 0.0006 millimolar to about 1.35 millimolar and the molar concentration of the chelating agent ranges from about 0.003 millimolar to about 50 millimolar, and wherein the molar ratio of antibodies to chelating agent ranges from about 0.00001 to about 450.

The present invention also provides a liquid pharmaceutical composition comprising monoclonal anti-CTLA-4 antibodies and a pharmaceutically acceptable chelating agent, wherein the molar concentration of the antibodies range from about 0.0006 millimolar to about 1.35 millimolar and the molar concentration of the chelating agent ranges from about 0.003 millimolar to about 50 millimolar, and wherein the molar ratio of antibodies to chelating agent ranges from about 0.00001 to about 450, wherein the antibodies comprise monoclonal anti-CTLA-4 antibodies having the heavy and light chain amino acid sequences of antibody ticilimumab.

The present invention also provides a liquid pharmaceutical composition comprising monoclonal anti-CTLA-4 antibodies and a pharmaceutically acceptable chelating agent, wherein the molar concentration of the antibodies range from about 0.0006 millimolar to about 1.35 millimolar and the molar concentration of the chelating agent ranges from about 0.003 millimolar to about 50 millimolar, and wherein the molar ratio of antibodies to chelating agent ranges from about 0.0001 to about 100.

The present invention also provides a liquid pharmaceutical composition comprising monoclonal anti-CTLA-4 antibodies and a pharmaceutically acceptable chelating agent, wherein the molar concentration of the antibodies range from about 0.0006 millimolar to about 1.35 millimolar and the molar concentration of the chelating agent ranges from about 0.003 millimolar to about 50 millimolar, and wherein the molar ratio of antibodies to chelating agent ranges from about 0.001 to about 10.

The present invention also provides a liquid pharmaceutical composition comprising monoclonal anti-CTLA-4 antibodies and a pharmaceutically acceptable chelating agent, wherein the molar concentration of the antibodies range from about 0.0006 millimolar to about 1.35 millimolar and the molar concentration of the chelating agent ranges from about 0.003 millimolar to about 50 millimolar, and wherein the molar ratio of antibodies to chelating agent ranges from about 0.1 to about 1.

The present invention also provides a liquid pharmaceutical composition comprising monoclonal anti-CTLA-4 antibodies and a pharmaceutically acceptable chelating agent, wherein the molar concentration of the antibodies range from about 0.0006 millimolar to about 1.35 millimolar and the molar concentration of the chelating agent ranges from about 0.003 millimolar to about 50 millimolar, and wherein the molar ratio of antibodies to chelating agent ranges from about 0.00001 to about 450, wherein the molar ratio of antibodies to chelating agent is about 0.5.

The present invention also provides a liquid pharmaceutical composition comprising at least one human monoclonal anti-CTLA antibody, wherein the antibody binds to human CTLA-4; and a chelating agent.

The present invention also provides a pharmaceutical composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that is at least about 10 mg/ml.

The present invention also provides a pharmaceutical composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that ranges from about 10 mg/ml to about 25 mg/ml.

The present invention also provides a pharmaceutical composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that ranges from about 10 mg/ml to about 0.200 mg/ml.

The present invention also provides a pharmaceutical composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that is about 20 mg/ml.

The present invention also provides a composition comprising: at one chelating agent; and at least one antibody comprising: an amino acid sequence that is at least 90% identical to a heavy chain amino acid sequence shown in SEQ ID NO: 2, an amino acid sequence that is at least 90% identical to a light chain amino acid sequence shown in SEQ ID NO: 4, wherein the antibody binds to human CTLA-4.

The present invention also provides a composition comprising: at one chelating agent; and at least one antibody comprising: an amino acid sequence that is at least 90% identical to a heavy chain amino acid sequence shown in SEQ ID NO: 2, an amino acid sequence that is at least 90% identical to a light chain amino acid sequence shown in SEQ ID NO: 4, wherein the antibody binds to human CTLA-4, wherein the antibody comprises a monoclonal IgG2 anti-CTLA-4 antibody having the heavy and light chain amino acid sequences of ticilimumab.

The present invention also provides a method for preparing a liquid pharmaceutical composition comprising mixing at least one anti-CTLA-4 antibody having the heavy and light chain amino acid sequences of ticilimumab in solution, with at least one chelating agent.

The present invention also provides a method for the treatment of a neoplasia condition in a subject, comprising administering to the subject a liquid pharmaceutical composition comprising: a therapeutically effective amount of at least one anti-CTLA-4 antibody having the heavy and light chain amino acid sequences of ticilimumab; and a pharmaceutically acceptable chelating agent.

The present invention also provides a kit for preparing a liquid composition of a stabilized antibody comprising: a first container comprising at least one anti-CTLA-4 antibody having the heavy and light chain amino acid sequences of ticilimumab in solution, and a second container comprising a pharmaceutically acceptable chelating agent.

The present invention also provides a liquid pharmaceutical composition comprising: at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that is at least about 10 mg/ml.

BRIEF DESCRIPTION OF THE DRAWINGS

FIG. 11, comprising FIGS. 11A-11D, shows the nucleotide and amino acid sequences for anti-CTLA4 antibody 11.2.1, now referred to as ticilimumab. FIG. 11A shows the full length nucleotide sequence for the 11.2.1 heavy chain (SEQ ID NO: 1). FIG. 11B shows the full length amino acid sequence for the 11.2.1 heavy chain (SEQ ID NO: 2), and the amino acid sequence for the 11.2.1 heavy chain variable region as indicated between brackets "[ ]" (SEQ ID NO: 5). The amino acid sequence of each 11.2.1 heavy chain CDR is underlined. The CDR sequences are as follows: CDR1: GFTFSSYGMH (SEQ ID NO: 7); CDR2: VIWYDGSNKYYADSV (SEQ ID NO: 8); and CDR3: DPRGATLYYYYYGMDV (SEQ ID NO: 9). FIG. 11C shows the nucleotide sequence for the 11.2.1 light chain (SEQ ID NO: 3). FIG. 11D shows the amino acid sequence of the full-length 11.2.1 light chain (SEQ ID NO: 4), and the light chain variable region as indicated between brackets "[ ]" (SEQ ID NO: 6). The amino acid sequence of each CDR is indicated as follows: CDR1: RASQSINSYLD (SEQ ID NO: 10); CDR2: AASSLQS (SEQ ID NO: 11); and CDR3: QQYYSTPFT (SEQ ID NO: 12).

DETAILED DESCRIPTION OF THE INVENTION

Figure 1:
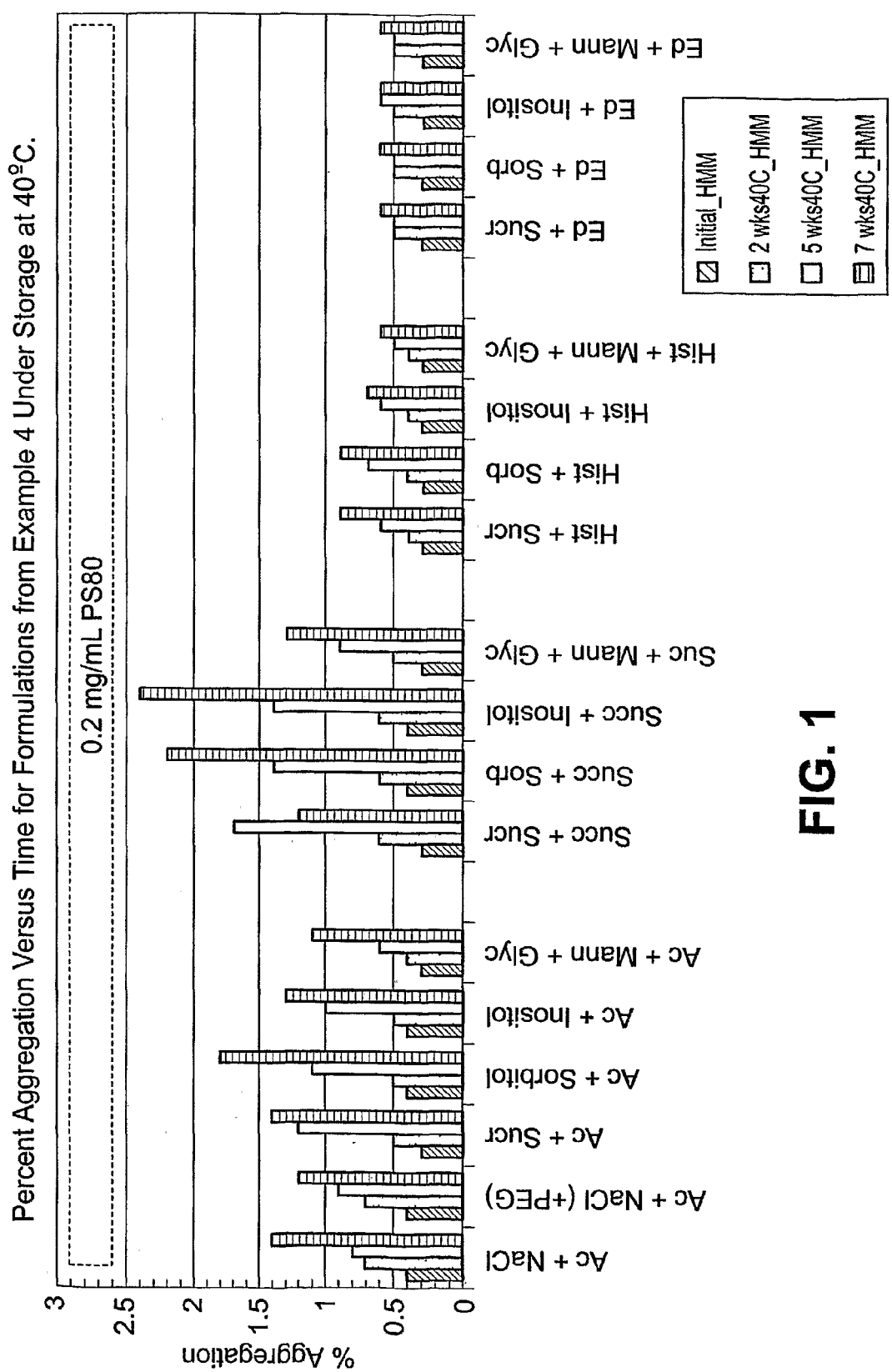
FIG. 1 is a bar graph that shows the percent aggregation in various test formulations after storage at 40° C. for up to 7 weeks by size exclusion chromatography (SEC)

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual,* 2d ed., Cold Spring Harbor Laboratory Press, Cold Spring Harbor, N.Y. (1989) and Ausubel et al., *Current Protocols in Molecular, Biology,* Greene Publishing Associates (1992), and Harlow and Lane *Antibodies: A Laboratory Manual,* Cold Spring Harbor Laboratory Press, Cold Spring Harbor, N.Y. (1990). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of subjects.

DEFINITIONS

In order to aid the reader in understanding the following detailed description, the following definitions are provided:

As used herein, the terms "formulation" or "composition" as they relate to an anti-CTLA-4 antibody are meant to describe the antibody in combination with a pharmaceutically acceptable excipient comprising a chelating agent. For example, the formulations of the invention have an improved shelf life and/or stability as compared to art recognized formulations.

As used herein, the term "antibody" refers to an intact antibody or an antigen-binding portion that competes with the intact antibody for specific binding. See generally, *Fundamental Immunology,* Ch. 7 (Paul, W., ed., 2nd ed. Raven Press, N.Y. (1989). Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. (1987 and 1991)), Chothia & Lesk, *J. Mol. Biol.* 196:901-917 (1987), or Chothia et al., *Nature* 342:878-883 (1989).

As used herein, the term "polypeptide" encompasses native or artificial proteins, protein fragments and polypeptide analogs of a protein sequence. A polypeptide may be monomeric or polymeric.

As used herein, an Fd fragment means an antibody fragment that consists of the $V_H$ and $C_H1$ domains; an Fv fragment consists of the $V_L$ and $V_H$ domains of a single arm of an antibody; and a dAb fragment (Ward et al., Nature 341:544-546 (1989)) consists of a $V_H$ domain.

The term "or an antigen-binding portion thereof" when used with the term "antibody" refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

As used herein, the term "monoclonal antibody" refers to an antibody obtained from a population of substantially homogeneous antibodies, i.e., the individual antibodies comprising the population are identical except for possible naturally occurring mutations that may be present in minor amounts or lacking a C-terminal lysine. Monoclonal antibodies are highly specific, being directed against a single antigenic site. Furthermore, in contrast to conventional (polyclonal) antibody preparations, which typically include different antibodies, directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson, et al., Nature 352:624-628 (1991) and Marks, et al., J. Mol. Biol. 222:581-597 (1991), for example.

As used herein, the terms "isolated antibody" or "purified antibody" refers to an antibody that by virtue of its origin or source of derivation has one to four of the following: (1) is not associated with naturally associated components that accompany it in its native state, (2) is free of other proteins from the same species, (3) is expressed by a cell from a different species, or (4) does not occur in nature. Thus, an antibody that is chemically synthesized or synthesized in a cellular system different from the cell from which it naturally originates is isolated and purified from its naturally associated components. An antibody may also be rendered substantially free of naturally associated components by isolation and purification, using protein purification techniques well known in the art. Examples of isolated/purified antibodies include an anti-CTLA-4 antibody that has been affinity purified using CTLA-4, an anti-CTLA-4 antibody that has been synthesized by a hybridoma or other cell line in vitro, and a human anti-CTLA-4 antibody derived from a transgenic mouse.

Examples of isolated/purified antibodies include an anti-CTLA-4 antibody that has been affinity purified using CTLA-4, an anti-CTLA-4 antibody that has been synthesized by a hybridoma or other cell line in vitro, and a human anti-CTLA-4 antibody derived from a transgenic mouse.

Thus, in preferred embodiments, the anti-CTLA-4 antibodies have a purity of at least about 95% (w/w-weight anti-CTLA-4 antibodies/weight of components other than pharmaceutically acceptable excipients), and in further embodiments, the anti-CTLA-4 antibodies have a purity from about 95% w/w to about 99.5% w/w.

An antibody is "substantially pure," "substantially homogeneous," or "substantially purified" when at least about 60 to 75% of a sample exhibits a single species of antibody. The antibody may be monomeric or multimeric. A substantially pure antibody can typically comprise about 50%, 60%, 70%, 80% or 90% w/w of an antibody sample, more usually about 95%, and preferably will be over 99% pure. Antibody purity or homogeneity may be indicated by a number of means well known in the art, such as polyacrylamide gel electrophoresis of an antibody sample, followed by visualizing a single polypeptide band upon staining the gel with a stain well known in the art. For certain purposes, higher resolution may be achieved by using HPLC or other means well known in the art for purification.

As used herein, the term "human antibody" is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

As used herein, the term "recombinant human antibody" is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, the term "polynucleotide" or "nucleic acid", used interchangeably herein, means a polymeric form of nucleotides of at least 10 bases in length, either ribonucleotides or deoxynucleotides or a modified form of either type of nucleotide. The term includes single and double stranded forms. A "polynucleotide" or a "nucleic acid" sequence encompasses its complement unless otherwise specified. Thus, a reference to a nucleic acid having a particular sequence should be understood to encompass its complementary strand, with its complementary sequence.

As used herein, the term "isolated polynucleotide" or "isolated nucleic acid" means a polynucleotide of genomic, cDNA, or synthetic origin or some combination thereof, which by virtue of its origin or source of derivation, the isolated polynucleotide has one to three of the following: (1) is not associated with all or a portion of a polynucleotide with which the "isolated polynucleotide" is found in nature, (2) is operably linked to a polynucleotide to which it is not linked in nature, or (3) does not occur in nature as part of a larger sequence.

As used herein, the term "naturally occurring nucleotides" includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

As used herein, the term "vector" means a nucleic acid molecule capable of transporting another nucleic acid to which it has been linked. In some embodiments, the vector is a plasmid, i.e., a circular double stranded DNA loop into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

As used herein, the terms "recombinant host cell" (or simply "host cell") means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

As used herein, the terms "is capable of specifically binding" refers to when an antibody binds to an antigen with a dissociation constant that is ≤1 µM, preferably ≤1 nM and most preferably ≤10 pM.

As used herein, the terms "selectively hybridize" mean to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleic acid sequences means the percent of residues when a first contiguous sequence is compared and aligned for maximum correspondence to a second contiguous sequence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art that can be used to measure nucleotide sequence identity. For instance, polynucleotide sequences can be compared using FASTA, Gap or BESTFIT, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000), Pearson, *Methods Enzymol* 266:227-258 (1996); Pearson, *J. Mol. Biol.* 276:71-84 (1998)). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1.

A reference to a "polynucleotide" or a "nucleic acid" sequence encompasses its complement unless otherwise specified. Thus, a reference to a nucleic acid having a particular sequence should be understood to encompass its complementary strand, with its complementary sequence.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity", "percent identity" or "% identical" means that two peptide sequences, when optimally aligned, such as by the programs GAP or BESTFIT using default gap weights, as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, *Methods Mol. Biol.* 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

Sequence identity for polypeptides, is typically measured using sequence analysis software. Protein analysis software matches sequences using measures of similarity assigned to various substitutions, deletions and other modifications, including conservative amino acid substitutions. For instance, GCG contains programs such as "Gap" and "BESTFIT" which can be used with default parameters, as specified with the programs, to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, see GCG Version 6.1. (University of Wisconsin Wis.) FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters, as supplied with the programs. See, e.g., Altschul et al., *J. Mol. Biol.* 215:403-410 (1990); Altschul et al., *Nucleic Acids Res.* 25:3389-402 (1997). The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

A "therapeutically effective amount" refers to an amount effective, at dosages and for periods of time necessary, to achieve the desired therapeutic result, which includes treatment or prophylactic prevention of neoplasia conditions. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Likewise, a therapeutically effective amount of the antibody or antibody portion may vary according to factors such as the disease state, age, sex, and weight of the individual, the ability of the antibody or antibody portion to elicit a desired response in the individual, and the desired route of administration of the antibody formulation. A therapeutically effective amount is also one in which any toxic or detrimental effects of the antibody or antibody portion are outweighed by the therapeutically beneficial effects.

As used herein, the term "subject" for purposes of treatment includes any subject, and preferably is a subject who is in need of the treatment of a neoplasia condition. For purposes of prevention, the subject is any subject, and preferably is a subject that is at risk for, or is predisposed to, developing a neoplasia condition. The term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, the terms "neoplasia" and "neoplasia conditions", used interchangeably herein, refer to new cell growth that results from a loss of responsiveness to normal growth controls, e.g. to "neoplastic" cell growth. Neoplasia is also used interchangeably herein with the term "cancer" and for purposes of the present invention; cancer is one subtype of neoplasia. As used herein, the term "neoplasia condition" also encompasses other cellular abnormalities, such as hyperplasia, metaplasia and dysplasia. The terms neoplasia, metaplasia, dysplasia and hyperplasia can be used interchangeably herein and refer generally to cells experiencing abnormal cell growth.

As used herein, the term "treatment" refers to both therapeutic treatment and prophylactic or preventative measures, wherein the object is to prevent or slow down (lessen) the targeted pathologic condition or condition. Those in need of treatment include those already with the condition as well as those prone to have the condition or those in whom the condition is to be prevented.

When introducing elements of the present invention or the preferred embodiment(s) thereof, the articles "a", "an", "the" and "said" are intended to mean that there are one or more of the elements. The terms "comprising", "comprise", "comprises", "including" and "having" are intended to be inclusive and mean that there may be additional elements other than the listed elements.

Anti-CTLA-4 Antibodies:

In accordance with the present invention, it has been discovered that the stability of certain monoclonal anti-CTLA-4 antibodies that are described herein can be improved by mixing the anti-CTLA-4 antibodies with a pharmaceutically acceptable chelating agent, such as ethylenediaminetetraacetic acid ("EDTA").

While not wishing to be bound by theory, it is believed that the presence of a chelating agent in the compositions of the present invention help to improve stability of the antibody polypeptide by reducing the incidence of one or more of the following: anti-CTLA-4 antibody aggregation, fragmentation, oxidation, freeze/thaw instability, discoloration, and/or deamidation. The present invention comprises anti-CTLA-4 antibody formulations having improved chemical and/or physical stability as compared to previously disclosed antibody compositions.

Therefore, in certain aspects, the present invention provides a composition comprising a pharmaceutically acceptable chelating agent, such as EDTA and a monoclonal anti-CTLA-4 antibody or an antigen-binding portion thereof. In still other aspects, the aforementioned liquid anti-CTLA-4 antibody compositions comprising a chelating agent can include additional pharmaceutically acceptable excipients, including, but not limited to, one or more excipients that are chosen from buffers, antioxidants, tonicity agents, surfactants, and mixtures thereof.

The present invention provides novel formulations for anti-CTLA-4 antibodies. As used herein, the phrase "anti-CTLA-4 antibody" refers to any antibody, or any portion thereof, that is capable of binding to any portion of a cytotoxic T-lymphocyte-associated protein 4 ("CTLA-4") polypeptide that may be present within or isolated from any animal. In certain embodiments, the CTLA-4 polypeptide is a human CTLA-4 polypeptide.

Suitable anti-CTLA-4 antibodies for use with the present invention may be chosen from polyclonal or monoclonal antibodies. In certain aspects, the monoclonal anti-CTLA-4 antibody can be a murine, chimeric, humanized or human antibody. In further embodiments, the monoclonal anti-CTLA-4 antibody is a human monoclonal anti-CTLA-4 antibody.

In certain embodiments, the anti-CTLA-4 antibodies which are suitable for use with the present invention include those anti-CTLA-4 antibodies and methods to prepare them that are described in U.S. Pat. No. 6,682,736 to Hanson, et al., filed on Dec. 23, 1999. In other embodiments, the anti-CTLA-4 antibodies which are suitable for use with the present invention include those anti-CTLA-4 monoclonal antibodies having the heavy and light chain amino acid sequences of the antibody designated 11.2.1 in U.S. Pat. No. 6,682,736. In other embodiments, the anti-CTLA-4 antibodies which are suitable for use with the present invention include those anti-CTLA-4 monoclonal antibodies having the heavy and light chain amino acid sequences of the antibodies ticilimumab and ipilimumab. In other embodiments, the anti-CTLA-4 antibodies which are suitable for use with the present invention include those anti-CTLA-4 monoclonal antibodies having the heavy and light chain amino acid sequences of the antibody ticilimumab.

As used herein, an antibody that is referred to by number has the same heavy and light chain amino acid sequences as a monoclonal antibody that is obtained from the hybridoma of the same number. For example, monoclonal antibody 11.2.1 has the same heavy and light chain amino acid sequences as one obtained from hybridoma 11.2.1. Thus, reference to antibody 11.2.1 includes the antibody, Ticilimumab™, which has the heavy and light chain amino acid sequences shown in SEQ ID NOS. 2 and 4 and the variable domain for the heavy chain shown in SEQ ID NO. 5 and the variable domain for the light chain shown in SEQ ID NO. 6. It also includes an antibody lacking a terminal lysine on the heavy chain, as this is normally lost in a proportion of antibodies during manufacture.

In addition, such anti-CTLA-4 antibodies may be chosen based on differences in the amino acid sequences in the constant region of their heavy chains. For example, the anti-CTLA-4 antibodies may be chosen from the IgG class, which have "gamma" type heavy chains. The class and subclass of anti-CTLA-4 antibodies may be determined by any method known in the art. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

The anti-CTLA-4 antibody can be an IgG, an IgM, an IgE, an IgA, or an IgD molecule. In further embodiments, the anti-CTLA-4 antibody is an IgG and is an IgG1, IgG2, IgG3 or IgG4 subclass. However, as it will be appreciated; it is generally not desirable to kill CTLA-4 expressing cells. Rather, one generally desires to simply inhibit CTLA-4 binding with its ligands to mitigate T cell down regulation. One of the major mechanisms through which antibodies kill cells is through fixation of complement and participation in CDC. The constant region of an antibody plays an important role in connection with an antibody's ability to fix complement and participate in CDC. Thus, generally one selects the isotype of an antibody to either provide the ability of complement fixation, or not. In the case of the present invention, generally, as mentioned above, it is generally not preferred to utilize an antibody that kills the cells. There are a number of isotypes of antibodies that are capable of complement fixation and CDC, including, without limitation, the following: murine IgM, murine IgG2a, murine IgG2b, murine IgG3, human IgM, human IgG1, and human IgG3. In contrast, preferred isotypes which are not capable of complement fixation and CDC include, without limitation, human IgG2 and human IgG4. In addition to heavy chain sequence differences, the IgG antibodies differ within their subclass based on the number of disulfide bonds and length of the hinge region. For example, the IgG2 subclass has several differences distinct from the other subclasses. The IgG2 and IgG4 subclasses are known to have 4 disulfide bonds within their hinge region, while IgG1 has 2 and IgG3 has 11 disulfide bonds. Other differences for IgG2 antibodies include their reduced ability to cross the placenta and the inability of IgG2 antibodies to bind to lymphocyte Fc receptors. Thus, in certain embodiments, the anti-CTLA-4 antibody is subclass IgG2 or IgG4. In another preferred embodiment, the anti-CTLA-4 antibody is subclass IgG2.

In other embodiments, suitable anti-CTLA-4 antibodies may be chosen based on differences in the amino acid sequences in their heavy chains. For example, the anti-CTLA-4 antibodies of the present invention may have human gamma type heavy chains that utilize any of the following human $V_H$ germline genes: $V_H1$, $V_H2$, $V_H3$, $V_H4$, or $V_H5$. In certain embodiments, the anti-CTLA-4 antibodies utilize the human $V_H3$ germline gene. In further embodiments, the anti-CTLA-4 antibodies utilize the human $V_H3$ germline gene and the human DP-50 or DP-46 heavy chain variable region, and in other embodiments, the anti-CTLA-4 antibodies utilize the human DP-50 heavy chain variable region. The DP-50 gene is also referred to as a $V_H$ 3-33 family gene. The DP-46 gene is also referred to as a $V_H$ 3-30.3 family gene. In still further embodiments, the anti-CTLA-4 antibodies utilize a human $D_H$ gene that is selected from D1-26, DIR4 and DIR3, and in other embodiments, the anti-CTLA-4 antibodies utilize a D1-26 human $D_H$ gene. In still further embodiments, the anti-CTLA-4 antibodies utilize a human $J_H$ gene that is selected from $J_H4$ and $J_H6$, and in other embodiments, the anti-CTLA-4 antibodies utilize the $J_H6$ human $J_H$ gene.

In further embodiments, the anti-CTLA-4 antibodies may be chosen based on differences in the amino acid sequences of their light chains. For example, suitable anti-CTLA-4 antibodies may have lambda light chains or kappa light chains. However, in certain embodiments, the anti-CTLA-4 antibodies of the present invention have kappa light chains. In some embodiments, where the anti-CTLA-4 antibody comprises a kappa light chain, the polynucleotide encoding the variable domain of the light chain comprises a human $V_K L5$, O12, L2, B3, L15, or A27 gene and a human Jκ1, Jκ2, Jκ3, Jκ4, or Jκ5 gene. In some embodiments where the antibody comprises a kappa light chain, the light chain variable domain ($V_L$) is encoded in part by a human $V_K O12$, or $V_K A27$ gene and a human $J_K 3$ or $J_K 4$ gene. In particular embodiments of the invention, the light chain variable domain is encoded by human $V_K O12/J\kappa3$ genes.

Furthermore, the antibody can comprise a heavy chain amino acid sequence comprising human CDR amino acid sequences derived from the $V_H$ 3-30 or 3-33 gene, or conservative substitutions or somatic mutations therein. It is understood that the $V_H$ 3-33 gene encodes from FR1 through FR3 of the heavy chain variable region of an antibody molecule. Thus, the invention encompasses an antibody that shares at least 85%, more preferably, at least 90%, yet more preferably, at least 91%, even more preferably, at least 94%, yet more preferably, at least 95%, more preferably, at least 97%, even more preferably, at least 98%, yet more preferably, at least 99%, and most preferably, 100% identity, with the sequence from FR1 through FR3 of the antibody ticilimumab.

The antibody can further comprise CDR regions in its light chain derived from the A27 or the O12 gene or it may comprise the CDR regions of the antibody ticilimumab.

In other embodiments of the invention, the antibody inhibits binding between CTLA4 and B7-1, B7-2, or both. Preferably, the antibody can inhibit binding with B7-1 with an $IC_{50}$ of about 100 nM or lower, more preferably, about 10 nM or lower, for example about 5 nM or lower, yet more preferably, about 2 nM or lower, or even more preferably, for example, about 1 nM or lower. Likewise, the antibody can inhibit binding with B7-2 with an $IC_{50}$ of about 100 nM or lower, more preferably, 10 nM or lower, for example, even more preferably, about 5 nM or lower, yet more preferably, about 2 nM or lower, or even more preferably, about 1 nM or lower.

Further, in another embodiment, the anti-CTLA4 antibody has a binding affinity for CTLA4 of about $10^{-8}$, or greater affinity, more preferably, about $10^{-9}$ or greater affinity, more preferably, about $10^{-10}$ or greater affinity, and even more preferably, about $10^{-11}$ or greater affinity.

The anti-CTLA4 antibody includes an antibody that competes for binding with an antibody having heavy and light chain amino acid sequences of the antibody ticilimumab. Further, the anti-CTLA4 antibody can compete for binding with antibody ipilimumab.

In another embodiment, the antibody preferably cross-competes with an antibody having a heavy and light chain sequence, a variable heavy and a variable light chain sequence, and/or the heavy and light CDR sequences of antibody ticilimumab. For example, the antibody can bind to the epitope to which an antibody that has heavy and light chain amino acid sequences, variable sequences and/or CDR sequences, of the antibody ticilimumab binds. In another embodiment, the antibody cross-competes with an antibody having heavy and light chain sequences, or antigen-binding sequences, of MDX-D010.

In another embodiment, the invention is practiced using an anti-CTLA-4 antibody that comprises a heavy chain comprising the amino acid sequences of CDR-1, CDR-2, and CDR-3, and a light chain comprising the amino acid sequences of CDR-1, CDR-2, and CDR-3, of an antibody ticilimumab, or sequences having changes from the CDR sequences selected from the group consisting of conservative changes, wherein the conservative changes are selected from the group consisting of replacement of nonpolar residues by other nonpolar residues, replacement of polar charged residues other polar uncharged residues, replacement of polar charged residues by other polar charged residues, and substitution of structurally similar residues; non-conservative substitutions, wherein the non-conservative substitutions are selected from the group consisting of substitution of polar charged residue for polar uncharged residues and substitution of nonpolar residues for polar residues, additions and deletions.

In a further embodiment of the invention, the antibody contains fewer than 10, 7, 5, or 3 amino acid changes from the germline sequence in the framework or CDR regions. In another embodiment, the antibody contains fewer than 5 amino acid changes in the framework regions and fewer than 10 changes in the CDR regions. In one preferred embodiment, the antibody contains fewer than 3 amino acid changes in the framework regions and fewer than 7 changes in the CDR regions. In a preferred embodiment, the changes in the framework regions are conservative and those in the CDR regions are somatic mutations.

Even more preferably, the antibody shares 100% sequence identity or sequence similarity over the heavy chain and the light chain, or with the heavy chain or the light chain, separately, of an antibody ticilimumab.

In another embodiment, the antibody shares at least 80%, more preferably, at least 85%, even more preferably, at least 90%, yet more preferably, at least 94%, more preferably, at least 95%, even more preferably, at least 99%, sequence identity or sequence similarity over the heavy and light chain-full-length sequences, or over the heavy or the light chain, separately, with the sequences of germline $V_K$ A27, germline $V_K$ O12, and germline DP50 (which is an allele of the $V_H$ 3-33 gene locus). Even more preferably, the antibody shares 100% sequence identity or sequence similarity over the heavy chain sequence of germline DP50 and/or with the light chain sequence of germline A27, or germline O12.

In one embodiment, the antibody shares at least 80%, more preferably, at least 85%, even more preferably, at least 90%, yet more preferably, at least 94%, preferably, at least 95%, more preferably, at least 99%, sequence (e.g., amino acid, nucleic acid, or both) identity or sequence similarity over the heavy and light chain variable region sequences, or over the heavy or the light chain variable region sequence, separately, with the sequences of antibody 3.1.1, 4.1.1, 4.8.1, 4.10.2, 4.13.1, 4.14.3, 6.1.1, ticilimumab, 11.6.1, 11.7.1, 12.3.1.1, 12.9.1.1, ipilimumab. Even more preferably, the antibody shares 100% sequence identity or sequence similarity over the heavy chain and the light chain variable region sequences, or with the heavy chain or the light chain sequence, separately, of an antibody selected from antibody 3.1.1, 4.1.1, 4.8.1, 4.10.2, 4.13.1, 4.14.3, 6.1.1, ticilimumab, 11.6.1, 11.7.1, 12.3.1.1, 12.9.1.1, ipilimumab.

In another embodiment, the antibody shares at least 80%, more preferably, at least 85%, even more preferably, at least 90%, yet more preferably, at least 94%, more preferably, at least 95%, even more preferably, at least 99%, sequence identity or sequence similarity over heavy chain variable region sequence with the heavy chain variable sequence of heavy germline DP50 (which is an allele of the $V_H$ 3-33 gene locus) or with the light chain variable sequence of germline $V_K$ A27, or germline $V_K$ O12. Even more preferably, the antibody heavy chain region sequence shares 100% sequence identity or sequence similarity with the sequence of germline DP50 or with the light chain sequence of germline A27, or germline O12.

In one embodiment of the present invention, the antibody shares at least 80%, more preferably, at least 85%, even more preferably, at least 90%, yet more preferably, at least 95%, more preferably, at least 99%, sequence identity or sequence similarity with the heavy chain, the light chain, or both, sequences from FR1 through FR4 with the FR1 through FR4 region sequences of the antibody ticilimumab. Even more preferably, the antibody shares 100% sequence identity or sequence similarity over the heavy, light, or both, sequences from FR1 through FR4 with the antibody ticilimumab.

In another embodiment of the present invention, the antibody shares at least 80%, more preferably, at least 85%, even more preferably, at least 90%, yet more preferably, at least 95%, more preferably, at least 99%, and most preferably, about 100%, sequence identity or sequence similarity with the heavy chain sequences from FR1 through FR3 with the FR1 through FR3 region sequences of germline DP50.

In yet another embodiment of the present invention, the antibody shares at least 80%, more preferably, at least 85%, even more preferably, at least 90%, yet more preferably, at least 95%, more preferably, at least 99%, and most preferably, about 100%, sequence identity or sequence similarity with the light chain sequences from FR1 through FR4 with the FR1 through FR4 region sequences of germline $V_K$ A27, or germline $V_K$ O12.

In one embodiment of the present invention, the antibody shares at least 80%, more preferably, at least 85%, even more preferably, at least 90%, yet more preferably, at least 95%; more preferably, at least 99%, sequence identity or sequence similarity with the heavy chain, the light chain, or both, CDR-1, CDR-2 and CDR-3 sequences of the antibody ticilimumab. Even more preferably, the antibody shares 100% sequence identity or sequence similarity over the heavy, light, or both, CDR-1, CDR-2 and CDR-3 sequences with the antibody ticilimumab.

In another embodiment of the present invention, the antibody shares at least 80%, more preferably, at least 85%, even more preferably, at least 90%, yet more preferably, at least 95%, more preferably, at least 99%, and most preferably, about 100%, sequence identity or sequence similarity with the heavy chain CDR-1 and CDR-2 sequences with the CDR-1 and CDR-2 sequences of germline DP50.

In yet another embodiment of the present invention, the antibody shares at least 80%, more preferably, at least 85%, even more preferably, at least 90%, yet more preferably, at least 95%, more preferably, at least 99%, and most preferably, about 100%, sequence identity or sequence similarity with the light chain CDR-1, CDR-2 and CDR-3 sequences with the CDR-1, CDR-2 and CDR-3 sequences of germline $V_K$ A27, or germline $V_K$ O12.

In one embodiment, the anti-CTLA-4 antibody is the antibody known as ticilimumab.

Table 1 lists the heavy chain and light chain human germline gene derivation for the anti-CTLA-4 monoclonal antibody 11.2.1 (i.e., ticilimumab).

TABLE 1

| Clone | Heavy Chain DNA | | | | Light Chain DNA | | |
| --- | --- | --- | --- | --- | --- | --- | --- |
| | SEQ ID NO: | $V_H$ | $D_H$ | $J_H$ | SEQ ID NO: | $V_K$ | $J_K$ |
| 11.2.1 | 1 (cDNA) (full-length) | DP-50 (3-33) | D1-26 | 6 | 3 (cDNA) (full-length) | 012 | 3 |

Some anti-CTLA-4 antibodies in accordance with the present invention were generated with a bias towards the utilization of the DP-50 heavy chain variable region. The DP-50 gene is also referred to as a $V_H$ 3-33 family gene. In XenoMouse™ mice, there are more than 30 distinct functional heavy chain variable genes with which to generate antibodies. Bias, therefore, is indicative of a preferred binding motif of the antibody-antigen interaction with respect to the combined properties of binding to the antigen and functional activity.

In some embodiments, the antibody is a single-chain antibody (scFv) in which a $V_L$ and $V_H$ domains are paired to form a monovalent molecules via a synthetic linker that enables them to be made as a single protein chain. Bird et al., Science 242:423-426 (1988) and Huston et al., Proc. Natl. Acad. Sci. USA 85:5879-5883 (1988). In some embodiments, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. See e.g., Holliger P. et al., Proc. Natl. Acad. Sci. USA 90:6444-6448 (1993), and Poljak R. J. et al., Structure 2:1121-1123 (1994). In some embodiments, one or more CDRs from an antibody of the invention may be incorporated into a molecule either covalently or noncovalently to make it an immunoadhesin that specifically binds to CTLA-4. In such embodiments, the CDR(s) may be incorporated as part of a larger polypeptide chain, may be covalently linked to another polypeptide chain, or may be incorporated noncovalently.

In another embodiment, the anti-CTLA-4 antibody has selectivity (or specificity) for CTLA-4 that is at least 100 times greater than its selectivity for any other polypeptide. In some embodiments, the anti-CTLA-4 antibody does not exhibit any appreciable specific binding to any other protein other than CTLA-4. One can determine the selectivity of the anti-CTLA-4 antibody for CTLA-4 using methods well known in the art following the teachings of the specification. For instance, one can determine the selectivity using Western blot, FACS, ELISA, or RIA. Thus, in some embodiments, the monoclonal anti-CTLA-4 antibody is capable of specifically binding to CTLA-4.

In some embodiments, the C-terminal lysine of the heavy chain of the anti-CTLA-4 antibody of the invention is not present. In some embodiments, the C-terminal lysine of the heavy chain of the anti-CTLA-4 antibody of the invention is not present. In certain aspects of the present invention, the anti-CTLA-4 antibody typically does not comprise a signal polypeptide because the signal polypeptide is generally eliminated during post-translational modifications. In various embodiments of the invention, one or both of the heavy and light chains of the anti-CTLA-4 antibodies includes a signal sequence (or a portion of the signal sequence). In other embodiments of the invention, neither the heavy nor light chain of the anti-CTLA-4 antibodies includes a signal sequence.

Table 2 lists the sequence identifiers (SEQ ID NOS) of the nucleic acids that encode the variable region of the heavy and light chains and the corresponding predicted amino acid sequences for the anti-CTLA-4 monoclonal antibody 11.2.1.

TABLE 2

HUMAN ANTI-CTLA-4 ANTIBODY 11.2.1

| | SEQUENCE IDENTIFIER (SEQ ID NOS:) | | | |
|---|---|---|---|---|
| | Heavy | | Light | |
| MAb | cDNA | Amino Acid | cDNA | Amino Acid |
| 11.2.1 (full-length) | 1 | 2 | 3 | 4 |

In some embodiments, the nucleic acid molecule comprises a nucleotide sequence that encodes the $V_L$ amino acid sequence of monoclonal antibody 11.2.1 (SEQ ID NO: 4), or a portion thereof. In some embodiments, said portion comprises at least the CDR2 region. In some embodiments, the nucleic acid encodes the amino acid sequence of the light chain CDRs of said antibody. In some embodiments, said portion is a contiguous portion comprising CDR1-CDR3. In certain aspects, the light chain CDR1 amino acid sequence is indicated by SEQ ID NO: 10, the light chain CDR2 amino acid sequence by SEQ ID NO: 11, and the light chain CDR3 amino acid sequence by SEQ ID NO: 12.

In other embodiments, the nucleic acid molecule encodes a $V_L$ amino acid sequence that is at least 70%, 75%, 80%, 85%, 90%, 95%, 97%, 98%, or 99% identical to a $V_L$ amino acid sequence of SEQ ID NO: 4. In other embodiments, the nucleic acid molecule comprises a nucleotide sequence that encodes the light chain amino acid sequence of SEQ ID NO: 4, or a portion thereof. Nucleic acid molecules of the invention include nucleic acids that hybridize under highly stringent conditions, such as those described herein, to a nucleic acid sequence encoding the light chain amino acid sequence of SEQ ID NO: 4.

In further embodiments, the nucleic acid molecule comprises a nucleotide sequence that encodes at least a portion of the $V_H$ amino acid sequence of 11.2.1 (SEQ ID NO: 2) or said sequence having conservative amino acid mutations and/or a total of three or fewer non-conservative amino acid substitutions. In various embodiments the sequence encodes one or more CDR regions, preferably a CDR3 region, all three CDR regions, a contiguous portion including CDR1-CDR3, or the entire $V_H$ region. In certain aspects, the heavy chain CDR1 amino acid sequence is indicated by SEQ ID NO: 7, the heavy chain CDR2 amino acid sequence by SEQ ID NO: 8, and the heavy chain CDR3 amino acid sequence by SEQ ID NO: 9.

In some embodiments, the nucleic acid molecule encodes a $V_H$ amino acid sequence that is at least 70%, 75%, 80%, 85%, 90%, 95%, 97%, 98%, or 99% identical to the $V_H$ amino acid sequence of SEQ ID NO: 2. In still further embodiments, the nucleic acid molecule comprises a nucleotide sequence that encodes the heavy chain amino acid sequence of SEQ ID NO: 2 or a portion thereof. Nucleic acid molecules of the invention include nucleic acids that hybridize under highly stringent conditions, such as those described above, to a nucleotide sequence encoding the heavy chain amino acid sequence of SEQ ID NO: 2.

In certain aspects, the present invention provides a liquid pharmaceutical composition comprising at least one isolated human antibody that binds to CTLA-4, wherein the antibody comprises a $V_H$ amino acid sequence that utilizes a human $V_H$ 3-33 germline gene; and a pharmaceutically acceptable excipient comprising a chelating agent.

In other aspects, the present invention provides a liquid pharmaceutical composition comprising at least one isolated human antibody that binds to CTLA-4, wherein the antibody comprises a heavy chain amino acid sequence with at least 90% sequence identity to SEQ ID NO: 2 and a light chain amino acid sequence with at least 90% sequence identity to SEQ ID NO: 4.

In other aspects, the present invention provides a liquid pharmaceutical composition comprising at least one isolated human antibody that binds to CTLA-4, wherein the antibody comprises a heavy chain amino acid sequence with at least 95% sequence identity to SEQ ID NO: 2 and a light chain amino acid sequence with at least 95% sequence identity to SEQ ID NO: 4.

In other aspects, the present invention provides a liquid pharmaceutical composition comprising at least one isolated human antibody that binds to CTLA-4, wherein the antibody comprises a heavy chain amino acid sequence with at least 99% sequence identity to SEQ ID NO: 2 and a light chain amino acid sequence with at least 99% sequence identity to SEQ ID NO: 4.

In still other aspects, the antibody comprises a heavy chain amino acid sequence that comprises the variable region of SEQ ID NO: 2 and a light chain amino acid sequence that comprises the variable region SEQ ID NO: 4. In further aspects, the antibody comprises a heavy chain amino acid sequence comprising SEQ ID NO: 5 and a light chain amino acid sequence comprising SEQ ID NO: 6. In further aspects, the antibody comprises a heavy chain amino acid sequence comprising SEQ ID NO: 2 and a light chain amino acid sequence comprising SEQ ID NO: 4. In still other aspects, the antibody comprises a $V_H$ amino acid sequence comprising human FR1, FR2, and FR3 sequences that utilize a human $V_H$ 3-33 gene family operably linked in frame with a CDR1, a CDR2, and a CDR3 sequence.

In one embodiment, the anti-CTLA-4 antibody is ticilimumab (also known as CP-675,206), which has the heavy and light chain amino acid sequences of antibody ticilimumab.

In one embodiment of the present invention, the anti-CTLA-4 antibodies specifically bind to a conformational epitope on human CTLA-4. In other embodiments, the anti-CTLA-4 antibodies inhibit human tumor growth after administration to a subject.

Preparation of the Monoclonal Anti-CTLA-4 Antibody Formulations:

The anti-CTLA-4 antibody typically is formulated as a pharmaceutical composition for parenteral administration to a subject. In one embodiment, the pharmaceutical composition is a liquid composition. In another embodiment, the pharmaceutical composition is a liquid composition.

The compositions of the present invention involve one or more anti-CTLA-4 monoclonal antibodies of the invention in combination with pharmaceutically acceptable excipients, which comprise histidine and/or a chelating agent. The liquid formulations of the present invention involve one or more anti-CTLA-4 monoclonal antibodies of the invention in combination with pharmaceutically acceptable excipients, which comprise histidine and/or a chelating agent.

The term "pharmaceutical composition" refers to preparations which are in such form as to permit the biological activity of the active ingredients to be effective. "Pharmaceutically acceptable excipients" (vehicles, additives) are those, which can reasonably (i.e., safely) be administered to a subject to provide an effective dose of the active ingredient employed. The term "excipient" or "carrier" as used herein refers to an inert substance, which is commonly used as a diluent, vehicle, preservative, binder or stabilizing agent for drugs. As used herein, the term "diluent" refers to a pharmaceutically acceptable (safe and non-toxic for administration to a human) solvent and is useful for the preparation of the liquid formulations herein. Exemplary diluents include, but are not limited to, sterile water and bacteriostatic water for injection (BWFI).

In another embodiment, the invention is directed to a composition comprising an anti-CTLA-4 antibody and a pharmaceutically acceptable chelating agent. In another embodiment, the invention is directed to a liquid pharmaceutical composition comprising an anti-CTLA-4 antibody and EDTA. In another embodiment, the invention is directed to a composition comprising an anti-CTLA4 antibody and DTPA.

In another embodiment, the invention is directed to a composition comprising an anti-CTLA-4 antibody, a pharmaceutically acceptable chelating agent, and a pharmaceutically acceptable buffer. In another embodiment, the invention is directed to a composition comprising an anti-CTLA-4 antibody, a pharmaceutically acceptable chelating agent, and histidine. In another embodiment, the invention is directed to a composition comprising an anti-CTLA-4 antibody, EDTA, and histidine. In another embodiment, the invention is directed to a composition comprising an anti-CTLA4 antibody, DTPA, and histidine.

In another embodiment, the invention is directed to a composition comprising an anti-CTLA-4 antibody, a pharmaceutically acceptable chelating agent, and a pharmaceutically acceptable tonicity agent. In another embodiment, the invention is directed to a composition comprising an anti-CTLA-4 antibody, a pharmaceutically acceptable chelating agent, and trehalose. In another embodiment, the invention is directed to a composition comprising an anti-CTLA-4 antibody, EDTA, and trehalose. In another embodiment, the invention is directed to a composition comprising an anti-CTLA-4 antibody, DTPA, and trehalose.

In another embodiment, the invention is directed to a composition comprising an anti-CTLA-4 antibody, a pharmaceutically acceptable chelating agent, and a pharmaceutically acceptable surfactant. In another embodiment, the invention is directed to a composition comprising an anti-CTLA-4 antibody, EDTA, and a pharmaceutically acceptable surfactant. In another embodiment, the invention is directed to a composition comprising an anti-CTLA-4 antibody, DTPA, and a pharmaceutically acceptable surfactant. In another embodiment, the invention is directed to a composition comprising an anti-CTLA-4 antibody, a pharmaceutically acceptable chelating agent selected from the group consisting of EDTA and DTPA, and polysorbate 80.

In another embodiment, the invention is directed to a composition comprising anti-CTLA-4 antibody, a pharmaceutically acceptable buffer, and a pharmaceutically acceptable surfactant. In another embodiment, the invention is directed to a composition comprising anti-CTLA-4 antibody, histidine, and a pharmaceutically acceptable surfactant. In another embodiment, the invention is directed to a composition comprising anti-CTLA-4 antibody, histidine, and polysorbate 80.

In another embodiment, the invention is directed to a composition comprising an anti-CTLA-4 antibody, a pharmaceutically acceptable chelating agent, a pharmaceutically acceptable buffer, and a pharmaceutically acceptable surfactant.

In another embodiment, the invention is directed to a composition comprising an anti-CTLA-4 antibody, a pharmaceutically acceptable chelating agent, a pharmaceutically acceptable buffer, and a pharmaceutically acceptable tonicity agent.

In another embodiment, the invention is directed to a composition comprising an anti-CTLA-4 antibody, a pharmaceutically acceptable chelating agent, a pharmaceutically acceptable buffer, a pharmaceutically acceptable surfactant, and a pharmaceutically acceptable tonicity agent.

In another embodiment, the invention is directed to a composition comprising an anti-CTLA4 antibody and histidine.

The anti-CTLA-4 antibody present in the composition can be as previously described in this application. In one embodiment, the composition comprises an anti-CTLA-4 antibody comprising a $V_L$ amino acid sequence that is 90%, 95%, or 99% identical to a $V_L$ amino acid sequence shown in SEQ ID NO: 4, and further comprises a $V_H$ amino acid sequence that is 90%, 95%, or 99% identical to a $V_H$ amino acid sequence shown in SEQ ID NO: 2. In another embodiment, the composition comprises an anti-CTLA-4 antibody that is monoclonal anti-CTLA-4 antibody 11.2.1.

The anti-CTLA-4 antibody present in the liquid pharmaceutical compositions can be as previously described in this application. In one embodiment, the liquid pharmaceutical compositions comprise an anti-CTLA-4 antibody comprising a $V_L$ amino acid sequence that is 90%, 95%, or 99% identical to a $V_L$ amino acid sequence shown in SEQ ID NO: 4, and further comprises a $V_H$ amino acid sequence that is 90%, 95%, or 99% identical to a $V_H$ amino acid sequence shown in SEQ ID NO: 2. In another embodiment, the liquid pharmaceutical composition comprises an anti-CTLA-4 antibody that is monoclonal anti-CTLA-4 antibody 11.2.1.

The concentration of the anti-CTLA-4 antibody in the liquid pharmaceutical compositions of the present invention is generally at least about 0.1 milligram per milliliter (mg/ml) or higher, at least about 10 mg/ml or higher, at least about 10 mg/ml or higher, at least about 50 mg/ml or higher, at least about 100 mg/ml or higher, or at least about 200 mg/ml or higher. In certain embodiments, the concentration of the anti-CTLA-4 antibody generally ranges from about 0.1 mg/ml to about 200 mg/ml, from about 0.5 mg/ml to about 100 mg/ml, from about 1 mg/ml to about 70 mg/ml, from about 2.0 mg/ml to about 65 mg/ml, from about 5.0 mg/ml to about 50 mg/ml, from about 10 mg/ml to about 35 mg/ml, from about 15 mg/ml to about 25 mg/ml, or is about 20 mg/ml. In one embodiment, the concentration of the anti-CTLA-4 antibody in the liquid pharmaceutical composition ranges from about 50 mg/ml to about 100 mg/ml. In some embodiments, higher antibody concentrations can be used where the composition is intended for subcutaneous delivery.

As used herein, the terms "chelating agent" generally refers to an excipient that can form at least one bond (e.g., covalent, ionic, or otherwise) to a metal ion. A chelating agent is typically a multidentate ligand that can be used in selected liquid compositions as a stabilizer to complex with species, which might promote instability. Often, compounds that can act as a chelating agent will have electron-rich functional groups. Suitable electron-rich functional groups include carboxylic acid groups, hydroxy groups and amino groups. Arrangement of these groups in aminopolycarboxylic acids, hydroxypolycarboxylic acids, hydroxyaminocarboxylic acids, and the like, result in moieties that have the capacity to bind metal.

However, the present invention is not intended to be limited to chelating agents primarily by the chelating agent's ability to form bonds with a metal ion. Therefore, the present invention is not intended to be limited by any specific mechanism by which the chelating agent acts in the formulations of the present invention and the excipients termed chelating agents herein may achieve their properties through mechanisms that are altogether unrelated to the chelating agent's ability to form bonds with a metal ion.

Chelating agents that are suitable for use in the present invention, include, but are not limited to, aminopolycarboxylic acids, hydroxyaminocarboxylic acids, N-substituted glycines, 2-(2-amino-2-oxoethyl) aminoethane sulfonic acid (BES), deferoxamine (DEF), citric acid, niacinamide, and desoxycholates. Examples of suitable aminopolycarboxylic acids include ethylenediaminetetraacetic acid (EDTA), diethylenetriamine pentaacetic acid 5 (DTPA), nitrilotriacetic acid (NTA), N-2-acetamido-2-iminodiacetic acid (ADA), bis(aminoethyl)glycolether, N,N,N',N'-tetraacetic acid (EGTA), trans-diaminocyclohexane tetraacetic acid (DCTA), glutamic acid, and aspartic acid. Examples of suitable hydroxyaminocarboxylic acids include N-hydroxyethyliminodiacetic acid (HIMDA), N,N-bis-hydroxyethylglycine (bicine) and N-(trishydroxymethylmethyl) 10 glycine (tricine). An example of a suitable N-substituted glycine is glycylglycine. An example of a suitable desoxycholate is sodium desoxycholate. Mixtures of two or more chelating agents are also encompassed by the present invention.

Chelating agents used in the invention can be present, where possible, as the free acid or free base form of the compound. (e.g., referred to interchangeably herein as "EDTA" or "edetate") or as a corresponding salt form (e.g., the corresponding acid addition salt or base addition salt, such as disodium edetate). Suitable acid addition salts, e.g., include alkali metal salts (e.g., sodium or potassium salts), alkaline earth metal salts (e.g., calcium salts), and salts can be prepared using other weakly bound metal ions. As is known in the art, the nature of the salt and the number of charges to be neutralized will depend on the number of carboxyl groups present and the pH at which the stabilizing chelating agent is supplied. As is also known in the art, chelating agents have varying strengths with which particular target ions are bound. By way of further illustration, suitable salts of EDTA include dipotassium edetate, disodium edetate, edetate calcium disodium, sodium edetate, trisodium edetate, and potassium edetate; and a suitable salt of deferoxamine (DEF) is deferoxamine mesylate (DFM).

Chelating agents used in the invention can be present as an anhydrous, solvated or hydrated form of the compound or corresponding salt. Where the chelating agent is in a solvated or hydrated form, it can be present in varying states of solvation or hydration (including, e.g., anhydrous, hydrated, dihydrated, and trihydrated forms). By way of further illustration, a suitable hydrate of EDTA is disodium EDTA dihydrate; and suitable forms of citric acid include anhydrous citric acid, citric acid monohydrate, and trisodium citrate-dihydrate.

Suitable chelating agents used in the antibody compositions of the present invention also include, for example, those that bind to metal ions in solution to render them unable to react with available $O_2$, thereby minimizing or preventing generation of hydroxyl radicals which are free to react with and degrade the antibody. Chelating agents can lower the formation of reduced oxygen species, reduce acidic species (e.g., deamidation) formation, reduce antibody aggregation, and/or reduce antibody fragmentation in the compositions of the present invention. Such chelating agents can reduce or prevent degradation of an antibody that is formulated without the protection of a chelating agent.

When a concentration of a chelating agent is referred to, it is intended that the recited concentration represent the molar concentration of the free acid or free base form of the chelating agent. For example, the concentration of chelating agent in certain liquid pharmaceutical compositions generally ranges from about 0.01 micromolar to about 50 millimolar, from about 1 micromolar to about 10.0 millimolar, from about 15 micromolar to about 5.0 millimolar, from about 0.01 millimolar to about 1.0 millimolar, or from about 0.03 millimolar to about 0.5 millimolar. In certain embodiments, the concentration of chelating agent in the liquid pharmaceutical composition can be about 0.01 millimolar, 0.02 millimolar, 0.027 millimolar, 0.03 millimolar, about 0.04 millimolar, about 0.05 millimolar, about 0.06 millimolar, about 0.07 millimolar, about 0.10 millimolar, about 0.20 millimolar, about 0.26 millimolar, about 0.27 millimolar, about 0.30 millimolar, about 0.31 millimolar, about 0.34 millimolar, about 0.40 millimolar, about 0.50 millimolar, or about 1.0 millimolar. In certain embodiments, the concentration of chelating agent is about 0.027 millimolar, about 0.05 millimolar, about 0.13 millimolar, or about 0.27 millimolar. In one embodiment, the concentration of chelating agent is about 0.05 millimolar. In another embodiment, the concentration of chelating agent is about 0.13 millimolar.

Unless stated otherwise, the concentrations listed herein are those concentrations at ambient conditions, (i.e., at 25° C. and atmospheric pressure). Ranges intermediate to the above-recited chelating agent concentrations are also intended to be part of this invention. For example, ranges of values using a combination of any of the above-recited values as upper and/or lower limits are intended to be included.

In one embodiment, the chelating agent is selected from the group consisting of EDTA, DTPA, DFM, and mixtures thereof. In another embodiment, the chelating is agent is DFM. In another embodiment, the chelating agent is EDTA. In another embodiment, the chelating agent is DTPA. In another embodiment, the liquid pharmaceutical composition comprises EDTA in an amount that generally ranges from about 0.01 micromolar to about 50 millimolar, from about 1 micromolar to about 20.0 millimolar, from about 15 micromolar to about 10.0 millimolar, from about 0.01 millimolar to about 5.0 millimolar, or from about 0.03 millimolar to about 1 millimolar. In certain embodiments, the concentration of EDTA in the liquid pharmaceutical composition can be about 0.01 millimolar, 0.02 millimolar, 0.027 millimolar, 0.03 millimolar, about 0.04 millimolar, about 0.05 millimolar, about 0.06 millimolar, about 0.07 millimolar, about 0.10 millimolar, about 0.20 millimolar, about 0.26 millimolar, about 0.27 millimolar, about 0.30 millimolar, about 0.31 millimolar, about 0.34 millimolar, about 0.40 millimolar, about 0.50 millimolar, or about 1.0 millimolar. In certain embodiments, the concentration of EDTA is about 0.027 millimolar, about 0.05 millimolar, about 0.13 millimolar, or about 0.27 millimolar. In one embodiment, the concentration of EDTA is about 0.05 millimolar. In another embodiment, the concentration of EDTA is about 0.13 millimolar. In another embodiment, the liquid pharmaceutical composition comprises EDTA in an amount of about 0.27 millimolar.

As noted above, the compositions of the present invention optionally may further comprise a pharmaceutically acceptable buffer in addition to a chelating agent. As used herein, the term "buffer" refers to an added composition that allows a liquid antibody formulation to resist changes in pH. In certain embodiments, the added buffer allows a liquid antibody formulation to resist changes in pH by the action of its acid-base conjugate components.

For example, a buffered formulation may be prepared by adding L-histidine-HCl (L-histidine-hydrochloride) and L-histidine in the appropriate amounts to arrive at a desired pH. However, in other embodiments, the added buffer allows a liquid antibody formulation to resist changes in pH by the action of its acid-base conjugate components. By way of a second example, a buffered formulation may be prepared by adding an acid, such as hydrochloric acid, and L-histidine in the appropriate amounts to arrive at a desired pH.

Examples of suitable buffers include, but are not limited to, acetate (e.g., sodium acetate), succinate (e.g., sodium succinate), gluconate, citrate (e.g., and other organic acid buffers, including, but not limited to, buffers such as amino acids (e.g., histidine), acetic acid, phosphoric acid and phosphates, ascorbate, tartartic acid, maleic acid, glycine, lactate, lactic acid, ascorbic acid, imidazoles, carbonic acid and bicarbonates, succinic acid, sodium benzoic acid and benzoates, gluconate, edetate (EDTA), acetate, malate, imidazole, tris, phosphate, and mixtures thereof. In one embodiment, the buffer is acetate.

In another embodiment, the buffer is histidine. The histidine starting material used to prepare the compositions of the present invention can exist in different forms. For example, the histidine can be an enantiomeric (e.g., L- or D-enantiomer) or racemic form of histidine, a free acid or free base form of histidine, a salt form (e.g., a monohydrochloride, dihydrochloride, hydrobromide, sulfate, or acetate salt) of histidine, a solvated form of histidine, a hydrated form (e.g., monohydrate) of histidine, or an anhydrous form of histidine. The purity of histidine base and/or salt used to prepare the compositions generally can be at least about 98%, at least about 99%, or at least about 99.5%. As used herein, the term "purity" in the context of histidine refers to chemical purity of histidine as understood in the art, e.g., as described in The Merck Index, 13th ed., O'Neil et al. ed. (Merck & Co., 2001).

When a concentration of a buffer is referred to, it is intended that the recited concentration represent the molar concentration of the free acid or free base form of the buffer. For example, the concentration of the buffer when present in certain liquid pharmaceutical compositions can range from about 0.1 millimolar (mM) to about 100 mM. In one embodiment, the concentration of the buffer is from about 1 mM to about 50 mM. In another embodiment, the concentration of the buffer is from about 5 mM to about 30 mM. In various embodiments, the concentration of the buffer is about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM or about 100 mM. In one embodiment, the concentration of histidine in the pharmaceutical composition is about 10 mM. In another embodiment, the pharmaceutical composition contains about 10 mM of L-histidine (in base form). In another embodiment, the concentration of histidine in the pharmaceutical composition is about 20 mM. In another embodiment, the pharmaceutical composition contains about 20 mM of L-histidine (in base form). Ranges intermediate to the above-recited histidine concentrations are also intended to be part of this invention. For example, ranges of values using a combination of any of the above-recited values as upper and/or lower limits are intended to be included.

In general, the buffer is used to maintain an acceptable pH level (which can affect antibody stability) in the liquid pharmaceutical composition. The liquid pharmaceutical composition typically is buffered to maintain a pH in the range of from about 4 to about 8; from about 4.5 to about 7; from about 5.0 to 6.5, or from about 5.3 to about 6.3. Ranges intermediate to the above-recited pH's are also intended to be part of this invention. For example, ranges of values using a combination of any of the above-recited values as upper and/or lower limits are intended to be included. In one embodiment, the liquid pharmaceutical composition is buffered to maintain a pH of about 5.5. In another embodiment, the liquid pharmaceutical composition is buffered to maintain a pH of about 6.0.

As noted above, the compositions of the present invention optionally may further comprise a pharmaceutically acceptable tonicity agent in addition to a chelating agent. As used herein, the terms "tonicity agent" or "tonicifier" refers to an excipient that can adjust the osmotic pressure of a liquid antibody formulation. In certain embodiments, the tonicity agent can adjust the osmotic pressure of a liquid antibody formulation to isotonic so that the antibody formulation is physiologically compatible with the cells of the body tissue of the subject. In still other embodiments, the "tonicity agent" may contribute to an improvement in stability of any of the anti-CTLA-4 antibodies described herein. An "isotonic" formulation is one that has essentially the same osmotic pressure as human blood. Isotonic formulations generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example.

The tonicity agent used to prepare the compositions of the present invention can exist in different forms. When the tonicity agent is referred to, it is intended that all of these different forms are encompassed by the name of the tonicity agent. For example, the tonicity agent can be in an enantiomeric (e.g., L- or D-enantiomer) or racemic form; isomers such as alpha or beta, including alpha, alpha; or beta, beta; or alpha, beta; or beta, alpha; a free acid or free base form; a hydrated form (e.g., monohydrate), or an anhydrous form.

In one embodiment, the tonicity agent is a saccharide. As used herein, the term "saccharide" refers to a class of molecules that are derivatives of polyhydric alcohols. Saccharides are commonly referred to as carbohydrates and may contain different amounts of sugar (saccharide) units, e.g., monosaccharides, disaccharides and polysaccharides. Saccharides that are suitable for use as a tonicity agent in the present invention, include, but are not limited to, saccharides selected from the group consisting of fructose, glucose, mannose, sorbose, xylose, lactose, maltose, sucrose, dextran, pullulan, dextrin, cyclodextrins, soluble starch, hydroxyethyl starch, water-soluble glucans, and mixtures thereof.

In another embodiment, the tonicity agent is a polyol. As used herein, the term "polyol" refers an excipient with multiple hydroxyl groups, and includes sugars (reducing and nonreducing sugars), sugar alcohols and sugar acids. In one embodiment, the polyol has a molecular weight that is less than about 600 kD (e.g., in the range from about 120 to about 400 kD). A "reducing sugar" is one which contains a hemiacetal group that can reduce metal ions or react covalently with lysine and other amino groups in proteins and a "nonreducing sugar" is one which does not have these properties of a reducing sugar. Polyols that are suitable for use as a tonicity-agent in the present invention, include, but are not limited to, polyols selected from the group consisting of mannitol, trehalose, sorbitol, erythritol, isomalt, lactitol, maltitol, xylitol, glycerol, lactitol, propylene glycol, polyethylene glycol, inositol, and mixtures thereof. In one embodiment, the tonicity agent is a non-reducing sugar selected from the group consisting of trehalose, sucrose, and mixtures thereof.

In one embodiment, the tonicity agent is mannitol. In another embodiment, the tonicity agent is D-mannitol. In another embodiment, the tonicity agent is trehalose. In another embodiment, the tonicity agent is α α-trehalose dihydrate. In another embodiment, the tonicity agent is sucrose.

In one embodiment, concentration of the tonicity agent in the liquid pharmaceutical composition ranges from about 1 millimolar to about 600 millimolar, from about 1 millimolar to about 400 millimolar, from 1 millimolar to about 300 millimolar, or from 200 millimolar to about 275 millimolar. In one another embodiment, the tonicity agent is mannitol and is present in the liquid pharmaceutical composition at a concentration of about 247 millimolar. In another embodiment, the tonicity agent is trehalose and is present in the liquid pharmaceutical composition at a concentration of about 222 millimolar. In another embodiment, the tonicity agent is trehalose and is present in the liquid pharmaceutical composition at a concentration of about 238 millimolar. In another embodiment, the tonicity agent is sucrose is present in the liquid pharmaceutical composition at a concentration of about 263 millimolar.

In one embodiment, concentration of the tonicity agent in the liquid pharmaceutical composition ranges from about 1 mg/ml to about 300 mg/ml, from about 1 mg/ml to about 200 mg/ml, or from about 50 mg/ml to about 150 mg/ml. In another embodiment, the tonicity agent is mannitol and is present in the liquid pharmaceutical composition at a concentration of about 45 mg/ml millimolar. In another embodiment, the tonicity agent is trehalose and is present in the liquid pharmaceutical composition at a concentration of about 84 mg/ml. In another embodiment, the tonicity agent is trehalose and is present in the liquid pharmaceutical composition at a concentration of about 90 mg/ml. In another embodiment, the tonicity agent is sucrose and is present in the liquid pharmaceutical composition at a concentration of about 90 mg/ml.

In one embodiment, the tonicity agent is a salt, such as sodium chloride. In one embodiment, when the tonicity agent is a salt, the concentration of the salt in the liquid pharmaceutical composition ranges from about 1 mg/ml to about 20 mg/ml. In another embodiment, the tonicity agent is sodium chloride and the concentration of the sodium chloride in the liquid pharmaceutical composition is about 8.18 mg/ml.

Ranges intermediate to the above-recited tonicity agent concentrations are also intended to be part of this invention. For example, ranges of values using a combination of any of the above-recited values as upper and/or lower limits are intended to be included.

Ranges intermediate to the above-recited tonicity agent concentrations are also intended to be part of this invention. For example, ranges of values using a combination of any of the above-recited values as upper and/or lower limits are intended to be included.

As noted above, the compositions of the present invention optionally may further comprise a pharmaceutically acceptable surfactant in addition to a chelating agent. As used herein, the term "surfactant" refers to an excipient that can alter the surface tension of a liquid antibody formulation. In certain embodiments, the surfactant reduces the surface tension of a liquid antibody formulation. In still other embodiments, the "surfactant" may contribute to an improvement in stability of any of the anti-CTLA-4 antibodies described herein. For example, the surfactant may reduce aggregation of the formulated antibody and/or minimize the formation of particulates in the formulation and/or reduces adsorption. The surfactant may also improve stability of the antibody during and after a freeze/thaw cycle.

Suitable surfactants include polysorbate surfactants, poloxamers (e.g., poloxamer 18 and 407), triton surfactants, such as Triton X-100® (octylphenol ethylene oxide condensate), polysorbate surfactants such as Tween 20® (polysorbate 20) and Tween 80® (polysorbate 80), sodium dodecyl sulfate, sodium laurel sulfate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine, myristamidopropyl-dimethylamine, palmidopropyl-dimethylamine, isostearamidopropyl-dimethylamine, sodium methyl cocoyl-taurate, disodium methyl oleyl-taurate, dihydroxypropyl peg 5 linoleammonium chloride, polyethylene glycol, polypropylene glycol, and mixtures thereof.

In one embodiment, the surfactant is a polysorbate surfactant comprising at least one excipient that is selected from the group consisting of polysorbate 20, polysorbate 21, polysorbate 40, polysorbate 60, polysorbate 61, polysorbate 65, polysorbate 80, polysorbate 81, polysorbate 85, and mixtures thereof. In another embodiment, the liquid pharmaceutical composition comprises polysorbate 80.

The concentration of the surfactant when present in the composition generally ranges from about 0.01 mg/ml to about 10 mg/ml, from about 0.05 mg/ml to about 5.0 mg/ml, from about 0.1 mg/ml to about 1.0 mg/ml, or from about 0.2 mg/ml to about 0.7 mg/ml. In another embodiment, the surfactant is present in an amount that is about 0.2 mg/ml. In another embodiment, the surfactant is present in an amount that is about 0.5 mg/ml. In one embodiment, the liquid pharmaceutical composition contains about 0.2 mg/ml polysorbate 80. In another embodiment, the liquid pharmaceutical composition contains about 0.4 mg/ml polysorbate 80. In another embodiment, the liquid pharmaceutical composition contains about 0.5 mg/ml polysorbate 80.

Ranges intermediate to the above-recited surfactant concentrations are also intended to be part of this invention. For example, ranges of values using a combination of any of the above-recited values as upper and/or lower limits are intended to be included.

The compositions of the present invention optionally may further comprise a pharmaceutically acceptable antioxidant in addition to a chelating agent. Suitable antioxidants include, but are not limited to, methionine, sodium thiosulfate, catalase, and platinum. For example, the liquid pharmaceutical composition may contain methionine in a concentration that ranges from 1 mM to about 100 mM, and in particular, is about 27 mM.

In one embodiment, the present invention encompasses a composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a chelating agent.

In one embodiment, the present invention encompasses a composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a chelating agent.

In one embodiment, the present invention encompasses a composition comprising at least one human monoclonal anti-CTLA antibody, wherein the antibody binds to human CTLA-4; and a chelating agent.

In one embodiment, the present invention encompasses a liquid pharmaceutical composition comprising at least one human monoclonal anti-CTLA antibody, wherein the antibody binds to human CTLA-4; and a chelating agent.

In one embodiment, the present invention encompasses a composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that is at least about 10 mg/ml, at least about 15 mg/ml, at least about 20 mg/ml or at least about 25 mg/ml.

In one embodiment, the present invention encompasses a liquid pharmaceutical composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that ranges from about 10 mg/ml to about 200 mg/ml.

In one embodiment, the present invention encompasses a composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that ranges from about 15 mg/ml to about 200 mg/ml.

In one embodiment, the present invention encompasses a composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that ranges from about 20 mg/ml to about 200 mg/ml.

In one embodiment, the present invention encompasses a composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that ranges from about 50 mg/ml to about 200 mg/ml.

In one embodiment, the present invention encompasses a liquid pharmaceutical composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that ranges from about 100 mg/ml to about 200 mg/ml.

In one embodiment, the present invention encompasses a composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that ranges from about 10 mg/ml to about 25 mg/ml.

In one embodiment, the present invention encompasses a composition comprising at least one antibody comprising an amino acid sequence that is at least 95% identical to a heavy chain amino acid sequence shown in SEQ ID NO: 2, and further comprising an amino acid sequence that is at least 95% identical to a light chain amino acid sequence shown in SEQ ID NO: 4, wherein the antibody binds to human CTLA-4; and a pharmaceutically acceptable excipient, wherein the composition contains a concentration of antibody that is about 20 mg/ml.

In one embodiment, the liquid pharmaceutical composition comprises from about 0.01 mg/ml to about 200 mg/ml of monoclonal anti-CTLA-4 antibody ticilimumab; and from about 0.3 micromolar to about 50 millimolar of chelating agent.

In another embodiment, the liquid pharmaceutical composition comprises from about 0.1 mg/ml to about 100 mg/ml of monoclonal anti-CTLA-4 antibody ticilimumab; and from about 3 micromolar to about 5.0 millimolar of chelating agent.

In another embodiment, the liquid pharmaceutical composition comprises from about 0.1 mg/ml to about 100 mg/ml of monoclonal anti-CTLA-4 antibody ticilimumab; and about 0.27 millimolar of chelating agent.

In another embodiment, the liquid pharmaceutical composition comprises from about 0.1 mg/ml to about 100 mg/ml of monoclonal anti-CTLA-4 antibody ticilimumab; and from about 0.3 micromolar to about 50 millimolar of EDTA.

In another embodiment, the liquid pharmaceutical composition comprises from about 0.1 mg/ml to about 100 mg/ml of monoclonal anti-CTLA-4 antibody ticilimumab; and from about 3 micromolar to about 10.0 millimolar of EDTA.

In another embodiment, the liquid pharmaceutical composition comprises from about 0.1 mg/ml to about 100 mg/ml of monoclonal anti-CTLA-4 antibody ticilimumab; and from about 0.1 millimolar to about 1.0 millimolar of EDTA.

In another embodiment, the liquid pharmaceutical composition comprises from about 0.1 mg/ml to about 100 mg/ml of monoclonal anti-CTLA-4 antibody ticilimumab; and about 0.27 millimolar of EDTA.

In another embodiment, the liquid pharmaceutical composition comprises from about 0.1 mg/ml to about 100 mg/ml of monoclonal anti-CTLA-4 antibody ticilimumab; and from about 3 micromolar to about 5.0 millimolar of DTPA.

In another embodiment, the liquid pharmaceutical composition comprises from about 0.1 mg/ml to about 100 mg/ml of monoclonal anti-CTLA-4 antibody ticilimumab; and from about 3 micromolar to about 5.0 millimolar of deferoxamine.

In one embodiment, the liquid pharmaceutical composition comprises from about 0.01 mg/ml to about 200 mg/ml of monoclonal anti-CTLA-4 antibody ticilimumab; and from about 1 mM to about 100 mM of histidine.

In another embodiment, the liquid pharmaceutical composition comprises from about 0.1 mg/ml to about 200 mg/ml of monoclonal anti-CTLA-4 antibody ticilimumab; from about 3 micromolar to about 5.0 millimolar of chelating agent; and from about 1 mM to about 100 mM of histidine.

In another embodiment, the liquid pharmaceutical composition comprises from about 0.1 mg/ml to about 200 mg/ml of monoclonal anti-CTLA-4 antibody ticilimumab; from about 3 micromolar to about 5.0 millimolar of chelating agent; and from about 10 millimolar to about 400 millimolar of trehalose.

In another embodiment, the liquid pharmaceutical composition comprises from about 0.1 mg/ml to about 200 mg/ml of monoclonal anti-CTLA-4 antibody ticilimumab; from about 3 micromolar to about 5.0 millimolar of chelating agent; from about 10 millimolar to about 400 millimolar of trehalose; and from about 1 mM to about 100 mM of histidine.

In another embodiment, the liquid pharmaceutical composition comprises from about 0.1 mg/ml to about 200 mg/ml of monoclonal anti-CTLA-4 antibody ticilimumab; from about 3 micromolar to about 5.0 millimolar of chelating agent; from about 10 millimolar to about 400 millimolar of trehalose; from about 1 mM to about 100 mM of histidine; and from about 0.005 millimolar to about 10 millimolar of polysorbate 80.

In another embodiment, the liquid pharmaceutical composition comprises from about 0.1 mg/ml to about 200 mg/ml of monoclonal anti-CTLA-4 antibody ticilimumab; from about 3 micromolar to about 5.0 millimolar of EDTA; from about 10 millimolar to about 400 millimolar of a tonicity agent; from about 1 mM to about 100 mM of a buffer; and from about 0.005 millimolar to about 10 millimolar of a surfactant.

In another embodiment, the liquid pharmaceutical composition comprises from about 0.1 mg/ml to about 200 mg/ml of monoclonal anti-CTLA-4 antibody ticilimumab; from about 3 micromolar to about 5.0 millimolar of EDTA; from about 10 millimolar to about 400 millimolar of a tonicity agent; from about 1 mM to about 100 mM of histidine; and from about 0.005 millimolar to about 10 millimolar of a surfactant.

In another embodiment, the liquid pharmaceutical composition comprises from about 0.1 mg/ml to about 200 mg/ml of monoclonal anti-CTLA-4 antibody ticilimumab; from about 3 micromolar to about 5.0 millimolar of EDTA; from about 10 millimolar to about 400 millimolar of trehalose; from about 1 mM to about 100 mM of histidine; and from about 0.005 millimolar to about 10 millimolar of a surfactant.

In certain aspects of the present invention, the liquid anti-CTLA-4 antibody compositions comprise from about 0.1 mg/ml to about 200 mg/ml of monoclonal anti-CTLA-4 antibody ticilimumab; from about 1 mM to about 100 mM of histidine; from about 0.005 millimolar to about 10 millimolar of polysorbate 80; from about 3 micromolar to about 5.0 millimolar of EDTA; and from about 10 millimolar to about 400 millimolar of trehalose.

In other aspects of the present invention, the liquid anti-CTLA-4 antibody compositions comprise from about 1.0 mg/ml to about 100 mg/ml of monoclonal anti-CTLA-4 antibody ticilimumab; from about 10 mM to about 50 mM of histidine; from about 0.01 millimolar to about 1.0 millimolar of polysorbate 80; from about 3 micromolar to about 5.0 millimolar of EDTA; and from about 100 millimolar to about 300 millimolar of trehalose.

In other aspects of the present invention, the liquid anti-CTLA-4 antibody compositions comprise from about 10 mg/ml to about 50 mg/ml of monoclonal anti-CTLA-4 antibody ticilimumab; from about 10 mM to about 30 mM of histidine; from about 0.05 millimolar to about 0.5 millimolar of polysorbate 80; from about 0.1 millimolar to about 1 millimolar of EDTA; and from about 200 millimolar to about 250 millimolar of trehalose.

In other aspects of the present invention, the liquid anti-CTLA-4 antibody compositions comprise about 20 mg/ml of monoclonal anti-CTLA-4 antibody ticilimumab; about 20 mM of histidine; about 0.15 millimolar of polysorbate 80; about 0.27 millimolar of EDTA; and about 222 millimolar of trehalose.

In another embodiment, the invention is directed to a stable liquid pharmaceutical composition comprising an anti-CTLA-4 antibody and a pharmaceutically acceptable chelating agent, wherein the molar concentration of the antibody ranges from about 0.0006 millimolar to about 1.35 millimolar and the molar concentration of the chelating agent ranges from about 0.003 millimolar to about 50 millimolar, and wherein the molar ratio of antibody to chelating agent ranges from about 0.00001 to about 450; from about 0.0001 to about 100; from about 0.005 to about 50; from about 0.001 to about 10; from about 0.01 to about 5; from about 0.1 to about 1; or is about 0.5.

In another embodiment, the invention is directed to a stable liquid pharmaceutical composition comprising ticilimumab and a pharmaceutically acceptable chelating agent, wherein the molar concentration of the antibody ranges from about 0.0006 millimolar to about 1.35 millimolar and the molar concentration of the chelating agent ranges from about 0.003 millimolar to about 50 millimolar, and wherein the molar ratio of antibody to chelating agent ranges from about 0.00001 to about 450; from about 0.0001 to about 100; from about 0.005 to about 50; from about 0.001 to about 10; from about 0.01 to about 5; from about 0.1 to about 1; or is about 0.5.

In another embodiment, the invention is directed to a stable liquid pharmaceutical composition comprising ticilimumab, a pharmaceutically acceptable chelating agent, and histidine; wherein the molar concentration of the antibody ranges from about 0.0006 millimolar to about 1.35 millimolar, the molar concentration of the chelating agent ranges from about 0.003 millimolar to about 50 millimolar, and the molar concentration of histidine ranges from about 1 millimolar to about 100 millimolar; and wherein the molar ratio of antibody to chelating agent ranges from about 0.00001 to about 450; from about 0.0001 to about 100; from about 0.005 to about 50; from about 0.001 to about 10; from about 0.01 to about 5; from about 0.1 to about 1; or is about 0.5.

In another embodiment, the invention is directed to a stable liquid pharmaceutical composition comprising ticilimumab, a pharmaceutically acceptable chelating agent, and histidine; wherein the molar concentration of the antibody ranges from about 0.0006 millimolar to about 1.35 millimolar, the molar concentration of the chelating agent ranges from about 0.003 millimolar to about 50 millimolar, and the molar concentration of histidine ranges from about 10 millimolar to about 50 millimolar; and wherein the molar ratio of antibody to chelating agent ranges from about 0.0001 to about 100; from about 0.005 to about 50; from about 0.001 to about 10; from about 0.01 to about 5; from about 0.1 to about 1; or is about 0.5.

In another embodiment, the invention is directed to a stable liquid pharmaceutical composition comprising ticilimumab, a pharmaceutically acceptable chelating agent, and histidine; wherein the molar concentration of the antibody ranges from about 0.0006 millimolar to about 1.35 millimolar, the molar concentration of the chelating agent ranges from about 0.003 millimolar to about 50 millimolar, and the molar concentration of histidine ranges from about 10 millimolar to about 30 millimolar; and wherein the molar ratio of antibody to chelating agent ranges from about 0.005 to about 50; from about 0.001 to about 10; from about 0.01 to about 5; from about 0.1 to about 1; or is about 0.5.

In another embodiment, the invention is directed to a stable liquid pharmaceutical composition comprising ticilimumab, a pharmaceutically acceptable chelating agent, and histidine; wherein the molar concentration of the antibody ranges from about 0.0006 millimolar to about 1.35 millimolar, the molar concentration of the chelating agent ranges from about 0.003 millimolar to about 50 millimolar, and the molar concentration of histidine ranges from about 10 millimolar to about 30 millimolar; and wherein the molar ratio of antibody to chelating agent ranges from about 0.001 to about 10; from about 0.01 to about 5; from about 0.1 to about 1; or is about 0.5.

In another embodiment, the invention is directed to a stable liquid pharmaceutical composition comprising ticilimumab, a pharmaceutically acceptable chelating agent, and histidine; wherein the molar concentration of the antibody ranges from about 0.0006 millimolar to about 1.35 millimolar, the molar concentration of the chelating agent ranges from about 0.003 millimolar to about 50 millimolar, and the molar concentration of histidine is about 20 millimolar; and wherein the molar ratio of antibody to chelating agent ranges from about 0.001 to about 10; from about 0.01 to about 5; from about 0.1 to about 1; or is about 0.5.

Methods of Producing Anti-CTLA-4 Antibodies and Antibody Producing Cell Lines:

Antibodies in accordance with the invention can be prepared through the utilization of a transgenic mouse that has a substantial portion of the human antibody producing genome inserted, but that is rendered deficient in the production of endogenous, murine, antibodies. Such mice, then, are capable of producing human immunoglobulin molecules and antibodies and are deficient in the production of murine immunoglobulin molecules and antibodies. Technologies utilized for achieving the same are discussed below.

It is possible to produce transgenic animals (e.g., mice) that are capable, upon immunization, of producing a full repertoire of human antibodies in the absence of endogenous immunoglobulin production. In particular, however, one embodiment of transgenic production of mice and antibodies therefrom is disclosed in U.S. Pat. No. 6,682,736 to Hanson, et al. Through use of such technology, antibodies that bind to CTLA-4 and hybridomas producing such antibodies can be prepared.

Human antibodies avoid potential problems associated with antibodies that possess murine or rat variable and/or constant regions. The presence of such murine or rat derived proteins can lead to the rapid clearance of the antibodies or can lead to the generation of an immune response against the antibody by a subject that receives administration of such antibodies.

For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen (e.g., CTLA-4) challenge. See, e.g., Jakobovits et al, *Proc. Natl. Acad. Sci. USA*, 90:2551 (1993); Jakobovits et al., *Nature,* 362: 255-258 (1993); Bruggermann et al., *Year in Immuno.,* 7:33 (1993); and Duchosal et al., *Nature* 355:258 (1992). Human antibodies can also be derived from phage-display libraries (Hoogenboom et al., *J. Mol. Biol.,* 227:381 (1991); Marks et al., *J. Mol. Biol.,* 222:581-597 (1991); Vaughan et al., *Nature Biotech* 14:309 (1996)).

In some embodiments, human anti-CTLA-4 antibodies can be produced by immunizing a non-human transgenic animal, e.g., XENOMOUSE™ mice, whose genome comprises human immunoglobulin genes so that the recombinant mouse produces human antibodies. XENOMOUSE™ mice are engineered mouse strains that comprise large fragments of human immunoglobulin heavy chain and light chain loci and are deficient in mouse antibody production. XENOMOUSE™ mice produce an adult-like human repertoire of fully human antibodies and generate antigen-specific human antibodies. In some embodiments, the XENOMOUSE™ mice contain approximately 80% of the human antibody V gene repertoire through introduction of megabase sized, germline configuration yeast artificial chromosome (YAC) fragments of the human heavy chain loci and kappa light chain loci. In other embodiments, XENOMOUSE™ mice further contain approximately all of the lambda light chain locus. See, e.g., Green et al., *Nature Genetics* 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763.

Therefore, in some embodiments, human antibodies can be produced by immunizing a non-human animal comprising in its genome some or all of human immunoglobulin heavy chain and light chain loci with a CTLA-4 antigen.

In some embodiments, the CTLA-4 antigen is isolated and/or purified CTLA-4. In a preferred embodiment, the CTLA-4 antigen is human CTLA-4. In some embodiments, the CTLA-4 antigen is a fragment of CTLA-4. In some embodiments, the CTLA-4 fragment comprises at least one epitope of CTLA-4. In other embodiments, the CTLA-4 antigen is a cell that expresses or overexpresses CTLA-4 or an immunogenic fragment thereof on its surface. In still other embodiments, the CTLA-4 antigen is a CTLA-4 fusion protein. CTLA-4 can be purified from natural sources using known techniques.

In a preferred embodiment, the non-human animal is a XENOMOUSE™ animal (Abgenix Inc., Fremont, Calif.). Another non-human animal that may be used is a transgenic mouse produced by Medarex (Medarex, Inc., Princeton, N.J.).

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994,619. In a preferred embodiment, the CTLA-4 antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule can involve two or more administrations of the polypeptide, spread out over several weeks.

After immunization of an animal with a CTLA-4 antigen, antibodies and/or antibody-producing cells can be obtained from the animal. In some embodiments, anti-CTLA-4 antibody-containing serum is obtained from the animal by bleeding or sacrificing the animal. The serum may be used as it is obtained from the animal, an immunoglobulin fraction may be obtained from the serum, or the anti-CTLA-4 antibodies may be purified from the serum.

In some embodiments, antibody-producing immortalized cell lines are prepared from cells isolated from the immunized animal. After immunization, the animal is sacrificed and lymph node and/or splenic B cells are immortalized. Methods of immortalizing cells include, but are not limited to, transfecting them with oncogenes, infecting them with an oncogenic virus, cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. In a preferred embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE™ animal and the myeloma cell line is a non-secretory mouse myeloma. In an even more preferred embodiment, the myeloma cell line is P3-X63-AG8-653. If fusion with myeloma cells is used, the myeloma cells preferably do not secrete immunoglobulin polypeptides (a non-secretory cell line). Immortalized cells are screened using CTLA-4, a portion thereof, or a cell expressing CTLA-4. In a preferred embodiment, the initial screening is performed using an enzyme-linked immunoassay (ELISA) or a radioimmunoassay. An example of ELISA screening is provided in WO 00/37504.

Anti-CTLA-4 antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

As will be appreciated, antibodies in accordance with the present invention can be recombinantly expressed in cell lines other than hybridoma cell lines. Nucleic acid sequences encoding the cDNAs or genomic clones for the particular antibodies can be used for transformation of a suitable mammalian or nonmammalian host cells.

The present invention also encompasses nucleic acid molecules encoding anti-CTLA-4 antibodies. In some embodiments, different nucleic acid molecules encode a heavy chain and a light chain of an anti-CTLA-4 immunoglobulin. In other embodiments, the same nucleic acid molecule encodes a heavy chain and a light chain of an anti-CTLA-4 immunoglobulin. In one embodiment, the nucleic acid encodes an anti-CTLA-4 antibody of the invention.

A nucleic acid molecule encoding the heavy or entire light chain of an anti-CTLA-4 antibody or portions thereof can be isolated from any source that produces such antibody. In various embodiments, the nucleic acid molecules are isolated from a B cell isolated from an animal immunized with anti-CTLA-4 or from an immortalized cell derived from such a B cell that expresses an anti-CTLA-4 antibody. Methods of isolating mRNA encoding an antibody are well-known in the art. See, e.g., Sambrook, et al., *Molecular Cloning* 3rd Ed. Vol. 3 (1989). The mRNA may be used to produce cDNA for use in the polymerase chain reaction (PCR) or cDNA cloning of antibody genes. In a preferred embodiment, the nucleic acid molecule is isolated from a hybridoma that has as one of its fusion partners a human immunoglobulin-producing cell from a non-human transgenic animal. In an even more preferred embodiment, the human immunoglobulin producing cell is isolated from a XENOMOUSE™ animal. In another embodiment, the human immunoglobulin-producing cell is from a non-human, non-mouse transgenic animal, as described above. In another embodiment, the nucleic acid is isolated from a non-human, non-transgenic animal. The nucleic acid molecules isolated from a non-human animal may be used, e.g., for humanized antibodies.

In some embodiments, a nucleic acid encoding a heavy chain of an anti-CTLA-4 antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-CTLA-4 antibody of the invention can comprise a polynucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and light ($V_L$) chains are "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain ($C_L$) constant domains, respectively, such that the $V_H$ segment is operatively linked to the $C_H$ segment(s) within the vector, and the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the art. See, e.g., Kabat et al., *Sequences of Proteins of Immunological Interest,* 5th Ed., NIH Publ. No. 91-3242, 1991. Nucleic acid molecules encoding the full-length heavy and/or light chains may then be expressed from a cell into which they have been introduced and the anti-CTLA-4 antibody isolated.

The present invention also provides vectors comprising nucleic acid molecules that encode the heavy chain of an anti-CTLA-4 antibody of the invention or an antigen-binding portion thereof. The invention also provides vectors comprising nucleic acid molecules that encode the light chain of such antibodies or antigen-binding portion thereof. The invention further provides vectors comprising nucleic acid molecules encoding fusion proteins, modified antibodies, antibody fragments, and probes thereof.

In some embodiments, the anti-CTLA-4 antibodies, or antigen-binding portions of the invention are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviruses (such as retroviral LTRs), cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062, U.S. Pat. No. 4,510,245 and U.S. Pat. No. 4,968,615. Methods for expressing antibodies in plants, including a description of promoters and vectors, as well as transformation of plants is known in the art. See, e.g., U.S. Pat. No. 6,517,529, herein incorporated by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in DHFR-host-cells with methotrexate selection/amplification), the neomycin resistance gene (for G418 selection), and the glutamine synthetase gene.

Nucleic acid molecules encoding anti-CTLA-4 antibodies and vectors comprising these nucleic acid molecules can be used for transformation of a suitable mammalian, plant, bacterial or yeast host cell. Antibodies of the invention can be produced transgenically-through the generation of a mammal or plant that is transgenic for the immunoglobulin heavy and light chain sequences of interest and production of the antibody in a recoverable form therefrom.

Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455. The transformation procedure used depends upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, NS0 cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. Site directed mutagenesis of the antibody CH2 domain to eliminate glycosylation may be preferred in order to prevent changes in either the immunogenicity, pharmacokinetic, and/or effector functions resulting from non-human glycosylation. The expression methods are selected by determining which system generates the highest expression levels and produce antibodies with constitutive CTLA-4 binding properties.

Further, expression of antibodies of the invention (or other moieties therefrom) from production cell lines can be enhanced using a number of known techniques. For example, the glutamine sythetase and DHFR gene expression systems are common approaches for enhancing expression under certain conditions. High expressing cell clones can be identified using conventional techniques, such as limited dilution cloning and Microdrop technology. The Glutamine Synthetase system is discussed in whole or part in connection with European Patent Nos. 0 216 846, 0 256 055, and 0 323 997 and European Patent Application No. 89303964.4.

In connection with the transgenic production in mammals, antibodies can also be produced in, and recovered from, the milk of goats, cows, or other mammals. See, e.g., U.S. Pat. Nos. 5,827,690, 5,756,687, 5,750,172, and 5,741,957.

The anti-CTLA-4 antibodies expressed in cell lines as described above may be purified and/or isolated from the associated cellular material. The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed. Current Protocols in Molecular Biology, Greene Publishing and Wiley Interscience, New York (1987).

In the present invention, it is possible that the anti-CTLA-4 antibodies of the present invention expressed by different cell lines or in transgenic animals will have different glycosylation patterns from each other. However, all of the anti-CTLA-4 antibodies encoded by the nucleic acids and amino acids provided herein are considered part of the instant invention, regardless of their glycosylation pattern or modification or deletion thereof. Thus, for purposes of the present invention, the anti-CLTA-4 antibodies may be glycosylated or non-glycosylated. When the anti-CTLA-4 antibodies are glycosylated they may have any possible glycosylation pattern. Moreover, each heavy chain within one antibody may have the same glycosylation pattern or the two heavy chains may have differing glycosylation patterns. Site directed mutagenesis of the antibody CH2 domain to eliminate glycosylation is also encompassed by the present invention in order to prevent changes in either the immunogenicity, pharmacokinetic, and/or effector functions resulting from non-human glycosylation.

As used herein, the term "glycosylation" means the pattern of carbohydrate units that are covalently attached to an antibody. When it is said that the anti-M-CTLA-4 antibodies herein have a particular glycosylation pattern, it is meant that the majority of the referenced anti-CTLA-4 antibodies have that particular glycosylation pattern. In other aspects, when it is said that the anti-M-CTLA-4 antibodies herein have a particular glycosylation pattern, it is meant that greater than or equal to 50%, 75%, 90%, 95%, 99% or 100% of the referenced anti-CTLA-4 antibodies have that particular glycosylation pattern.

The anti-CTLA-4 antibodies of the present invention also encompass glycosylation variants thereof (e.g., by insertion of a glycosylation site or deletion of any glycosylation site by deletion, insertion or substitution of suitable amino acid residues).

Glycosylation of polypeptides is typically either N-linked or O-linked. Glycosylation of antibody polypeptides is typically N-linked and forms a biantennary structure. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in an antibody creates a potential glycosylation site.

The three distinct structures of biantennary glycans are designated "G0", "G1" and "G2" having zero, one, or two, respectively, terminal galactose residues on the nonreducing end of the glycan. See Jefferis et al., *Biochem. J.*, 268, 529-537 (1990). In some cases, the glycan structure may also have a fucose residue linked to an N-acetylglucosamine, which is covalently bonded to the asparagine amino acid (e.g., position 297) found in the antibody. When the fucose (F) is present, the biantennary glycan nomenclature is changed to "G0F", "G1F", or "G2F" depending upon the number of terminal galactose residues. See Teillaud, *Expert Opin. Biol. Ther.,* 5(Suppl.1):S15-S27 (2005). Furthermore, when the antibody contains both of the two heavy chains, the glycan nomenclature is repeated for each of the two heavy chains. The "G0F,G0F" glycoform is a species in which both heavy chains have the G0 glycan attached and each G0 glycan has a fucose (F) residue linked to an N-acetylglucosamine. The "G0F,G1F" glycoform is a species in one of the heavy chains has the G0 glycan attached and the other heavy chain has the G1 glycan attached with each G0 glycan and G1 glycan having a fucose (F) residue linked to an N-acetylglucosamine.

In certain embodiments, the anti-CTLA-4 antibodies have a glycosylation pattern that is selected from the group consisting of "G0F,G0F"; "G0F,G1F"; "G1F,G1F"; "G1F, G2F"; and mixtures thereof. In other embodiments, the anti-CTLA-4 antibodies have a glycosylation pattern that is "G0F,G1F" for greater than 50% of the produced antibodies. In other embodiments, the anti-CTLA-4 antibodies have a glycosylation pattern that is "G0F,G0F" for less than 50% of the produced antibodies. For example, in one embodiment, the anti-CTLA-4 antibody 11.2.1 described herein has a glycosylation pattern of "G0F,G0F" or "G0F,G1F". In some embodiments, the anti-CTLA-4 antibodies (11.2.1) are produced having a mixture of different glycosylation patterns. For example, in a sample of the antibodies (11.2.1), there may be a mixture of antibodies (11.2.1) with some having a glycosylation pattern of "G0F,G1F" and others having a glycosylation pattern of "G0F,G0F" in a ratio of approximately 3:2, respectively.

Routes of Administration and Dosages:

The compositions of this invention may be in liquid solutions (e.g., injectable and infusible solutions). The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular, and intrasternally) or by infusion techniques, in the form of sterile injectable liquid or olageneous suspensions. As will be appreciated by the skilled artisan, the route and/or mode of administration will vary depending upon the desired results. In a preferred embodiment, the antibody is administered by intravenous infusion or injection. In another preferred embodiment, the antibody is administered by intramuscular or subcutaneous injection.

Therapeutic compositions typically are sterile and stable under the conditions of manufacture and storage.

The composition can be formulated as a solution, microemulsion, dispersion, or liposome. Sterile injectable solutions can be prepared by incorporating the anti-CTLA-4 antibody in the required amount in an appropriate diluent with one or a combination of ingredients enumerated above, as required, followed by sterilization (e.g., filter sterilization). Generally, dispersions are prepared by incorporating the active compound into a sterile vehicle that contains a basic dispersion medium and the required other ingredients from those enumerated above. Such suspensions may be formulated according to the known art using those suitable dispersing of wetting agents and suspending agents or other acceptable agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, n-3 polyunsaturated fatty acids may find use in the preparation of injectables.

In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants.

Prolonged absorption of injectable compositions can be brought about by including in the composition an agent that delays absorption, for example, monostearate salts and gelatin or by formulating the composition into prolonged absorption forms such as, depots, liposomes, polymeric microspheres, polymeric gels, and implants.

Other methods for administration of the antibodies described herein include dermal patches that release the medications directly into a subject's skin. Such patches can contain the antibodies of the present invention in an optionally buffered, liquid solution, dissolved and/or dispersed in an adhesive, or dispersed in a polymer.

Still other methods for administration of the antibodies described herein include liquid opthalmological drops for the eyes.

The antibody may be administered once, but more preferably is administered multiple times. For example, the antibody may be administered from once daily to once every six months or longer. The administering may be on a schedule such as three times daily, twice daily, once daily, once every two days, once every three days, once weekly, once every two weeks, once every month, once every two months, once every three months and once every six months.

The antibody may also be administered continuously via a minipump. The antibody may be administered at the site of the tumor or inflamed body part, into the tumor or inflamed body part or at a site distant from the site of the tumor or inflamed body part. The antibody may be administered once, at least twice or for at least the period of time until the condition is treated, palliated or cured. The antibody generally may be administered for as long as the tumor is present provided that the antibody causes the tumor or cancer to stop growing or to decrease in weight or volume or until the inflamed body part is healed. The antibody typically would be administered as part of a pharmaceutical composition as described supra.

The compositions of the invention may include a therapeutically effective amount or a prophylactically effective amount of an antibody or antigen-binding portion of the invention. In preparing the formulation, the therapeutically effective amount of the anti-CTLA-4 antibody present in the formulation can be determined, for example, by taking into account the desired dose volumes and mode(s) of administration, the nature and severity of the condition to be treated, and the age and size of the subject.

Exemplary, non-limiting dose ranges for administration of the pharmaceutical compositions of the present invention to a subject are from about 0.01 mg/kg to about 200 mg/kg (expressed in terms of milligrams (mg) of anti-CTLA-4 antibody administered per kilogram (kg) of subject weight), from about 0.1 mg/kg to about 100 mg/kg, from about 1.0 mg/kg to about 50 mg/kg, from about 5.0 mg/kg to about 20 mg/kg, or about 15 mg/kg. For purposes of the present invention, an average human subject weighs about 70 kg.

Ranges intermediate to any of the dosages cited herein, e.g., about 0.01 mg/kg-199 mg/kg, are also intended to be part of this invention. For example, ranges of values using a combination of any of the recited values as upper and/or lower limits are intended to be included.

Dosage regimens can also be adjusted to provide the optimum desired response (e.g., a therapeutic or prophylactic response) by administering several divided doses to a subject over time or the dose can be proportionally reduced or increased as indicated by the exigencies of the therapeutic situation. It is especially advantageous to formulate parenteral compositions in dosage unit form for ease of administration and uniformity of dosage.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the anti-CTLA-4 antibody or portion and the particular therapeutic or prophylactic effect to be achieved, and (b) the limitations inherent in the art of compounding such an antibody for the treatment of sensitivity in individuals.

The liquid formulations of the present invention can be prepared as unit dosage forms. For example, a unit dosage per vial may contain from 1 to 1000 milliliters (mls) of different concentrations of an anti-CTLA-4 antibody. In other embodiments, a unit dosage per vial may contain about 1 ml, 2 ml, 3 ml, 4 ml, 5 ml, 6 ml, 7 ml, 8 ml, 9 ml, 10 ml, 15 ml, 20 ml, 30 ml, 40 ml, 50 ml or 100 ml of different concentrations of an anti-CTLA-4 antibody. If necessary, these preparations can be adjusted to a desired concentration by adding a sterile diluent to each vial. The liquid formulations of the present invention can also be prepared as unit dosage forms in sterile bags or containers, which are suitable for connection to an intravenous administration line or catheter.

Stability Assessment:

The present invention comprises stable liquid pharmaceutical compositions comprising an anti-CTLA4 antibody as described herein and a pharmaceutically acceptable chelating agent. A stable composition is desirable to maintain or resist changes in, for example, product appearance and integrity (including physical or chemical degradation potentially leading to a reduction in biological activity). Various analytical techniques and indicators for measuring protein stability are reported in the literature and a number of these techniques and indicators are reviewed in *Peptide and Protein Drug Delivery*, 247-301, Vincent Lee Ed., Marcel Dekker, Inc., New York, N.Y., Pubs. (1991) and Jones, A. Adv. *Drug Delivery Rev.* 10: 29-90 (1993). In general, the liquid pharmaceutical compositions of the present invention exhibit improved stability when subjected to low storage temperatures over a period of time, and/or when subjected to one or more freeze/thaw cycles.

In one embodiment, the composition when stored at a temperature from about 2° C. to about 8° C. for at least about 12 months, preferably at least about 18 months and more preferably at least about 24 months, is more stable than an otherwise identical composition lacking the chelating agent that is stored under the same conditions for the same time.

In another embodiment, the composition when stored at a temperature from about 25° C. to about 30° C. for at least about 3 months, preferably at least 6 months, and more preferably at least about 12 months, is more stable than an otherwise identical composition lacking the chelating agent that is stored under the same conditions for the same time.

In another embodiment, the composition when stored at a temperature of about 40° C. for at least about 1 months, preferably at least about 2 months, and more preferably at least about 3 months is more stable than an otherwise identical composition lacking the chelating agent that is stored under the same conditions for the same time.

As used herein, the term "a freeze/thaw cycle" refers to techniques for using a liquid antibody sample after frozen storage, wherein the temperature of the sample is lowered to a temperature of 0° C. or lower in order to freeze the liquid sample, and then subjecting the sample to a temperature which will restore its liquid state for a sufficient period of time to permit use of the sample, followed by and return to frozen storage, preferably at a temperature of 0° C. or lower. As used herein, the term "frozen storage" refers to freezing and maintaining a previously liquid antibody sample at a temperature of 0° C. or below, and preferably −20° C. or lower.

In one embodiment, the composition when subjected to at least 1 freeze/thaw cycle, preferably at least 2 freeze/thaw cycles, more preferably at least 3 freeze/thaw cycles, still more preferably at least 4 freeze/thaw cycles, still more preferably at least 5 freeze/thaw cycles, and still more preferably at least 6 freeze/thaw cycles, is more stable than an otherwise identical composition lacking the chelating agent that is subjected to the same freeze/thaw conditions.

In another embodiment, the composition satisfies two or more of the following conditions:

(a) the composition when stored at a temperature from about 2° C. to about 8° C. for at least about 12 months, preferably at least about 18 months and more preferably at least about 24 months, is more stable than an otherwise identical composition lacking the chelating agent that is stored under the same conditions for the same time;

(b) the composition when stored at a temperature from about 25° C. to about 30° C. for at least about 3 months, preferably at least 6 months, and more preferably at least about 12 months, is more stable than an otherwise identical composition lacking the chelating agent that is stored under the same conditions for the same time;

(c) the composition when stored at a temperature of about 40° C. for at least about 1 months, preferably at least about 2 months, and more preferably at least about 3 months is more stable than an otherwise identical composition lacking the chelating agent that is stored under the same conditions for the same time; or (d) the composition when subjected to at least 1 freeze/thaw cycle, preferably at least 2 freeze/thaw cycles, more preferably at least 3 freeze/thaw cycles, still more preferably at least 4 freeze/thaw cycles, still more preferably at least 5 freeze/thaw cycles, and still more preferably at least 6 freeze/thaw cycles, is more stable than an otherwise identical composition lacking the chelating agent that is subjected to the same freeze/thaw conditions.

In another embodiment, the composition satisfies three or more of the conditions discussed immediately above.

For purposes of the present application, antibody aggregation, antibody fragmentation, and/or composition discoloration, for example, can be used as indicators of the stability of the composition. In general, the liquid pharmaceutical compositions of the present invention exhibit a lower level of at least one of antibody aggregation, antibody fragmentation and composition discoloration when subjected to one or more of the above-described storage or freeze/thaw conditions relative to otherwise identical compositions lacking the chelating agent that are subjected to the same conditions.

Protein aggregation in a liquid pharmaceutical composition can be measured by various methods known in the art. Such methods include gel filtration chromatography to separate proteins on the basis of their molecular weight. A "gel" is a matrix of water and a polymer, such as agarose or polymerized acrylamide. The present invention also encompasses the use of gel filtration HPLC (high performance liquid chromatography). Other recognized methods of measuring aggregation include cation exchange chromatography, which is the general liquid chromatographic technique of ion-exchange chromatography utilizing anion columns. The cations exchanged in the present invention are from the protein molecules. Since multivalent protein aggregates may have some multiple of the net charge of the single-chain antigen-binding protein, the aggregates can be retained more strongly, and may be separated from the single-chain molecules. A preferred cationic exchanger is a polyaspartic acid column. Thus, a monomeric protein can be readily distinguished from an aggregate. However, those of ordinary skill in the art will realize that aggregation assays of the invention are not limited to any particular type of chromatography column, so long as it is capable of separating the two forms of protein molecules.

Protein fragmentation in a liquid pharmaceutical composition can be measured by various methods known in the art. Such methods include, for example, size exclusion chromatography, ultraviolet detection (e.g., at 214 nanometers), SDS-PAGE and/or matrix-assisted laser desorption ionization/time-of-flight mass spectrometry (MALDI/TOF MS). Protein fragmentation resulting in a charge alteration (e.g., occurring as a result of deamidation) can be evaluated, for example, by ion-exchange chromatography or isoelectric focusing (IEF).

Composition discoloration generally can be measured by visual observation of the composition itself. The present liquid pharmaceutical compositions comprising a chelating agent generally reduce composition discoloration (e.g., pink or yellow) and/or maintain composition clarity (e.g., turbidity, cloudiness and/or particulate formation) relative to otherwise identical compositions that do not contain the chelating agent. For purposes of the present invention, the term "discoloration" refers to both changes in color (e.g., from clear and colorless to pink or yellow) and to changes in clarity (e.g., from clear and colorless to turbid, cloudy and/or having particulates). Composition discoloration generally can be measured using additional techniques such as by ultraviolet detection at 214 nanometers and/or by visual comparison against a standard color scale of the compositions with and without the chelating agent. See PhEur 5.0, 2005 Monograph 2.2.2.

In one embodiment, antibody aggregation is determined after the composition is subjected to at least one of the following conditions:

(a) the composition is stored at a temperature from about 2° C. to about 8° C. for at least about 12 months, preferably at least about 18 months and more preferably at least about 24 months;

(b) the composition is stored at a temperature from about 25° C. to about 30° C. for at least about 3 months, preferably at least 6 months, and more preferably at least about 12 months;

(c) the composition is stored at a temperature of about 40° C. for at least about 1 months, preferably at least about 2 months, and more preferably at least about 3 months; or (d) the composition is subjected to at least 1 freeze/thaw cycle, preferably at least 2 freeze/thaw cycles, more preferably at least 3 freeze/thaw cycles, still more preferably at least 4 freeze/thaw cycles, still more preferably at least 5 freeze/thaw cycles, and still more preferably at least 6 freeze/thaw cycles. Antibody aggregates are then chromatographically separated from the composition (e.g., using HPLC) and the extent of aggregation determined from the resulting chromatogram. The stable liquid pharmaceutical compositions of the present invention typically have an aggregate peak area on the chromatogram that is less than about 6%, less than about 5%, less than about 4%, less than about 3%, less than about 2%, or less than about 1.5% of the total peak area on the chromatogram. In one specific example of this technique for measuring aggregation, the composition is stored for 24 weeks at 40° C. and chromatographic separation is then conducted using SE-HPLC with ultraviolet detection at 214 nanometers. This technique was used to measure antibody aggregation in Example 11 where, for example, Formulation No. 37 (containing a chelating agent) exhibited an aggregate peak area on the chromatogram of about 1.1% while Formulation 26 (lacking a chelating agent) exhibited an aggregate peak area on the chromatogram of about 6.4%.

In general, the difference between the aggregate chromatogram peak area for a stable liquid pharmaceutical composition of the present invention and the aggregate chromatogram peak area for an otherwise identical composition lacking the chelating agent that is subjected to the same conditions is at least about 2%, at least about 3%, at least about 4%, or at least about 4.5%. For example, this difference between Formulation 37 (aggregate peak area on the chromatogram of about 1.1%) and Formulation 26 (aggregate peak area on the chromatogram of about 6.4%) tested in Example 11 as discussed above is about 5.3%.

In another embodiment, antibody fragmentation is determined after the composition is subjected to at least one of the following conditions:

(a) the composition is stored at a temperature from about 2° C. to about 8° C. for at least about 12 months, preferably at least about 18 months and more preferably at least about 24 months;

(b) the composition is stored at a temperature from about 25° C. to about 30° C. for at least about 3 months, preferably at least 6 months, and more preferably at least about 12 months;

(c) the composition is stored at a temperature of about 40° C. for at least about 1 months, preferably at least about 2 months, and more preferably at least about 3 months; or (d) the composition is subjected to at least 1 freeze/thaw cycle, preferably at least 2 freeze/thaw cycles, more preferably at least 3 freeze/thaw cycles, still more preferably at least 4 freeze/thaw cycles, still more preferably at least 5 freeze/thaw cycles, and still more preferably at least 6 freeze/thaw cycles. Antibody fragments are then chromatographically separated from the composition (e.g., using gel filtration) and the extent of fragmentation determined from the resulting chromatogram. The stable liquid pharmaceutical compositions of the present invention typically have a fragment band volume on the chromatogram that is less than about 9%, less than about 8%, less than about 7%, less than about 6%, less than about 5%, or less than about 4.5% of the total band volume on the chromatogram. In one specific example of this technique for measuring fragmentation, the composition is stored for 24 weeks at 40° C. and then chromatographed using reduced SDS-PAGE (rSDS-PAGE) with band volumes determined by scanning with either a Molecular Dynamics Personal Densitometer PDQC-90 or a Bio-Rad GS800 Imaging Densitometer. This technique was used to measure antibody fragmentation in Example 11 where, for example, Formulation No. 37 (containing a chelating agent) exhibited a fragment band volume on the chromatogram of about 4.5% while Formulation 26 (lacking a chelating agent) exhibited a fragment band volume on the chromatogram of about 10.1%.

In general, the difference between the fragment band volume for a stable liquid pharmaceutical composition of the present invention and the fragment band volume for an otherwise identical composition lacking the chelating agent that is subjected to the same conditions is at least about 2%, at least about 3%, at least about 4%, or at least about 5%. For example, this difference between Formulation 37 (fragment band volume on the chromatogram of about 4.5%) and Formulation 26 (fragment band volume on the chromatogram of about 10.1%) tested in Example 11 as discussed above is about 5.6%.

Methods of Treatment:

Any of the types of antibodies described herein may be used therapeutically. In a preferred embodiment, the anti-CTLA-4 antibody is a human antibody. In another preferred embodiment, the CTLA-4 is human and the subject is a human subject. In yet another preferred embodiment, the anti-CTLA-4 antibody is a human IgG2 antibody. Alternatively, the subject may be a mammal that expresses a CTLA-4 protein that the anti-CTLA-4 antibody cross-reacts with. The antibody may be administered to a non-human mammal expressing CTLA-4 with which the antibody cross-reacts (i.e., a primate) for veterinary purposes or as an animal model of human disease. Such animal models may be useful for evaluating the therapeutic efficacy of antibodies of this invention.

The present invention provides a method for the treatment of a neoplasia condition in a subject, comprising administering to the subject a liquid pharmaceutical composition comprising an anti-CTLA-4 antibody; and a chelating agent alone or in combination with other excipients chosen from a buffer, a tonicity agent, or a surfactant, and mixtures thereof. In further embodiments, the aforementioned subject is one that is in need of the prevention or treatment of a neoplasia condition.

In another embodiment, the present invention provides a method for the treatment of a neoplasia condition in a subject, comprising administering to the subject a liquid pharmaceutical composition comprising anti-CTLA-4 antibody ticilimumab; and pharmaceutically acceptable excipient comprising a chelating agent alone or in combination with other excipients chosen from a buffer, a tonicity agent, or a surfactant, and mixtures thereof.

Both of the terms, "neoplasia" and "neoplasia condition", refer to a "neoplasm" or tumor, which may be benign, premalignant, metastatic, or malignant. Also encompassed by the present invention are benign, premalignant, metastatic, or malignant neoplasias. Also encompassed by the present invention are benign, premalignant, metastatic, or malignant tumors. Thus, all of benign, premalignant, metastatic, or malignant neoplasia or tumors are encompassed by the present invention and may be referred to interchangeably, as neoplasia, neoplasms or neoplasia-related conditions. Tumors are generally known in the art to be a mass of neoplasia or "neoplastic" cells. Although, it is to be understood that even one neoplastic cell is considered, for purposes of the present invention to be a neoplasm or alternatively, neoplasia.

Neoplasia conditions that may be treated by an anti-CTLA-4 antibody of the invention can involve any tissue or organ, and include, but are not limited to bone, brain, lung, squamous cell, bladder, gastric, pancreatic, breast, head, neck, liver, renal, ovarian, prostate, colorectal, esophageal, gynecological (e.g., cervical and ovarian), nasopharynx, or thyroid cancers. Also encompassed by the term neoplasia conditions, are bone metastases, melanomas, lymphomas, leukemias, and multiple myelomas. In particular, the anti-CTLA-4 antibody formulations of the present invention are useful to treat cancers of the breast, prostate, colon and lung.

In other embodiments, the methods and compositions of the present invention encompass the prevention and treatment of the neoplasia conditions selected from the group consisting of acral lentiginous melanoma, actinic keratoses, adenocarcinoma, adenoid cycstic carcinoma, adenomas, familial adenomatous polyposis, familial polyps, colon polyps, polyps, adenosarcoma, adenosquamous carcinoma, adrenocortical carcinoma, AIDS-related lymphoma, anal cancer, astrocytic tumors, bartholin gland carcinoma, basal cell carcinoma, bile duct cancer, bladder cancer, brain stem glioma, brain tumors, breast cancer, bronchial gland carcinomas, capillary carcinoma, carcinoids, carcinoma, carcinoma of the fallopian tubes, carcinoma of the endometrium, carcinosarcoma, cavernous, central nervous system lymphoma, cerebral astrocytoma, cholangiocarcinoma, chondosarcoma, choriod plexus papilloma/carcinoma, clear cell carcinoma, skin cancer, brain cancer, colon cancer, colorectal cancer, cutaneous T-cell lymphoma, cystadenoma, endodermal sinus tumor, endometrial hyperplasia, endometrial stromal sarcoma, endometrioid adenocarcinoma, ependymal, epitheloid, esophageal cancer, Ewing's sarcoma, extragonadal germ cell tumor, fibrolamellar, focal nodular hyperplasia, gallbladder cancer, gastrinoma, germ cell tumors, gestational trophoblastic tumor, glioblastoma, glioma, glucagonoma, hemangiblastomas, hemangioendothelioma, hemangiomas, hepatic adenoma, hepatic adenomatosis, hepatocellular carcinoma, Hodgkin's lymphoma, hypopharyngeal cancer, hypothalamic and visual pathway glioma, insulinoma, intaepithelial neoplasia, interepithelial squamous cell neoplasia, intraocular melanoma, invasive squamous cell carcinoma, large cell carcinoma, islet cell carcinoma, Kaposi's sarcoma, kidney cancer, laryngeal cancer, leiomyosarcoma, lentigo maligna melanomas, leukemia-related conditions, lip and oral cavity cancer, liver cancer, lung cancer, lymphoma, malignant mesothelial tumors, malignant thymoma, medulloblastoma, medulloepithelioma, melanoma, meningeal, merkel cell carcinoma, mesothelial, metastatic carcinoma, mucoepidermoid carcinoma, multiple myeloma/plasma cell neoplasm, mycosis fungoides, myelodysplastic syndrome, myeloproliferative conditions, nasal cavity and paranasal sinus cancer, nasopharyngeal cancer, neuroblastoma, neuroepithelial adenocarcinoma nodular melanoma, neoplasms of the central nervous system (e.g., primary CNS lymphoma, spinal axis tumors, brain stem gliomas or pituitary adenomas), non-Hodgkin's lymphoma, oat cell carcinoma, oligodendroglial, oral cancer, oropharyngeal cancer, osteosarcoma, pancreatic polypeptide, ovarian cancer, ovarian germ cell tumor, pancreatic cancer, papillary serous adenocarcinoma, pineal cell, pituitary tumors, plasmacytoma, pseudosarcoma, pulmonary blastoma, parathyroid cancer, penile cancer, pheochromocytoma, pineal and supratentorial primitive neuroectodermal tumors, pituitary tumor, plasma cell neoplasm, pleuropulmonary blastoma, prostate cancer, rectal cancer, renal cell carcinoma, retinoblastoma, rhabdomyosarcoma, sarcoma, serous carcinoma, small cell carcinoma, small intestine cancer, soft tissue carcinomas, somatostatin-secreting tumor, squamous carcinoma, squamous cell carcinoma, submesothelial, superficial spreading melanoma, supratentorial primitive neuroectodermal tumors, thyroid cancer, undifferentiatied carcinoma, urethral cancer, uterine cancer, uveal melanoma, verrucous carcinoma, vaginal cancer, vipoma, vulvar cancer, Waldenstrom's macroglobulinemia, well differentiated carcinoma, and Wilm's tumor.

In a more preferred embodiment, the anti-CTLA-4 antibody is administered to a subject with breast cancer, prostate cancer, lung cancer or colon cancer. In an even more preferred embodiment, the method causes the cancer to stop proliferating abnormally, or not to increase in weight or volume or to decrease in weight or volume.

Articles of Manufacture:

In another embodiment of the invention, an article of manufacture is provided comprising a container, which holds the liquid pharmaceutical formulation comprising at least one of the monoclonal anti-CTLA-4 antibodies of the present invention in a formulation comprising a chelating agent alone or in combination with other pharmaceutically acceptable excipients, and optionally provides instructions for its use. Suitable containers include, for example, bottles, vials, bags and syringes. The container may be formed from a variety of materials such as glass or plastic. An exemplary container is a 3-20 cc single use glass vial. Alternatively, for a multidose formulation, the container may be a 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use, contraindications, and/or lists of potential side-effects.

The present invention also provides a kit for preparing a liquid composition of a stabilized antibody comprising a first container, comprising monoclonal anti-CTLA-4 antibody 11.2.1 in solution, and a second container comprising a sufficient amount of a chelating agent alone or in combination with other excipients in solution to stabilize the antibody.

The following examples describe embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples. In the examples, all percentages are given on a weight basis unless otherwise indicated. The skilled artisan will appreciate that the weight quantities and/or weight-to-volume ratios recited in the examples can be converted to moles and/or molarities using the art-recognized molecular weights of the recited ingredients. Weight quantities exemplified herein (e.g., grams) are for the volumes (e.g., of buffer solutions, antibody formulation, etc.) recited. The skilled artisan will appreciate that the weight quantities can be proportionally adjusted when different formulation volumes are desired.

Example 1

This Example shows the generation of hybridoma cell lines that produce anti-CTLA-4 antibodies as described in U.S. Pat. No. 6,682,736 to Hanson, et al.

Antibodies of the invention were prepared, selected, and assayed as follows:

Antigen Preparation: Three distinct immunogens were prepared for immunization of the XenoMouse™ mice: (i) a CTLA-4-IgG fusion protein, (ii) a CTLA-4 peptide, and (iii) 300.19 murine lymphoma cells transfected with a mutant of CTLA-4 (Y201V) that is constitutively expressed on the cell surface.

CTLA-4-IgG1 Fusion Protein:
Expression Vector Construction

The cDNA encoding the mature extracellular domain of CTLA-4 was PCR amplified from human thymus cDNA library (Clontech) using primers designed to the published sequence (Eur. J Immunol 18:1901-1905 (1988)). The fragment was directionally subcloned into pSR5, a Sindbis virus expression plasmid (InVitrogen), between the human oncostatin M signal peptide and human IgG gamma 1 (IgG1) CH1/CH2/CH3 domains. The fusion protein does not contain a hinge domain but contains cysteine 120 in the extracellular domain of CTLA-4 to form a covalent dimer. The resulting vector was called CTLA-4-IgG1/pSR5. The complete CTLA-4-IgG1 cDNA in the vector was sequence confirmed in both strands. The amino acid sequence the CTLA4-1 g protein is shown below. The mature extracellular domain for CD44 was PCR amplified from human lymphocyte library (Clontech) and subcloned into pSinRep5 to generate a control protein with the identical IgG1 tail.

OM-CTLA4-IgG1 Fusion Protein: SEQ ID NO:13

MGVLLTQRTLLSLVLALLFPSMASMAMHVAQPAVVLASSRGIASFVCEYA

SPGKATEVRVTVLRQADSQVTEVCAATYMMGNELTFLDDSICTGTSSGNQ

VNLTIQGLRAMDTGLYICKVELMYPPPYYLGIGNGTQIYVIDPEPCPDSD

LEGAPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPTPEE

KTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALH

NHYTQKSLSLSPGK
Underlined = signal peptide

The cDNAs for mature extracellular domain of CD28 were PCR amplified from human lymphocyte library (Clontech) and then subcloned into pCDM8 (J. Immunol. 151: 5261-71 (1993)) to produce a human IgG1 fusion protein containing both thrombin cleavage and hinge regions. Marmoset, Cynomologous, and Rhesus CTLA4 were cloned from mRNA isolated from PHA stimulated PBMCs using standard techniques of degenerate PCR. Sequencing demonstrated that rhesus and cynomologous amino acid sequence were identical with three differences from mature human CTLA4 extracellular domain (S13N, I17T and L105M). Marmoset demonstrated ten amino acid differences from the mature human CTLA4 extracellular domain (V21A, V33I, A41T, A51G, 541, S71F, Q75K, T88M, L105M and G106S). Site directed mutagenesis was used to make single point mutations of all amino acids different in marmoset CTLA4 to map amino acids important for interation of the antibodies with human CTLA4-IgG. Mutations of human and marmoset CTLA-IgG for epitope mapping were generated by matchmaker site-directed mutagenesis (Promega). The IgG fusion proteins were produced by transient transfection of Cos7 cells and purified using standard Protein A techniques. Mutant CTLA4-IgG proteins were evaluated for binding to antibodies by immunoblotting and using BIAcore analyses.

Recombinant Protein Expression/Purification

Recombinant sindbis virus was generated by electroporating (Gibco) Baby Hamster Kidney cells with SP6 in vitro transcribed CTLA-4-IgG1/pSR5 mRNA and DH-26S helper mRNA as described by InVitrogen. Forty eight hours later recombinant virus was harvested and titered for optimal protein expression in Chinese hamster ovary cells (CHO-K1). CHO-K1 cells were cultured in suspension in DMEM/F12 (Gibco) containing 10% heat-inactivated fetal bovine serum (Gibco), non-essential amino acids (Gibco), 4 mM glutamine (Gibco), penicillin/streptomycin (Gibco), 10 mM Hepes pH 7.5 (Gibco). To produce CTLA-4-IgG, the CHO-K1 cells were resuspended at $1\times10^7$ cells/ml in DMEM/F12 and incubated with sindbis virus for one hour at room temperature. Cells were then diluted to $1\times10^6$/ml in DMEM/F12 containing 1% fetal bovine serum depleted of bovine IgG using Protein A Sepharose (Pharmacia), non-essential amino acids, 4 mM glutamine, 12.5 mM Hepes pH 7.5, and penicillin/streptomycin. Forty eight hours post-infection cells were pelleted and conditioned media was harvested and supplemented with complete protease inhibitor tablets (Boehringer Mannheim), pH adjusted to 7.5, and filtered 0.2μ, (Nalgene). FPLC (Pharmacia) was used to affinity purify the fusion protein using a 5 ml protein A HiTrap column (Pharmacia) at a 10 ml/min flow rate. The column was washed with 30 bed volumes of PBS and eluted with 0.1M glycine/HCl pH 2.8 at 1 ml/min. Fractions (1 ml) were immediately neutralized to pH 7.5 with Tris pH 9. The fractions containing CTLA-4-IgG1 were identified by SDS-PAGE and then concentrated using CENTRIPLUS® 50 (Amicon®) before applying to sepharose 200 column (Pharmacia) at 1 ml/min using PBS as the solvent. Fractions containing CTLA-4-IgG1 were pooled, sterile filtered 0.2μ. (Millipore), aliquoted and frozen at −80°. CD44-IgG1 was expressed and purified using the same methods. CD28-IgG was purified from conditioned media from transiently transfected Cos7 cells.

Characterization CTLA-4-IgG1:

The purified CTLA-4-IgG1 migrated as a single band on SDS-PAGE using colloidal coomassie staining (Novex). Under non-reducing conditions CTLA-4-IgG1 was a dimer (100 kDa), that reduced to a 50 kDa monomer when treated with 50 mM DTT. Amino acid sequencing of the purified CTLA-4-IgG1 in solution confirmed the N-terminus of CTLA-4 (MHVAQPAVVLAS) (SEQ ID NO:14) and that the oncostatin-M signal peptide was cleaved from the mature fusion protein. The CTLA-4-IgG1 bound to immobilized B7.1-IgG in a concentration dependent manner and the binding was blocked by a hamster-anti-human anti-CTLA-4 antibody (BNI3: PharMingen). The sterile CTLA-4-IgG was endotoxin free and quantitated by OD280 using 1.4 as the extinction coefficient. The yield of purified CTLA-4-IgG ranged between 0.5-3 mgs/liter of CHO-K1 cells.

CTLA-4 Peptide:

The following CTLA-4 peptide (SEQ ID NO:15) was prepared as described below:

NH$_2$: MHVAQPAVVLASSRGIASFVCEYASPGKATEVRVTVLRQADSQVT

EVCAATYMMGNELTFLDDSICTGTSSGNQ VNLTIQGLRAMDTGLYICKV

ELMYPPPYYLGIGNGTQIYVIDPEPC-CONH$_2$

Abbreviations/Materials:

NMP, N-Methylpyrrolidinone; TFE, 2,2,2-Trifluoroethanol; DCM, Dichloromethane; FMOC, Fluorenyl Methoxycarbonyl. All reagents were supplied by Perkin Elmer, with the following exceptions: TFE, Aldrich Chemical, FMOC-PAL-PEG resin, Perseptive Biosystems. Fmoc-Arg(PMC)-OH; FMOC-Asn(Trt)-OH, FMOC-Asp(tBu)-OH, FMOC-Cys(Trt)-OH, FMOC-Glu(tBu)-OH, FMOC-Gln(Trt)-OH, FMOC-His(Boc)-OH, FMOC-Lys(BOC)-OH, FMOC-Ser (tBu)-OH, FMOC-Thr(tBu)-OH and FMOC-Tyr(tBu)-OH were used for those amino acids requiring side chain protecting groups.

Peptide Synthesis:

Peptide synthesis was performed on a Perkin-Elmer 431A, retrofitted with feedback monitoring via UV absorbance at 301 nm (Perkin-Elmer Model 759A detector). The peptide sequence was assembled on a FMOC-PAL-PEG resin using conditional double coupling cycles. Forced double couplings were performed at cycles 10, 11, 18, 19, 20 and 28 through 33. The resin was washed with a 50% mixture of DCM and TFE at the completion of each acylation cycle, followed by capping of unreacted amino groups with acetic anhydride in NMP Resin was removed from the reactor after completing cycle 49 and the remainder continued to completion. Peptide cleavage from the resin was performed using Reagent K (King et al. *International Journal of Protein and Peptide Research* 36:255-266 (1990)) for 6 hours on 415 mg of resin affording 186 mg crude CTLA-4 peptide.

Peptide Characterization:

25 mg aliquots of the crude CTLA-4 peptide were dissolved in 5 ml 6M Guanidine HCl/100 mM K$_2$PO$_3$ at pH6.4 and eluted over a Pharmacia Hi Load Superdex 75 16/60 column (16 mm×600 mm, 120 ml bed volume) with 2M Guanidine HCl/100 mM K$_2$PO$_3$ at pH 6.4 at 2 ml/min for 180 minutes collecting 5 ml fractions. The fractions were analyzed by loading 1.7 μl of fractions onto a NuPAGE Laemeli gel running with MES running buffer and visualizing via Daichii silver stain protocol. Those fractions exhibiting a molecular weight of 12 KDa, as judged versus molecular weight standards, were pooled together and stored at 4° C. The combined fractions were analyzed by UV and gel electrophoresis. Amino acid sequencing was performed by absorbing a 100 microliter sample in a ProSorb cartridge (absorbed onto a PVDF membrane) and washing to remove the buffer salts. Sequencing was performed on an Applied Biosystems 420 sequencer. The expected N-terminal sequence (MHVAQPAVVLA) (SEQ ID NO:16) was observed. Immunoblotting demonstrated that the peptide was recognized by the BNI3 anti-human CTLA-4 antibody (PharMingen). To desalt, an aliquot containing 648 μg of material was placed in 3500 Da MWCO dialysis tubing and dialyzed against 0.1% TFA/H20 at 4° C. for 9 days with stirring. The entire contents of the dialysis bag was lyophilized to a powder.

"300.19" Cells Transfected with CTLA-4 (Y201V) Peptide Antigen:

The full length CTLA-4 cDNA was PCR amplified from human thymus cDNA library (Stratagene) and subcloned into pIRESneo (Clontech). A mutation of CTLA-4 that results in constitutive cell surface expression was introduced using MatchMaker Mutagenesis System (Promega). Mutation of tyrosine, Y201 to valine inhibits binding of the adaptin protein AP50 that is responsible for the rapid internalization of CTLA-4 (Chuang, et al. *J. Immunol.* 159:144-151 (1997)). Mycoplasma-free 300.19 murine lymphoma cells were cultured in RPMI-1640 containing 10% fetal calf serum, non-essential amino acids, penicillin/streptomycin, 2 mM glutamine, 12.5 mM Hepes pH 7.5, and 25 μM beta-mercaptoethanol. Cells were electroporated (3×10$^6$/0.4 ml serum free RPMI) in a 1 ml chamber with 20 ug CTLA-4-Y201V/pIRESneo using 200V/1180 uF (Gibco CellPorator). Cells were rested for 10 minutes and then 8 mls of pre-warmed complete RPMI media. At 48 hours cells were diluted to 0.5×10$^6$/ml in complete RPMI media containing 1 mg/ml G418 (Gibco). Resistant cells were expanded and shown to express CTLA-4 on the cell surface using the BNI3 antibody conjugated with phycoerythrin (PharMingen). High level expressing cells were isolated by sterile sorting.

Immunization and Hybridoma Generation:

XenoMouse™ mice (8 to 10 weeks old) were immunized (i) subcutaneously at the base of tails with 1×10$^7$ 300.19 cells that were transfected to express CTLA-4 as described above, resuspended in phosphate buffered saline (PBS) with complete Freund's adjuvant, or (ii) subcutaneously at the base of tail with (a) 10 μg the CTLA-4 fusion protein or (b) 10 μg CTLA-4 peptide, emulsified with complete Freund's adjuvant. In each case, the dose was repeated three or four times in incomplete Freund's adjuvant. Four days before fusion, the mice received a final injection of the immunogen or cells in PBS. Spleen and/or lymph node lymphocytes from immunized mice were fused with the [murine non-secretory myeloma P3 cell line] and were subjected to HAT selection as previously described (Galfre, G. and Milstein, C., "Preparation of monoclonal antibodies: strategies and procedures." *Methods Enzymol.* 73:3-46 (1981)). A large panel of hybridomas all secreting CTLA-4 specific human IgG$_2$K antibodies were recovered.

The following hybridoma producing anti-CTLA-4 antibodies designated as follows were deposited at the American Type Culture Collection, 10801 University Blvd. Manassas, Va. 20110-2209, on Apr. 29, 2003:

| Clone  | Subclone | ATCC Deposit No. |
| ------ | -------- | ---------------- |
| 11.2.1 | 11.2.1.4 | PTA-5169         |
| 4.1.1  | 4.1.1.1  | PTA-5166         |

Example 2

This Example shows the generation of recombinant mammalian cell lines that produce anti-CTLA-4 antibodies.

DNA encoding the heavy and light chains of monoclonal antibody 11.2.1 was cloned from the respective hybridoma cell line 11.2.1 and the DNA sequences were determined by methods known to one skilled in the art. From nucleic acid sequence and predicted amino acid sequence of the antibody 11.2.1, the identity of the gene usage for each antibody chain was determined.

The 11.2.1 DNA sequence inserts were then subcloned into expression vectors. The expression vectors were subsequently transfected into a mouse myeloma (NSO) host cell to generate various primary transfectant cell lines that produce anti-CTLA antibodies. A lead cell line was chosen based on growth and productivity analysis. The lead line was later sub-cloned to generate a clonal cell line.

The anti-CTLA4 antibody was produced by cell cultivation using the cell line in a bioreactor containing cell culture media. The media is supplement with nutrients during production. After harvest criteria were attained, the bioreactor was harvested either by filtration alone or by centrifugation followed by filtration. The clarified supernatant was then purified with three chromatographic steps comprising a Protein A affinity column and two ion exchange columns. A low pH inactivation and a viral filtration were also done to clear any potential viruses in the process. The product is concentrated and diafiltered into the formulation buffer to make the drug substance.

Example 3

A study was conducted to evaluate the effect of four different buffers on antibody aggregation and fragmentation.

Specifically, four liquid formulations comprising anti-CTLA4 antibody 11.2.1 and buffered with acetate, succinate, histidine or EDTA were prepared. The formulations then were stored at 40° C. and antibody aggregation and fragmentation measurements were taken at 0, 2, 5 and 7 weeks.

Preparation of Buffer Solutions:

Four buffer solutions were prepared as described in Table 3. Each solution was prepared by first dissolving an amount of the buffer species (listed in Table 3) in water (approximately 80% of target). The pH of each buffer solution was then adjusted to 5.5 by addition of a sufficient amount of the acid or base solution noted in Table 3. After adjustment of the pH, an additional amount of water was added to provide a final buffer concentration of 20 mM. The buffer concentration of 20 mM was selected to ensure reasonable pH stability at the selected pH of 5.5. The buffer solution was then filtered through a sterilization filter (0.22 micron pore size) into a sterilized receptacle for subsequent use.

TABLE 3

| Buffer Solutions: | | | |
| --- | --- | --- | --- |
| Buffer Type | Buffer Species | Buffer Concentration (g/L) | Acid/Base Solution |
| Acetate | Sodium acetate trihydrate | 2.74 | 1% v/v Glacial Acetic Acid |
| Succinate | Succinic acid | 2.36 | 1 M NaOH |
| Histidine | L-Histidine HCl monohydrate | 4.19 | 1 M NaOH |
| EDTA | Disodium EDTA dihydrate | 7.45 | 5 M HCl |

The 1% v/v glacial acetic acid solution was prepared by appropriate dilution (1 ml to 100 ml) of glacial acetic acid (99.9%) with water. The 1 molar (M) sodium hydroxide solution was prepared by dissolving 40 g of solid sodium hydroxide in 1 L of water. The 5 molar (M) hydrochloric acid solution was prepared by appropriate dilution of concentrated hydrochloric acid (37.8%) with water.

Preparation of Antibody Formulations:

The antibody formulations that were evaluated are listed in Table 4 below. To prepare each formulation, an amount of the tonicifier (reported in mg/ml in Table 4) was first added to the indicated buffer solution and the solution stirred until the tonicifier dissolved. An antibody bulk solution from the purification process described in Example 2 was obtained at 13.2 mg/mL in 20 mM sodium acetate buffer pH 5.5+140 mM sodium chloride. Buffer exchanges of this bulk solution into the above identified formulation solutions were carried out with Amicon® Ultra 15 MWCO10K (UFC901024) Centrifugal concentrators on a Beckman Coulter Allegra™ 21R Centrifuge run at 6500 RPM at 5° C. Approximately 8 volume exchanges were made and the antibody solution concentrated to between 27 and 30 mg/ml. Approximately 3 to 4 mls of formulations 1 through 18 were prepared. Antibody concentrations were determined by Ultraviolet-Visible spectrometry (UV-Vis) method using an extinction coefficient of 1.43 (mg/ml)$^{-1}$ cm$^{-1}$ at 280 nm.

A 20 mg/ml polysorbate 80 (PS80) solution was prepared by dilution and dissolution of polysorbate 80 by the appropriate formulation buffer prepared as described above. The polysorbate 80 was then added to the antibody and buffer solutions as a 20 mg/ml concentrate along with appropriate amount of buffer, antibody, tonicifier and water to obtain a 20 mg/ml final solution of the anti-CTLA-4 monoclonal antibody in the formulation corresponding to the compositions in Table 4 below.

For Formulation No. 2 in Table 4, the PEG3350 was added as a 200 mg/ml concentrate at this point.

The formulations were then filtered through 0.2μ sterilizing grade filters and filled into vials. A fill-volume of 0.5 to 1 ml was used in 2 ml Type 1 glass vials. The vials were closed with Daikyo 777-1 Fluorotec® coated stoppers, crimp sealed, and placed in stability chambers stored upright at 40° C. for 2, 5 and 7 weeks. The vials were washed and autoclaved, as were the 13 mm Daikyo 777-1 serum stoppers. Duplicate vials were immediately analyzed for levels of aggregation and fragmentation.

TABLE 4

Antibody Formulations Tested:

| Formulation No. | Buffer Type 20 mM, pH 5.5 | Tonicifier (mg/ml) | Surfactant (mg/ml) |
|---|---|---|---|
| 1 | Acetate | NaCl (9) | PS80 (0.2) |
| 2 | Acetate | NaCl (9) + PEG3350 (10) | PS80 (0.2) |
| 3 | Acetate | Sucrose (90) | PS80 (0.2) |
| 4 | Acetate | Sorbitol (48) | PS80 (0.2) |
| 5 | Acetate | Inositol (48) | PS80 (0.2) |
| 6 | Acetate | Mannitol (41) + Glycine (2) | PS80 (0.2) |
| 7 | Succinate | Sucrose (90) | PS80 (0.2) |
| 8 | Succinate | Sorbitol (48) | PS80 (0.2) |
| 9 | Succinate | Inositol (48) | PS80 (0.2) |
| 10 | Succinate | Mannitol (41) + Glycine (2) | PS80 (0.2) |
| 11 | Histidine | Sucrose (90) | PS80 (0.2) |
| 12 | Histidine | Sorbitol (48) | PS80 (0.2) |
| 13 | Histidine | Inositol (48) | PS80 (0.2) |
| 14 | Histidine | Mannitol (41) + Glycine (2) | PS80 (0.2) |
| 15 | EDTA | Sucrose (90) | PS80 (0.2) |
| 16 | EDTA | Sorbitol (48) | PS80 (0.2) |
| 17 | EDTA | Inositol (48) | PS80 (0.2) |
| 18 | EDTA | Mannitol (41) + Glycine (2) | PS80 (0.2) |

Aggregation Analysis:

The antibody formulations of Table 4 were stored at a temperature of 40° C. At weeks 0, 2, 5 and 7, each formulation was analyzed for aggregation using size exclusion chromatography (SEC). The size exclusion chromatography was carried out using a TSK gel G3000SWXL-G2000SWXL column, mobile phase 0.2 M sodium phosphate buffer at pH 7.0, a flow rate of 1 ml/min, and UV detection at 214 nm. FIG. 1 shows the percentage of eluted high molecular weight species (i.e., aggregates of anti-CTLA-4 monoclonal antibody 11.2.1) measured at the relevant times for each of the formulations. Aggregation levels were calculated by integrating the areas under the chromatogram peaks for each formulation and reporting the integrated areas under the high molecular weight species peaks as a percentage of total peak area (see FIG. 1). As can be seen in FIG. 1, the EDTA-buffered formulations showed the lowest levels of aggregation, followed by the histidine-, acetate-, and succinate-buffered formulations, in that order.

Figure 2:
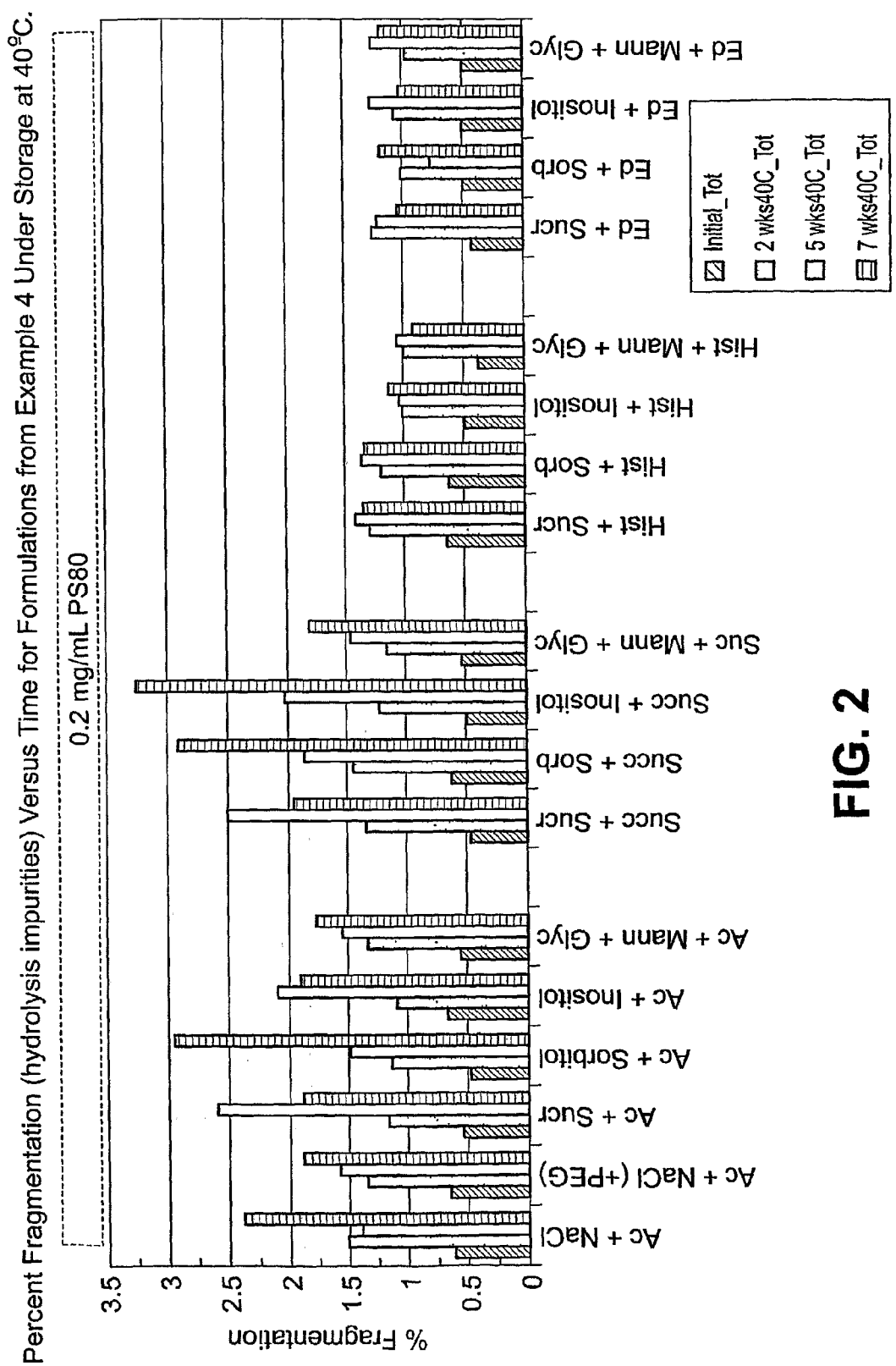
FIG. 2 is a bar graph that shows the percent total (hydrolytic) impurities formation in various test formulations after storage at 40° C. for up to 7 weeks by reduced SDSPAGE (rSDSPAGE)

Fragmentation Analysis:

As noted above, the antibody formulations of Table 4 were stored at a temperature of 40° C. At weeks 0, 2, 5 and 7, each formulation also was analyzed for fragmentation using rSDS-PAGE. The rSDS-PAGE analysis was carried out using NuPAGE® 4 to 12% bis-Tris gel and colloidal blue (Coomassie) stain. For the reduced gels (rSDS-PAGE), reduction was achieved by NuPAGE® reducing agent. Total hydrolytic impurities (i.e., fragments of anti-CTLA-4 monoclonal antibody 11.2.1) were estimated by scanning using either a Molecular Dynamics Personal Densitometer PDQC-90 or a Bio-Rad GS800™ Imaging Densitometer. FIG. 2 shows the percentage of fragmentation measured at the relevant times for each of the formulations. The fragmentation levels were calculated as a percentage of total band volume (see FIG. 2). As can be seen in FIG. 2, the EDTA-buffered formulations showed the lowest levels of fragmentation, followed by the histidine-, acetate-, and succinate-buffered formulations, in that order.

Table 5(a) (0 weeks), Table 5(b) (2 weeks), Table 5(c) (5 weeks), and Table 5(d) (7 weeks) below report the aggregation and fragmentation data that is graphically presented in FIGS. 1 and 2.

TABLE 5(a)

Aggregation and Fragmentation Results at 0 Time Point:

| Formulation No. | Percent Aggregation | Percent Fragmentation |
|---|---|---|
| 1 | 0.4% | 0.62% |
| 2 | 0.4% | 0.66% |
| 3 | 0.3% | 0.53% |
| 4 | 0.4% | 0.49% |
| 5 | 0.4% | 0.67% |
| 6 | 0.3% | 0.56% |
| 7 | 0.3% | 0.46% |
| 8 | 0.4% | 0.62% |
| 9 | 0.4% | 0.49% |
| 10 | 0.3% | 0.51% |
| 11 | 0.3% | 0.64% |
| 12 | 0.3% | 0.62% |
| 13 | 0.3% | 0.47% |
| 14 | 0.3% | 0.37% |
| 15 | 0.3% | 0.42% |
| 16 | 0.3% | 0.50% |
| 17 | 0.3% | 0.49% |
| 18 | 0.3% | 0.47% |

TABLE 5(b)

Aggregation and Fragmentation Results at 2 Week Time Point:

| Formulation No. | Percent Aggregation | Percent Fragmentation |
|---|---|---|
| 1 | 0.7% | 1.52% |
| 2 | 0.7% | 1.35% |
| 3 | 0.5% | 1.16% |
| 4 | 0.5% | 1.13% |
| 5 | 0.5% | 1.10% |
| 6 | 0.4% | 1.34% |
| 7 | 0.6% | 1.34% |
| 8 | 0.6% | 1.44% |
| 9 | 0.6% | 1.22% |
| 10 | 0.5% | 1.16% |
| 11 | 0.4% | 1.29% |
| 12 | 0.4% | 1.19% |
| 13 | 0.4% | 1.00% |
| 14 | 0.4% | 0.99% |
| 15 | 0.5% | 1.24% |
| 16 | 0.5% | 1.00% |
| 17 | 0.5% | 1.07% |
| 18 | 0.5% | 0.96% |

TABLE 5(c)

Aggregation and Fragmentation Results at 5 Week Time Point:

| Formulation No. | Percent Aggregation | Percent Fragmentation |
|---|---|---|
| 1 | 0.8% | 1.40% |
| 2 | 0.9% | 1.59% |
| 3 | 1.2% | 2.61% |
| 4 | 1.1% | 1.49% |
| 5 | 1.0% | 2.12% |
| 6 | 0.6% | 1.56% |
| 7 | 1.7% | 2.50% |
| 8 | 1.4% | 1.86% |
| 9 | 1.4% | 2.03% |
| 10 | 0.9% | 1.46% |
| 11 | 0.6% | 1.42% |
| 12 | 0.7% | 1.36% |
| 13 | 0.6% | 1.03% |
| 14 | 0.5% | 1.05% |
| 15 | 0.5% | 1.21% |
| 16 | 0.5% | 0.78% |

TABLE 5(c)-continued

Aggregation and Fragmentation Results at 5 Week Time Point:

| Formulation No. | Percent Aggregation | Percent Fragmentation |
|---|---|---|
| 17 | 0.6% | 1.27% |
| 18 | 0.5% | 1.25% |

TABLE 5(d)

Aggregation and Fragmentation Result at 7 Week Time Point:

| Formulation No. | Percent Aggregation | Percent Fragmentation |
|---|---|---|
| 1 | 1.4% | 2.39% |
| 2 | 1.2% | 1.90% |
| 3 | 1.4% | 1.89% |
| 4 | 1.8% | 2.96% |
| 5 | 1.3% | 1.92% |
| 6 | 1.1% | 1.77% |
| 7 | 1.2% | 1.97% |
| 8 | 2.2% | 2.91% |
| 9 | 2.4% | 3.25% |
| 10 | 1.3% | 1.82% |
| 11 | 0.9% | 1.34% |
| 12 | 0.9% | 1.33% |
| 13 | 0.7% | 1.12% |
| 14 | 0.6% | 0.92% |
| 15 | 0.6% | 1.04% |
| 16 | 0.6% | 1.18% |
| 17 | 0.6% | 1.01% |
| 18 | 0.6% | 1.18% |

Example 4

A study was conducted to evaluate the ability of different liquid formulations comprising monoclonal anti-CTLA-4 antibody 11.2.1 to tolerate multiple freezing and thawing cycles.

The ability of A liquid formulation to withstand multiple freeze/thaw cycles is often evaluated to determine whether the formulation may be stored (and, if desired, transported) frozen and then thawed for later use.

The formulations that were evaluated are listed in Table 6 below. The procedure used to prepare the formulations is the same as the one described in Example 3. 2.5 mL of each solution was placed in 5-mL type 1 glass vials, stoppered, and sealed. The formulations identified below as numbers 1 to 4, 7 to 8, 11 to 12, and 15 to 16 were identical to the formulations having the same number identifiers in Example 3.

TABLE 6

Antibody Formulations Tested:

| Formulation No. | Buffer Type 20 mM, pH 5.5 | Tonicifier (mg/ml) | Surfactant (mg/ml) |
|---|---|---|---|
| 1 | Acetate | NaCl (9) | PS80 (0.2) |
| 2 | Acetate | NaCl (9) + PEG3350 (10) | PS80 (0.2) |
| 3 | Acetate | Sucrose (90) | PS80 (0.2) |
| 4 | Acetate | Sorbitol (48) | PS80 (0.2) |
| 19 | Acetate | Trehalose (90) | PS80 (0.2) |
| 20 | Succinate | NaCl (9) | PS80 (0.2) |
| 21 | Succinate | NaCl (9) + PEG3350 (10) | PS80 (0.2) |
| 7 | Succinate | Sucrose (90) | PS80 (0.2) |
| 8 | Succinate | Sorbitol (48) | PS80 (0.2) |
| 22 | Histidine | NaCl (9) | PS80 (0.2) |
| 23 | Histidine | NaCl (9) + PEG3350 (10) | PS80 (0.2) |
| 11 | Histidine | Sucrose (90) | PS80 (0.2) |
| 12 | Histidine | Sorbitol (48) | PS80 (0.2) |
| 24 | EDTA | NaCl (9) | PS80 (0.2) |
| 25 | EDTA | NaCl (9) + PEG3350 (10) | PS80 (0.2) |
| 15 | EDTA | Sucrose (90) | PS80 (0.2) |
| 16 | EDTA | Sorbitol (48) | PS80 (0.2) |

Each formulation was subjected to six consecutive freeze/thaw cycles. The first three cycles were carried out in a controlled rate freezer. The last three cycles were slower cycles carried out with a number of water-filled vials to correspond to a high thermal load placed in a freezer or refrigerator. For cycles 1, 2 and 3, the vials containing the formulations were placed in a controlled rate freezer (Planer Kryo 560-16) and subjected to the following cycle: cool the formulation at a rate of 0.2° C./min until a temperature of −70° C. is reached, hold at −70° C. for 1.5 to 3 hours, and thaw the formulation at a rate of 0.3° C./min until a temperature of 5° C. is reached. For cycles 4, 5 and 6, the vials were placed in a box along with other water-filled vials none sample vial for each formulation; 17 formulation vials with a total of about 30 water-filed vials). This box was then placed first in a freezer maintained at a temperature of −70° C. freezer for approximately 17 hours, and then placed in a refrigerator maintained at a temperature of 2-8° C. for approximately 50 hours. A recording thermal probe placed in the box measured an average cooling rate of 0.09° C./min for the freeze process and an average heating rate of 0.03° C./min for the thaw process.

Each formulation was visually evaluated after each freeze/thaw cycle for particulate formation, color change and turbidity change. Such visual observations of each formulation were performed in a light box against black and white backgrounds while the formulation was still cold after each thaw. Table 7 (below) reports the results.

TABLE 7

Visual Evaluations of Freeze/thaw Stability of Anti-CTLA-4 antibody 11.2.1

| No. | ID | 1xFT | 2xFT | 3xFT | 4xFT | 5xFT | 6xFT | % Increase in Particulates (SEC) |
|---|---|---|---|---|---|---|---|---|
| 1 | Ac + NaCl | colorless, no particulates | colorless, no particulates | colorless, no particulates | turbid | lots of particulates | lots of particulates | 0.7 |
| 2 | Ac + NaCl + PEG | colorless, no particulates | colorless, no particulates | colorless, no particulates | flakes | cloudy with flakes | few particulates | 0 |
| 3 | Ac + Sucrose | colorless, no particulates | colorless, no particulates | colorless, no particulates | colorless, no particulates | colorless, no particulates | colorless, no particulates | 0.1 |

TABLE 7-continued

Visual Evaluations of Freeze/thaw Stability of Anti-CTLA-4 antibody 11.2.1

| No. | ID | 1xFT | 2xFT | 3xFT | 4xFT | 5xFT | 6xFT | % Increase in Particulates (SEC) |
|---|---|---|---|---|---|---|---|---|
| 4 | Ac + Sorbitol | colorless, no particulates | colorless, no particulates | colorless, no particulates | colorless, no particulates | colorless, no particulates | colorless, no particulates | 0.1 |
| 19 | Ac + Trehalose | colorless, no particulates | colorless, no particulates | colorless, no particulates | colorless, no particulates | colorless, no particulates | colorless, no particulates | 0 |
| 20 | Succ + NaCl | few particulates | few particulates | more particulates | more particulates | cloudy, flakes, particulates | lots of particulates | 1.3 |
| 21 | Succ + NaCl + PEG | colorless, no particulates | fewer particulates | few particulates | cloudy | cloudy | few particulates | 0.2 |
| 7 | Succ + Sucrose | colorless, no particulates | colorless, no particulates | colorless, no particulates | colorless, no particulates | colorless, no particulates | colorless, no particulates | 0.1 |
| 8 | Succ + Sorbitol | colorless, no particulates | colorless, no particulates | colorless, no particulates | colorless, no particulates | colorless, no particulates | colorless, no particulates | 0 |
| 22 | Hist + NaCl | colorless, no particulates | turbid | turbid | cloudy, flakes | cloudy | cloudy, turbid, flakes | 1.1 |
| 23 | Hist + NaCl + PEG | colorless, no particulates | turbid | few particulates | colorless, no particulates | cloudy, flakes, few particulates | few particulates | 0.1 |
| 11 | Hist + Sucrose | colorless, no particulates | colorless, no particulates | colorless, no particulates | colorless, no particulates | colorless, no particulates | colorless, no particulates | 0.1 |
| 12 | Hist + Sorbitol | colorless, no particulates | colorless, no particulates | colorless, no particulates | colorless, no particulates | colorless, no particulates | colorless, no particulates | 0 |
| 24 | Ed + NaCl | colorless, no particulates | colorless, no particulates | colorless, no particulates | cloudy, fewer particulars | lots of particulates | lots of particulates, cloudy | 0.1 |
| 25 | Ed + NaCl + PEG | colorless, no particulates | turbid, fewer particulates | cloudy, flakes | cloudy | cloudy, flakes | few particulates | 0 |
| 15 | Ed + Sucrose | colorless, no particulates | colorless, no particulates | colorless, no particulates | colorless, no particulates | colorless, no particulates | colorless, no particulates | 0 |
| 16 | Ed + Sorbitol | colorless, no particulates | colorless, no particulates | colorless, no particulates | colorless, no particulates | colorless, no particulates | colorless, no particulates | 0.1 |

The formulations containing only sodium chloride (i.e., chloride ions) exhibited a greater increase in soluble particulate levels after freeze/thaw cycling than the formulations containing trehalose, sucrose or sorbitol. The addition of PEG to the formulations containing sodium chloride, however, appeared to reduce soluble particulate levels measured after freeze/thaw cycling relative to the corresponding formulations not containing PEG.

Aggregation Analysis:

In addition, the percent increase in soluble particulates was measured for each formulation after 6 consecutive freeze/thaw cycles using size exclusion chromatography.

After the sixth freeze/thaw cycle, each formulation was analyzed for aggregation using size exclusion chromatography. The size exclusion chromatography was carried out using a TSKgel® G3000SWXL-G2000SWXL column, mobile phase 0.2 M sodium phosphate buffer at pH 7.0, a flow rate of 1 ml/min, and UV detection at 214 nm. Table 7 shows the percentage of eluted high molecular weight species (i.e., aggregates of anti-CTLA-4 monoclonal antibody 11.2.1) measured at the relevant times for each of the formulations. Aggregation levels were calculated by integrating the areas under the chromatogram peaks for each formulation and reporting the integrated areas under the high molecular weight species peaks as a percentage of total peak area (see Table 7). As can be seen in Table 7, the EDTA-buffered formulations showed the lowest levels of aggregation, followed by the histidine-, acetate-, and succinate-buffered formulations, in that order.

Example 5

A study was conducted to evaluate the effect of EDTA, methionine and anaerobic conditions on discoloration and aggregation in liquid formulations comprising monoclonal anti-CTLA-4 antibody 11.2.1. Discoloration and aggregation in such liquid formulations are generally undesirable from a product aesthetic perspective, a product integrity perspective, or both.

Table 8 below lists the formulation treatments that were evaluated. The general procedure used to prepare the formulations was the same as the one described in Example 3. For this Example, a starting formulation comprising monoclonal anti-CTLA-4 antibody 11.2.1 (5 mg/ml), a sodium acetate buffer (20 mM), sodium chloride (8.2 mg/ml), and polysorbate 80 (0.2 mg/ml) and having pH 5.5 was prepared and added to several 10-mL glass vials containing seal tops to allow for aseptic sampling.

Various treatments were performed on the starting formulation according to Table 8 below. As noted in Table 8, methionine was added to some of the vials. Two different concentrations of EDTA were added to other vials. Nitrogen gas was added to the headspaces of selected EDTA- or methionine-containing vials. In addition, some of the remaining untreated vials were deaerated prior to injection of nitrogen gas into their headspaces. Further, some of the remaining vials were left untreated to act as experimental controls.

Two vials from each of the treatments in Table 8 were stored at 40° C. for 0, 2, 4, 6, 8, 10, 14, 16, and 18 weeks. One of the two stored vials at each time point was used for visual color evaluations while the other vial was sampled aseptically to measure the level of 11.2.1 antibody aggregation after storage. Tables 9 and 10 report the results.

TABLE 8

Antibody Formulation Treatments Tested:

| Formulation No. | Treatment Identification | Treatment |
|---|---|---|
| 26 | No treatment | None |
| 27 | +N$_2$ gas in the headspace | Change head-space in vial to Nitrogen gas in lyophilizer by evacuation and replacement |
| 28 | +Deaerated +N$_2$ gas in headspace | De-aerated in lyophilizer, change head-space in vial to Nitrogen in lyophilizer as in #2 above |
| 29 | +26.6 mM Methionine | Added 26.6 mM Methinone as solid |
| 30 | +N$_2$ gas in the headspace +26.6 mM Methionine | Added 26.6 mM Methionine as solid and changed head-space in vial to Nitrogen in lyophilizer as in #2 above |
| 31 | +0.005% Na$_2$EDTA | Added 0.005% Na$_2$EDTA•2H$_2$O as solid |
| 32 | +26.6 mM Methionine +0.005% Na$_2$EDTA | Added 26.6 mM Methionine and 0.005% Na$_2$EDTA•2H$_2$O as solids |
| 33 | +0.01% Na$_2$EDTA | Added 0.01% Na$_2$EDTA•2H$_2$O as solid |

Formulation Appearance Analysis:

Each formulation was visually evaluated after 0 (initial), 2, 4, 6, 8, 10, 14, 16, and 18 weeks for particulate formation, color change and turbidity change. Visual observations were reported in Table 9.

TABLE 9

Visual Evaluations after Formulation Treatments in Table 8:

| Vial No. | Treatment | Initial | 40° C. 2 weeks | 40° C. 4 weeks | 40° C. 6 weeks | 40° C. 8 weeks | 40° C. 10 weeks | 40° C. 12 weeks | 40° C. 14 weeks | 40° C. 16 weeks | 40° C. 18 weeks |
|---|---|---|---|---|---|---|---|---|---|---|---|
| 26 | No treatment | clear and colorless | clear and colorless | pink | pink | pink | pink | pink | pink | pink | pink |
| 27 | +N$_2$ | clear and colorless | clear and colorless | pink | pink | pink | pink | pink | pink | pink | pink |
| 28 | +Deaerated + N$_2$ | clear and colorless | clear and colorless | pink | pink | pink | pink | pink | pink | pink | pink |
| 29 | +26.6 mM Methionine | clear and colorless | clear and colorless | clear and colorless | clear and colorless | clear and colorless | clear and colorless | clear and colorless | clear and colorless | clear and colorless | clear and colorless |
| 30 | +N$_2$ + 26.6 mM Methionine | clear and colorless | clear and colorless | clear and colorless | clear and colorless | clear and colorless | clear and colorless | clear and colorless | clear and colorless | clear and colorless | clear and colorless |
| 31 | +0.005% Na$_2$EDTA | clear and colorless | clear and colorless | clear and colorless | clear and colorless | clear and colorless | clear and colorless | clear and colorless | clear and colorless | clear and colorless | clear and colorless |
| 32 | +26.6 mM Methionine + 0.005% Na$_2$EDTA | clear and colorless | clear and colorless | clear and colorless | clear and colorless | clear and colorless | clear and colorless | clear and colorless | clear and colorless | clear and colorless | clear and colorless |
| 33 | +0.01% Na$_2$EDTA | clear and colorless | clear and colorless | clear and colorless | clear and colorless | clear and colorless | clear and colorless | clear and colorless | clear and colorless | clear and colorless | clear and colorless |

The results in Table 9 indicate that the formulations without EDTA and/or methionine developed a pink coloration in the vial after storage for at least 4 weeks at 40° C. While not wishing to be bound by any particular theory, it is believed that in one embodiment of the invention, this color change may be due, at least in part, to an oxidative process. However, in other embodiments, the color change may be due to any number of other processes, which are unrelated to oxidation.

Addition of Nitrogen gas to the headspace of the vials appeared to have less of an affect on reducing the discoloration than the addition of methionine and/or EDTA.

Aggregation Analysis:

The antibody formulations treated according to Table 8 were stored at a temperature of 40° C. At weeks 0, 2, 6, 8, 10, 14, 16, and 18, each formulation was analyzed for aggregation using size exclusion chromatography. The size exclusion chromatography was carried out using a TSKgel® G3000SWXL-G2000SWXL column, mobile phase 0.2 M sodium phosphate buffer at pH 7.0, a flow rate of 1 ml/min, and UV detection at 214 nm. Table 10 shows the percentage of eluted high molecular weight species (i.e., aggregates of anti-CTLA-4 antibody 11.2.1) measured at the relevant times for each of the formulation treatments. Aggregation levels were calculated by integrating the areas under the chromatogram peaks for each formulation and reporting the integrated areas under the high molecular weight species peaks as a percentage of total peak area (see Table 10).

The results in Table 11 indicate that the addition of methionine or EDTA to the 11.2.1 antibody formulation reduces the percent oxidation at the two indicated methio-

TABLE 10

Percent Aggregation for Formulation Treatments in Table 8:

| Vial No. | Treatment | Initial | 40° C. 2 weeks | 40° C. 4 weeks | 40° C. 6 weeks | 40° C. 8 weeks | 40° C. 10 weeks | 40° C. 12 weeks | 40° C. 14 weeks | 40° C. 16 weeks | 40° C. 18 weeks |
|---|---|---|---|---|---|---|---|---|---|---|---|
| 26 | No treatment | 0.2% | 0.8% | 2.3% | 3.5% | 4.6% | 5.31% | 4.3% | 8.8% | 7.7% | 7.1% |
| 27 | +N₂ | 0.2% | 0.7% | 2.3% | 3.8% | 4.4% | 4.82% | 4.5% | 6.5% | 6.0% | 5.5% |
| 28 | +Deaerated + N₂ | 0.2% | 0.3% | 0.9% | 1.4% | 2.5% | 3.68% | 4.3% | — | 4.6% | 4.8% |
| 29 | +26.6 mM Methionine | 0.2% | 0.2% | 0.5% | 0.5% | 0.6% | 0.59% | 0.5% | 0.7% | 0.8% | 0.7% |
| 30 | +N₂ + 26.6 mM Methionine | 0.2% | 0.2% | 0.5% | 0.4% | 0.4% | 0.51% | 0.5% | 0.5% | 0.7% | 0.7% |
| 31 | +0.005% Na₂EDTA | 0.2% | 0.2% | 0.4% | 0.6% | 0.5% | 0.69% | 0.8% | 1.0% | 1.0% | 0.8% |
| 32 | +26.6 mM Methionine + 0.005% Na₂EDTA | 0.2% | 0.3% | 0.3% | 0.4% | 0.4% | 0.35% | 0.4% | 0.8% | 0.5% | 0.7% |
| 33 | +0.01% Na₂EDTA | 0.2% | 0.2% | 0.4% | 0.6% | 0.6% | 0.73% | 0.3% | 1.2% | 1.0% | 1.2% |

The results in Table 9 indicate that the formulations without EDTA and/or methionine begin to develop a pink coloration in the vial after storage for at least 4 weeks at 40° C. As can be seen in Table 10, the EDTA and/or methionine treated formulations showed the lowest levels of aggregation, followed by the Nitrogen gas-treated and untreated control formulations.

Example 6

A study was conducted to evaluate the effect of methionine and EDTA on the oxidation of certain methionine amino acid residues in the anti-CTLA-4 antibody 11.2.1 after storage as a liquid formulation.
Methionine Oxidation Analysis:

Oxidation levels of methionine residues at amino acid positions 256 and 432 in anti-CTLA-4 antibody 11.2.1 were measured by a Lysine-C mapping method after storage for 8 weeks at 40° C.

Glass vials containing formulation nos. 26, 29 and 33 (Table 8) and their treatments from Example 5 were aseptically sampled at the 8 week time point. The samples were then digested with Lyc-C enzyme in tris buffer at pH 8.0 under standard conditions and analyzed by reversed-phase high performance liquid chromatography. Separation was accomplished using a Grace Vydac® Protein C4 analytical column with 0.1% TFA in water and 0.085% TFA in Acetonitrile gradient elution.

TABLE 11

Percent Oxidation of Methionine Amino Acids in Anti-CTLA-4 antibody 11.2.1 After Treatments in Table 8:

| Formulation No. | Treatment | Percent Oxidation Met 432 | Percent Oxidation Met 256 |
|---|---|---|---|
|  | Initial | 2.3% | 4.9% |
| 26 | No treatment | 15.4% | 32.9% |
| 29 | +26.6 mM Methionine | 0.5% | 1.1% |
| 33 | +0.01% Na₂EDTA | 1.6% | 3.3% | nine residues as compared to the formulation stored without EDTA or methionine.

Example 7

A study was conducted to evaluate the oxidation of certain tryptophan and tyrosine amino acid residues in the anti-CTLA-4 antibody 11.2.1.

Anti-CTLA-4 antibody 11.2.1 formulations that develop a pink discoloration over time were found to have a characteristic absorption maximum at 500 nm after conducting ultraviolet/visible spectroscopy (UV-Vis).

The procedure used to prepare the formulation is the same as the one described in Example 3. For this Example, a formulation comprising a 5 mg/ml solution of monoclonal anti-CTLA-4 antibody 11.2.1 in a 20 mM sodium acetate buffer, 8.2 mg/ml sodium chloride and 0.2 mg/ml polysorbate 80 (at pH 5.5) was stored in two glass vials for 4 weeks at 40° C., at which time, the formulations had developed a pink discoloration.

The solution in one of the discolored vials formulation was then subjected to molecular weight (cut-off) filtration, which allowed the formulation excipients to pass through the filtration device, while leaving behind the antibodies. The filtration eluent (e.g., water and excipients) was clear and colorless, while the collected fraction (e.g., antibody 11.2.1) remained pink. Thus, the filtration experiment indicated that the pink discoloration was related to the antibody 11.2.1 itself in contrast to arising from the formulation's excipients.

Next, the second vial having the pink discoloration was digested with trypsin under standard conditions and analyzed by reversed phase high performance liquid chromatography coupled with mass spectrometry (LC-MS). Separation was accomplished using a Grace Vydac® Protein C4 analytical column with 0.1% TFA in water and 0.085% TFA in Acetonitrile gradient elution. The UV-Vis absorbance of the digested peptides at 500 nm was monitored, and the corresponding peptides were identified on the basis of their molecular weight.

The tryptic peptide, which correlates with the 500 nm absorbance peak, had the amino acid sequence: GLEWVAVIWYDGSNK (SEQ ID NO:17). The peptide sequence GLEWVAVIWYDGSNK (SEQ ID NO:17) was then digested further with Asp-N protease under standard conditions, and the 500 nm absorbance (UV-Vis) peak migrated along with the Asp-N protease digested peptide, which had the amino acid sequence: GLEWVAVIWY (SEQ ID NO:18).

Therefore, without intending to be bound by any particular theory, it is believed that either one or both of the two tryptophan amino acid residues (W) or the tyrosine residue (Y) within the protease digested peptide (GLEWVAVIWY) (SEQ ID NO:18) are possible sites for oxidation, which may have been responsible for the pink discoloration of the antibody 11.2.1 formulation in this example. In particular embodiments, it is believed that either one or both of the two tryptophan amino acid residues (W) within the protease digested peptide (GLEWVAVIWY) (SEQ ID NO:18) are possible sites for oxidation, which may have been responsible for the pink discoloration.

Although, it is also possible that mechanisms other than oxidation may have been responsible for any one or more of the particular discolorations (e.g., pink and yellow) seen in the various formulations evaluated herein.

Example 8

A study was conducted to evaluate the effect of EDTA and DTPA on anti-CTLA-4 antibody 11.2.1 discoloration, aggregation and fragmentation.

Specifically, three liquid formulations comprising antibody 11.2.1 with and without EDTA and DTPA were prepared. The formulations were stored at 40° C. and antibody discoloration, aggregation and fragmentation evaluations were conducted at 0, 2, 4, 6, 8 and 10 weeks.

For this Example, a 20 mg/ml solution of anti-CTLA-4 antibody in 20 mM sodium acetate buffer pH 5.5 with 8.2 mg/ml sodium chloride and 0.2 mg/ml polysorbate 80 was prepared and divided among several glass vials, as described in Example 3, and then treated by addition of EDTA or DTPA. The EDTA and DTPA were added to the formulation vials as solids. Several vials were immediately analyzed for levels of discoloration, aggregation and fragmentation and several other duplicate vials were also stored upright at 40° C. for 2, 4, 6, 8 and 10 weeks.

The treated and untreated vials were then sampled aseptically to measure the level of antibody 11.2.1 aggregation and fragmentation in the formulations at the 2, 4, 6, 8 and 10 week time points and observed for discoloration. Tables 12 and 13 report the results.

Formulation Appearance Analysis:

Each formulation was visually evaluated after 0 (initial), 2, 4, 6, 8 and 10 weeks for particulate formation, color change and turbidity change. Visual observations were reported in Table 12.

TABLE 12

Visual Evaluations of EDTA and DTPA Formulation Treatments:

| No. | Treatment | 0 weeks Initial | 2 weeks 40° C. | 4 weeks 40° C. | 6 weeks 40° C. | 8 weeks 40° C. | 10 weeks 40° C. |
|---|---|---|---|---|---|---|---|
| 26 | No treatment | clear and colorless | clear and colorless | clear and colorless | pink | pink | pink |
| 33 | +0.01% Na₂EDTA•2H₂O | clear and colorless | clear and colorless | clear and colorless | clear and colorless | clear and colorless | clear and colorless |
| 34 | +0.01% DTPA | clear and colorless | clear and colorless | clear and colorless | clear and colorless | clear and colorless | clear and colorless |

The results in Table 12 indicate that the formulations without EDTA or DTPA developed a pink coloration in the vial after storage for at least 6 weeks at 40° C.

Aggregation Analysis:

The antibody formulations treated according to Table 12 were stored at a temperature of 40° C. At weeks 0, 2, 6, 8 and 10, each formulation was analyzed for aggregation using size exclusion chromatography. The size exclusion chromatography was carried out using a TSKgel® G3000SWXL-G2000SWXL column, mobile phase 0.2 M sodium phosphate buffer at pH 7.0, a flow rate of 1 ml/min, and UV detection at 214 nm. Table 13 shows the percentage of eluted high molecular weight species (i.e., aggregates of anti-CTLA-4 antibody 11.2.1) measured at the relevant times for each of the formulation treatments. Aggregation levels were calculated by integrating the areas under the chromatogram peaks for each formulation and reporting the integrated areas under the high molecular weight species peaks as a percentage of total peak area (see Table 13).

TABLE 13

Percent Aggregation for EDTA and DTPA Formulation Treatments:

| No. | Treatment | 0 weeks Initial | 2 weeks 40° C. | 4 weeks 40° C. | 6 weeks 40° C. | 8 weeks 40° C. | 10 weeks 40° C. |
|---|---|---|---|---|---|---|---|
| 26 | No treatment | 0.6% | 0.9% | 1.4% | 2.2% | 2.6% | 3.2% |
| 33 | +0.01% Na₂EDTA•2H₂O | 0.7% | 0.8% | 0.9% | 0.9% | 1.0% | 1.2% |
| 34 | +0.01% DTPA | 0.5% | 0.7% | 0.8% | 0.9% | 0.9% | 0.9% |

As can be seen in Table 7, both the EDTA and DTPA containing formulations showed lower levels of aggregation compared to the formulation without EDTA or DTPA.

Example 9

A study was conducted to evaluate the effect of EDTA and nitrogen gas on anti-CTLA-4 antibody 11.2.1 stability.

Specifically, the impact of EDTA and nitrogen gas on antibody 11.2.1 stability was analyzed with regards to discoloration, aggregation, oxidation, fragmentation and formation of charged species in histidine-buffered formulations containing trehalose and polysorbate 80.

The formulations that were evaluated are listed in Table 13 below. The procedure used to prepare the formulations is the same as the one described later in Example 10. The formulations were stored at 40° C. and stability evaluations were conducted at 0, 4, 8, 12 and 24 weeks.

For this Example, a 20 mg/ml solution of anti-CTLA-4 antibody in 20 mM histidine buffer at pH 5.5 with 84 mg/ml trehalose and 0.2 mg/ml polysorbate 80 was prepared as in Example 10. One part of the formulation was prepared by diluting concentrated stock solution of the antibody with stock solutions of trehalose and Polysorbate 80 to the final composition at 20 mg/mL anti-CTLA-4 antibody. A second part of the formulation was prepared similarly except for the additional step of addition of a 10 mg/mL concentrate of $Na_2EDTA.2H_2O$ to achieve a final concentration of 0.1 mg/mL. The formulations were then dispensed at 1 ml per 2 ml glass vials. Half of the vials of each formulation were then placed in a lyophilizer, and the head-space changed to nitrogen after evacuation. After the vials were charged with nitrogen, a measurement of their oxygen levels reported about 1.5% to 1.6% oxygen, while vials with air in the headspace reported about 19.7% to 20% oxygen.

Several vials were immediately analyzed for levels of discoloration, aggregation, fragmentation, oxidation, and formation of charged species and several other duplicate vials were also stored upright at 40° C. for 2, 4, 8, 12 and 24 weeks. At each time point, two stored vials per treatment were removed from each condition to measure the level of antibody 11.2.1 aggregation, fragmentation, oxidation and formation of charged species in the formulations and observed for discoloration. Tables 14 through 18 report the results.

TABLE 13

Antibody Formulations Tested:

| Vial No. | Head-Space | Buffer | Tonicifier | Surfactant | Chelating Agent |
|---|---|---|---|---|---|
| 35 | Air | Histidine | Trehalose | Polysorbate 80 | — |
| 36 | Nitrogen | Histidine | Trehalose | Polysorbate 80 | — |
| 37 | Air | Histidine | Trehalose | Polysorbate 80 | EDTA |
| 38 | Nitrogen | Histidine | Trehalose | Polysorbate 80 | EDTA |

Formulation Appearance Analysis:

Each formulation was visually evaluated after 0 (initial), 4, 8, 12 and 24 weeks for particulate formation, color change and turbidity change. Visual observations were reported in Table 14.

TABLE 14

Visual Evaluations after Formulation Treatments in Table 13:

| No. | Treatment | 0 weeks Initial | 4 weeks 40° C. | 8 weeks 40° C. | 12 weeks 40° C. | 24 weeks 40° C. |
|---|---|---|---|---|---|---|
| 35 | +Air in the headspace | clear, no particulates | very slight pink, less than 3 particulates | very slight pink, no particulates | slight pink no particulates | slight pink, no particulates |
| 36 | +Nitrogen in the headspace | clear, no particulates | clear, no particulates | clear, no particulates | very slight pink, no particulates | very slight pink, no particulates |
| 37 | +Air in the headspace + EDTA | clear, no particulates | clear, no particulates | clear, less than 3 particulates | clear, no particulates | clear, no particulates |
| 38 | +Nitrogen in the headspace + EDTA | clear, no particulates | clear, no particulates | clear, no particulates | clear, no particulates | clear, no particulates |

The results in Table 14 indicate that the formulation without EDTA or nitrogen gas developed a pink coloration after storage for 4 weeks at 40° C. Table 14 also indicates that the formulation having the vial headspace air replaced with nitrogen gas delayed the onset of pink discoloration until week 12. Both formulations containing EDTA had no visible discoloration for at least 24 weeks.

Aggregation Analysis:

The antibody formulations prepared according to Table 13 were stored at a temperature of 40° C. At weeks 0, 4, 8, 12 and 24, each formulation was analyzed for aggregation using size exclusion chromatography. The formulation vials were aseptically sampled at each time point. The size exclusion chromatography was carried out on the samples using a TSKgel® G3000SWXL-G2000SWXL column, mobile phase 0.2 M sodium phosphate buffer at pH 7.0, a flow rate of 1 ml/min, and UV detection at 214 nm. Table 15 shows the percentage of eluted high molecular weight species (i.e., aggregates of anti-CTLA-4 antibody 11.2.1) measured at the relevant times for each of the formulation treatments. Aggregation levels were calculated by integrating the areas under the chromatogram peaks for each formulation and reporting the integrated areas under the high molecular weight species peaks as a percentage of total peak area (see Table 15).

TABLE 15

Percent Aggregation for Formulations in Table 13:

| Formulation No. | Treatment | 0 weeks Initial | 4 weeks 40° C. | 8 weeks 40° C. | 12 weeks 40° C. | 24 weeks 40° C. |
|---|---|---|---|---|---|---|
| 35 | +Air in the headspace | 0.7% | 0.9% | 1.3% | 1.5% | 3.9% |

TABLE 15-continued

Percent Aggregation for Formulations in Table 13:

| Formulation No. | Treatment | 0 weeks Initial | 4 weeks 40° C. | 8 weeks 40° C. | 12 weeks 40° C. | 24 weeks 40° C. |
|---|---|---|---|---|---|---|
| 36 | +Nitrogen in the headspace | 0.7% | 0.6% | 0.7% | 1% | 1.5% |
| 37 | +Air in the headspace + EDTA | 0.7% | 0.6% | 0.8% | 0.9% | 1.5% |
| 38 | +Nitrogen in the headspace + EDTA | 0.7% | 0.6% | 0.6% | 0.8% | 1.1% |

As can be seen in Table 15, the EDTA containing formulation, the nitrogen gas formulation, and the EDTA plus nitrogen gas formulation showed lower levels of aggregation over time as compared to a formulation without EDTA and having air in the headspace.

Fragmentation Analysis:

The antibody formulations prepared according to Table 13 were stored at a temperature of 40° C. At weeks 0, 4, 8, 12 and 24, each formulation was analyzed for total hydrolytic impurities (i.e., fragmentation) using reduced SDS-PAGE (rSDS-PAGE). The formulation vials were aseptically sampled at each time point and loaded onto NuPAGE® 4-12% bis-Tris gels with colloidal blue (Coomassie) stain. Gel reduction was achieved by use of the NuPAGE® reducing agent. The percentage impurity (i.e., fragmentation) of each sample band in the reduced gels was estimated by scanning on either a Molecular Dynamics Personal Densitometer PDQC-90 or Bio-Rad GS800 Imaging Densitometer. Fragmentation level was calculated as a percentage of total band volume (see Table 16).

TABLE 16

Percent Total (Impurities) Fragmentation for Formulations in Table 13:

| Formulation No. | Treatment | 0 weeks Initial | 4 weeks 40° C. | 8 weeks 40° C. | 12 weeks 40° C. | 24 weeks 40° C. |
|---|---|---|---|---|---|---|
| 35 | +Air in the headspace | 1.3% | 4.1% | 5.5% | 8.0% | 12.4% |
| 36 | +Nitrogen in the headspace | 1.2% | 3.5% | 4.4% | 6.3% | 10.6% |
| 37 | +Air in the headspace + EDTA | 1.3% | 3.2% | 4.4% | 5.9% | 10.6% |
| 38 | +Nitrogen in the headspace + EDTA | 1.3% | 3.5% | 4.1% | 5.6% | 10.2% |

As can be seen in Table 16, the EDTA containing formulation, the nitrogen gas formulation, and the EDTA plus nitrogen gas formulation showed lower levels of fragmentation over time as compared to a formulation without EDTA and having air in the headspace.

Formation of Acidic and Basic Species:

The antibody formulations prepared according to Table 13 were stored at a temperature of 40° C. At weeks 0, 4, 12 and 24, each formulation was analyzed for the formation of acidic and basic species using Imaging Capillary Electrophoresis (iCE). The Imaging Capillary Electrophoresis was conducted using a Convergent Biosciences iCE$_{280}$ analyzer for evaluation of charge heterogeneity. The Convergent iCE$_{280}$ is an imaging capillary isoelectric focusing (IEF) instrument, which allows the user to take an image of a separated sample contained within a capillary.

The formulation vials were aseptically sampled at each time point. The samples were then prepared in a mixture of electrophoretic ampholytes, methyl cellulose, calibration markers, and water. The samples were introduced into the iCE$_{280}$ and a high potential/voltage was applied. The IEF assays were conducted using manually prepared pH 3-10.5 polyacrylamide gels using Coomassie blue stain. The sample protein components were separated based on their relative isoelectric points (pI) and their location. The relative amount of each separated component was observed by an imaging CCD camera. The data was then processed and reported as loss of the main peak (i.e., formation of acidic and basic species) using conventional chromatography integration software (see Table 17).

TABLE 17

Loss of Main Peak for Formulations in Table 13:

| Formulation No. | Treatment | 0 weeks Initial | 4 weeks 40° C. | 8 weeks 40° C. | 12 weeks 40° C. | 24 weeks 40° C. |
|---|---|---|---|---|---|---|
| 35 | +Air in the headspace | 65.3 | 50.3 | — | 28.8 | 15.5 |
| 36 | +Nitrogen in the headspace | 63.8 | 52.2 | — | 33.1 | 22.7 |
| 37 | +Air in the headspace + EDTA | 62.3 | 55.4 | — | 37.0 | 23.4 |
| 38 | +Nitrogen in the headspace + EDTA | 63.9 | 56.6 | — | 40.0 | 24.8 |

As can be seen in Table 17, the EDTA containing formulation, the nitrogen gas formulation, and the EDTA plus nitrogen gas formulation showed higher levels of the intact main peak over time as compared to a formulation without EDTA and having air in the headspace. Thus, the amount of acidic and basic species formation is greater over time in formulations lacking EDTA and/or nitrogen gas in the headspace.

Amino Acid Oxidation Analysis:

Oxidation levels of methionine residues at amino acid positions 256 and 432 in anti-CTLA-4 antibody 11.2.1 were measured by a Lysine-C mapping method after storage for 12 weeks at 40° C.

The vials containing the formulations from Table 13 were aseptically sampled at the 12 week time point. The samples were then digested with a Lysyl Endopeptidase (Lys-C) enzyme tris buffer at pH 8.0 under standard conditions and analyzed by reversed-phase high performance liquid chromatography. Separation was accomplished using a Grace Vydac® Protein C4 analytical column with 0.1% TFA in water and 0.085% TFA in Acetonitrile gradient elution.

TABLE 18

Percent Oxidation of Methionine Amino Acids in Anti-CTLA-4 antibody 11.2.1 in Formulations from Table 13:

| Formulation No. | Treatment | Amino Acid Residue | Percent Oxidation 0 weeks | Percent Oxidation 12 weeks |
|---|---|---|---|---|
| 35 | +Air in the headspace | Met-432 | 1.6% | 7.3% |
|  |  | Met-256 | 5% | 17.9% |

TABLE 18-continued

Percent Oxidation of Methionine Amino Acids
in Anti-CTLA-4 antibody 11.2.1 in Formulations from Table 13:

| Formulation No. | Treatment | Amino Acid Residue | Percent Oxidation 0 weeks | Percent Oxidation 12 weeks |
|---|---|---|---|---|
| 36 | +Nitrogen in the headspace | Met-432 Met-256 | 1.6% 5% | 3.3% 7.8% |
| 37 | +Air in the headspace + EDTA | Met-432 Met-256 | 1.6% 5% | 3.9% 9.7% |
| 38 | +Nitrogen in the headspace + EDTA | Met-432 Met-256 | 1.6% 5% | 2.6% 5.9% |

The results in Table 18 indicate that the addition of EDTA to the 11.2.1 antibody formulation and/or addition of nitrogen gas to the vial headspace reduced the percent oxidation at the two indicated methionine residues as compared to a formulation without EDTA and having air in the headspace.

Example 10

A study was conducted to compare the effect on stability of anti-CTLA-4 antibody 11.2.1 formulations comprising a sodium acetate buffer and sodium chloride (i.e., chloride ions) versus formulations comprising a histidine buffer and trehalose.

Specifically, the impact on antibody 11.2.1 stability was analyzed with regards to discoloration, aggregation, and fragmentation.

The formulations that were evaluated are listed in Table 19 below. The procedure used to prepare the formulations is the same as the one described in Example 3.

The formulations in Table 19 were prepared by taking an 11.9 mg/ml stock solution of antibody 11.2.1 in 20 mM sodium acetate buffer pH 5.5, 140 mM sodium chloride and subjecting it to an ultrafiltration/diafiltration (UF/DF) step in a Millipore Lab Scale™ TFF System with a Pellicon® XL PBTK 30K 50 cm² membrane. Next, concentrated solutions of the antibody 11.2.1 were prepared in the 35 to 40 mg/ml range in 20 mM sodium acetate or 20 mM histidine buffers.

Concentrates of the tonicifying agent were prepared in either the sodium acetate or histidine buffer at three times the target final concentrations. A concentrated solution of polysorbate 80 was prepared at 20 mg/ml and $Na_2EDTA \cdot 2H_2O$ at 10 mg/ml in each of the buffers. Individual formulations were prepared by diluting the concentrated solutions appropriately. The formulations were then filtered through 0.2μ sterilizing grade filters and filled into several duplicate vials. A fill-volume of 1 ml was used in 2-ml Type 1 glass vials. The vials were closed with Daikyo 777-1 Fluorotec® coated stoppers, crimp sealed, and stored upright in stability chambers at 25° C. and 40° C. Another set of vials was also placed at −20° C. for 4 weeks, and another set was subject to 4× freeze/thaw cycles (water-filled vials box) as described in Example 4. All formulations had a pH of 5.5 and an anti-CTLA-4 antibody 11.2.1 concentration of 20 mg/ml.

Several vials were immediately analyzed for levels of discoloration, aggregation, and fragmentation and several other duplicate vials were also stored upright at 25° C. and 40° C. for 4, 8, 12, 18, 24 and 36 weeks. At each time point, two stored vials per formulation were removed from each condition to measure the level of antibody 11.2.1 aggregation, fragmentation, and observed for discoloration as well. Tables 20 through 24 and FIGS. 3 and 4 report the results.

TABLE 19

Antibody Formulations Tested:

| No. | Acetate (mM) | Histidine (mM) | Tween 80 (mg/ml) | Sodium Chloride (mg/ml) | Mannitol (mg/ml) | Trehalose (mg/ml) | Glycine (mg/ml) | EDTA (mg/ml) | PEG 3350 (mg/ml) | Methionine (mg/ml) |
|---|---|---|---|---|---|---|---|---|---|---|
| 26 | 20 | — | 0.2 | 8.2 | — | — | — | — | — | — |
| 39 | 20 | — | 0.2 | 5.0 | 18 | — | — | 0.1 | — | — |
| 40 | — | 20 | 0.2 | — | — | 84 | — | — | — | — |
| 37 | — | 20 | 0.2 | — | — | 84 | — | 0.1 | — | — |
| 41 | — | 20 | 0.2 | — | — | 84 | — | 0.1 | — | 2 |
| 42 | — | 20 | 0.4 | — | — | 84 | — | 0.1 | — | — |
| 43 | — | 20 | 0.2 | — | 41 | 10 | — | — | — | — |
| 44 | — | 20 | 0.2 | — | 41 | 10 | — | 0.1 | — | — |

Formulation Appearance Analysis:

Each formulation was visually evaluated after 1) initially mixing the formulation, 2) freezing the formulation at −20° C. for 4 weeks, and 3) after 4 freeze/thaw cycles (−70° C. to 5° C. in box along with water-filled vials as described in Example 4). Each formulation was visually evaluated after 0 (initial), 8, 12 and 24 weeks for particulate formation, color change and turbidity change. The formulations were evaluated for particulate formation, color changes and turbidity changes and reported in Table 20 (freeze/thaw), Table 21 (storage at 25° C.), and Table 22 (storage at 40° C.).

TABLE 20

Visual Evaluations of Formulations from Table 19 after Freeze/Thaw:

| No. | Initial | After Freezing at −20° C. for 4 weeks | After 4 Freeze/Thaw Cycles |
|---|---|---|---|
| 26 | clear, colorless, no particulates | very slightly cloudy, more than 3 particulates | very slightly cloudy, many particulates |
| 39 | clear, colorless, no particulates | clear, colorless, no particulates | clear, colorless, less than 3 particulates |
| 40 | clear, colorless, no particulates | clear, colorless, no particulates | clear, colorless, less than 3 particulates |
| 37 | clear, colorless, no particulates | clear, colorless, no particulates | clear, colorless, less than 3 particulates |
| 41 | clear, colorless, no particulates | clear, colorless, no particulates | clear, colorless, less than 3 particulates |
| 42 | clear, colorless, no particulates | clear, colorless, no particulates | clear, colorless, less than 3 particulates |
| 43 | clear, colorless, no particulates | clear, colorless, no particulates | clear, colorless, less than 3 particulates |
| 44 | clear, colorless, no particulates | clear, colorless, less than 3 particulates | clear, colorless, no particulates |

TABLE 21

Visual Evaluations of Formulations from Table 19 after Storage at 25° C.:

| No. | Initial | 8 weeks 25° C. | 12 weeks 25° C. | 24 weeks 25° C. |
|---|---|---|---|---|
| 26 | clear, colorless, no particulates | very slightly cloudy, no particulates | clear, colorless, no particulates | clear, colorless, less than 3 particulates |
| 39 | clear, colorless, no particulates | clear, colorless, no particulates | clear, colorless, less than 3 particulates | — |
| 40 | clear, colorless, no particulates | clear, colorless, no particulates | clear, colorless, no particulates | clear, colorless, no particulates |
| 37 | clear, colorless, no particulates | clear, colorless, no particulates | clear, colorless, no particulates | clear, colorless, no particulates |
| 41 | clear, colorless, no particulates | clear, colorless, no particulates | clear, colorless, no particulates | clear, colorless, no particulates |
| 42 | clear, colorless, no particulates | clear, colorless, no particulates | clear, colorless, no particulates | clear, colorless, no particulates |
| 43 | clear, colorless, no particulates | — | clear, colorless, no particulates | clear, colorless, no particulates |
| 44 | clear, colorless, no particulates | clear, colorless, no particulates | clear, colorless, no particulates | very slightly cloudy, no particulates |

TABLE 22

Visual Evaluations of Formulations from Table 19 after Storage at 40° C.:

| No. | Initial | 8 weeks 40° C. | 12 weeks 40° C. | 24 weeks 40° C. |
|---|---|---|---|---|
| 26 | clear, colorless, no particulates | very slightly cloudy, no particulates | clear, colorless, no particulates | slightly pink, no particulates |
| 39 | clear, colorless, no particulates | clear, colorless, no particulates | clear, colorless, no particulates | — |
| 40 | clear, colorless, no particulates | clear, colorless, no particulates | clear, colorless, no particulates | slightly pink, no particulates |
| 37 | clear, colorless, no particulates | clear, colorless, no particulates | clear, colorless, no particulates | clear, colorless, no particulates |
| 41 | clear, colorless, no particulates | clear, colorless, no particulates | clear, colorless, no particulates | clear, colorless, no particulates |
| 42 | clear, colorless, no particulates | clear, colorless, no particulates | clear, colorless, no particulates | clear, colorless, no particulates |
| 43 | clear, colorless, no particulates | clear, colorless, no particulates | clear, colorless, no particulates | slightly pink, no particulates |
| 44 | clear, colorless, no particulates | clear, colorless, no particulates | clear, colorless, no particulates | clear, colorless, no particulates |

The results in Tables 20 through 22 indicate that antibody 11.2.1 formulations containing EDTA had reduced discoloration, reduced turbidity, and reduced particulate formation as compared to those formulations without EDTA. Overall, formulations containing sodium chloride had increased discoloration, turbidity, and particulate formation as compared to formulations having EDTA, but without sodium chloride.

Aggregation Analysis:

The antibody formulations prepared according to Table 19 were stored at a temperature of 25° C. and 40° C. At weeks 0 (initial), 4, 8, 12, 24 and 36 weeks, the 25° C. formulations were analyzed for aggregation using size exclusion chromatography. At weeks 4, 8, 12 and 24 weeks, the 40° C. formulations were analyzed for aggregation using size exclusion chromatography. The formulation vials were aseptically sampled at each time point. The size exclusion chromatography was carried out on the samples using a TSKgel® G3000SWXL-G2000SWXL column, mobile phase 0.2 M sodium phosphate buffer at pH 7.0, a flow rate of 1 ml/min, and UV detection at 214 nm. Tables 23(a) and 23(b) show the percentage of antibody 11.2.1 aggregation measured at the relevant times for each of the formulation treatments. Aggregation levels were calculated by integrating the areas under the chromatogram peaks for each formulation and reporting the integrated areas under the high molecular weight species peaks as a percentage of total peak area (see Tables 23(a) and 23(b)).

TABLE 23(a)

Percent Aggregation for Formulations in Table 19 after Storage at 25° C.:

| No. | Initial | 4 weeks 25° C. | 8 weeks 25° C. | 12 weeks 25° C. | 18 weeks 25° C. | 24 weeks 25° C. | 36 weeks 25° C. |
|---|---|---|---|---|---|---|---|
| 26 | 0.7% | 0.9% | 0.9% | 1.1% | 1.8% | 1.8% | 3.0% |
| 39 | 0.7% | 0.8% | 0.8% | 1.1% | — | — | — |
| 40 | 0.6% | 0.6% | 0.7% | 0.9% | 0.95% | 0.8% | 0.9% |
| 37 | 0.6% | 0.6% | 0.6% | 0.7% | 0.7% | 0.7% | 0.8% |
| 41 | 0.6% | 0.6% | 0.6% | 0.7% | 0.7% | 0.7% | 0.7% |
| 42 | 0.6% | 0.6% | 0.6% | 0.8% | 0.8% | 0.8% | 0.8% |
| 43 | 0.6% | 0.6% | — | — | 0.7% | 0.8% | 0.9% |
| 44 | 0.6% | 0.6% | 0.6% | 0.7% | 0.7% | 0.8% | 0.8% |

Table 23(b) below reports the aggregation data that is graphically presented in FIG. 3.

TABLE 23(b)

Percent Aggregation for Formulations in Table 19 after Storage at 40° C.:

| No. | Initial | 4 weeks 40° C. | 8 weeks 40° C. | 12 weeks 40° C. | 24 weeks 40° C. |
|---|---|---|---|---|---|
| 26 | 0.7% | 1.0% | 1.3% | 2.8% | 4.7% |
| 39 | 0.6% | 1.0% | 1.0% | 1.4% | — |
| 40 | 0.6% | 0.7% | 0.9% | 1.0% | 1.4% |
| 37 | 0.6% | 0.6% | 0.6% | 0.8% | 1.1% |
| 41 | 0.6% | 0.6% | 0.6% | 0.7% | 0.8% |
| 42 | 0.6% | 0.6% | 0.6% | 0.8% | 1.1% |
| 43 | 0.6% | 0.8% | — | — | 1.7% |
| 44 | 0.6% | 0.6% | 0.6% | 0.8% | 0.9% |

Figure 3:
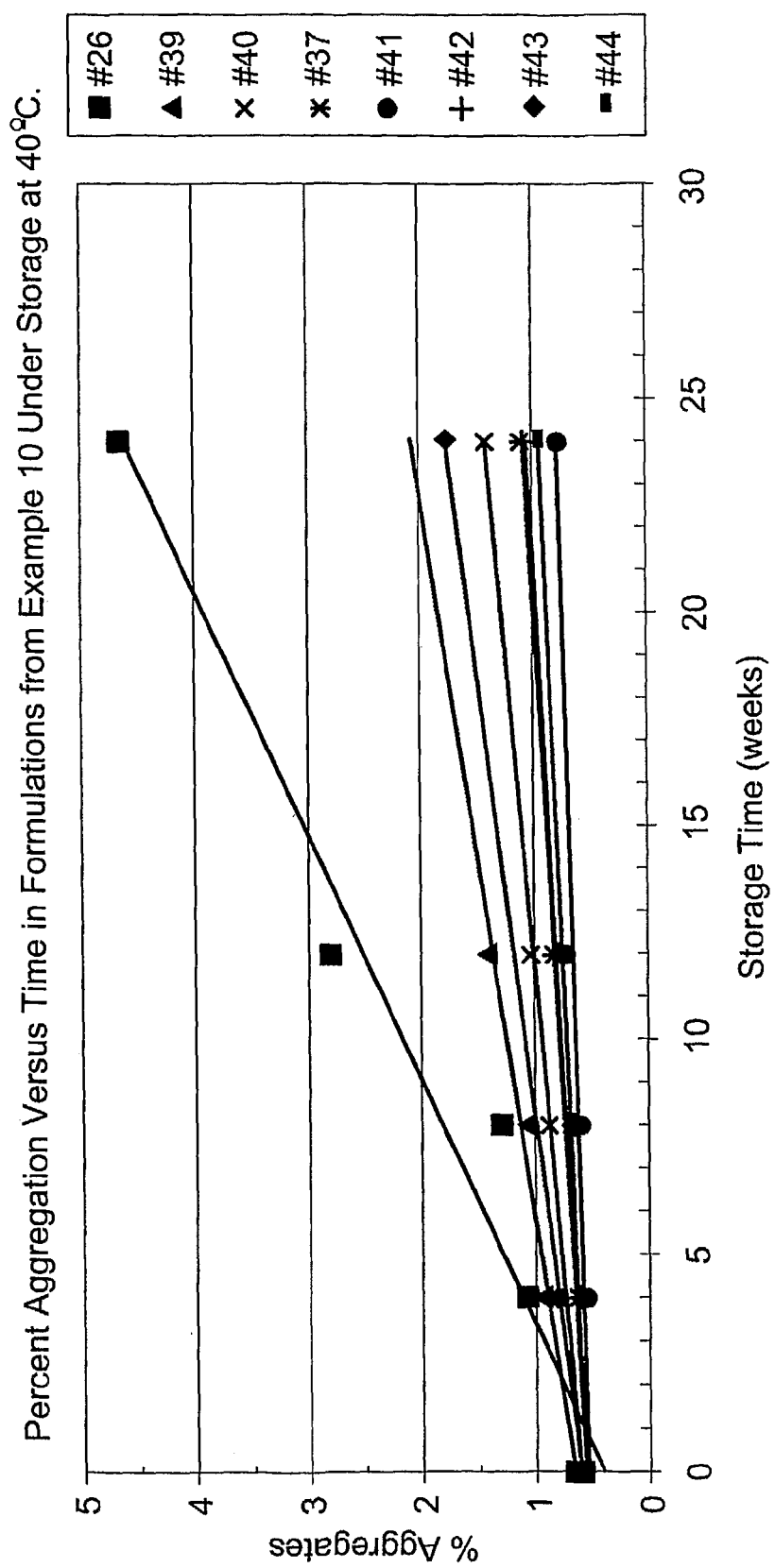
FIG. 3 is a line graph that shows the percent aggregation in various test formulations on storage under accelerated conditions at 40° C. for up to 24 weeks by SEC.

As can be seen in Tables 23(a), 23(b) and FIG. 3, the EDTA-containing formulations showed reduced levels of aggregation as compared to a formulation lacking EDTA, but having an acetate buffer and sodium chloride, after storage at 25° C. and 40° C. Moreover, a formulation containing a histidine buffer (without EDTA) had a reduced amount of aggregation compared to a formulation lacking EDTA, but containing an acetate buffer and sodium chloride.

Fragmentation Analysis:

The antibody formulations prepared according to Table 19 were stored at a temperature of 25° C. and 40° C. At weeks 0 (initial), 4, 8, 12, 18 and 36 weeks, each formulation was analyzed for total hydrolytic impurities (i.e., fragmentation) using reduced SDS-PAGE (rSDS-PAGE). The formulation vials were aseptically sampled at each time point and loaded onto NuPAGE® 4-12% bis-Tris gels with colloidal blue (Coomassie) stain. Gel reduction was achieved by use of the NuPAGE® reducing agent. The percentage impurity (i.e., fragmentation) of each sample band in the reduced gels was estimated by scanning on either a Molecular Dynamics Personal Densitometer PDQC-90 or Bio-Rad GS800 Imaging Densitometer. Fragmentation level was calculated as a percentage of total band volume (see Tables 24(a) and 24(b)).

TABLE 24(a)

Percent Fragmentation for Formulations in Table 19 after Storage at 25° C.:

| No. | Initial | 4 weeks 25° C. | 8 weeks 25° C. | 12 weeks 25° C. | 18 weeks 25° C. | 24 weeks 25° C. | 36 weeks 25° C. |
|---|---|---|---|---|---|---|---|
| 26 | 1.8% | 1.6% | 2.6% | 2.4% | 1.3% | 3.5% | 3.7% |
| 39 | 1.6% | 1.4% | 2.4% | 1.5% | — | — | — |
| 40 | 1.6% | 1.7% | 2.6% | 1.4% | 1.4% | 3.3% | 3.2% |
| 37 | 1.6% | 1.6% | 2.5% | 1.4% | 1.4% | 3.3% | 3.1% |
| 41 | 1.6% | 1.6% | 2.6% | 1.4% | 1.2% | 3.3% | 2.9% |
| 42 | 1.9% | 1.8% | 2.5% | 1.6% | 1.2% | 3.0% | 2.9% |
| 43 | 1.8% | 1.8% | — | — | 1.2% | 3.2% | 3.1% |
| 44 | 1.7% | 1.7% | 2.6% | 1.4% | 1.3% | 3.1% | 2.8% |

Table 24(b) below reports the fragmentation data that is graphically presented in FIG. 4.

TABLE 24(b)

Percent Fragmentation for Formulations in Table 19 after Storage at 40° C.:

| No. | Initial | 4 weeks 40° C. | 8 weeks 40° C. | 12 weeks 40° C. | 24 weeks 40° C. |
|---|---|---|---|---|---|
| 26 | 1.8% | 5.2% | 6.1% | 7.8% | 11.7% |
| 39 | 1.6% | 5.3% | 6.7% | 6.5% | — |
| 40 | 1.6% | 5.3% | 6.8% | 6.2% | 10.0% |
| 37 | 1.6% | 5.2% | 6.6% | 5.5% | 10.2% |
| 41 | 1.6% | 5.2% | 5.0% | 5.5% | 10.0% |
| 42 | 1.9% | 5.3% | 5.1% | 5.8% | 9.7% |
| 43 | 1.8% | 5.3% | — | — | 11.0% |
| 44 | 1.7% | 4.5% | 5.2% | 5.5% | 9.5% |

Figure 4:
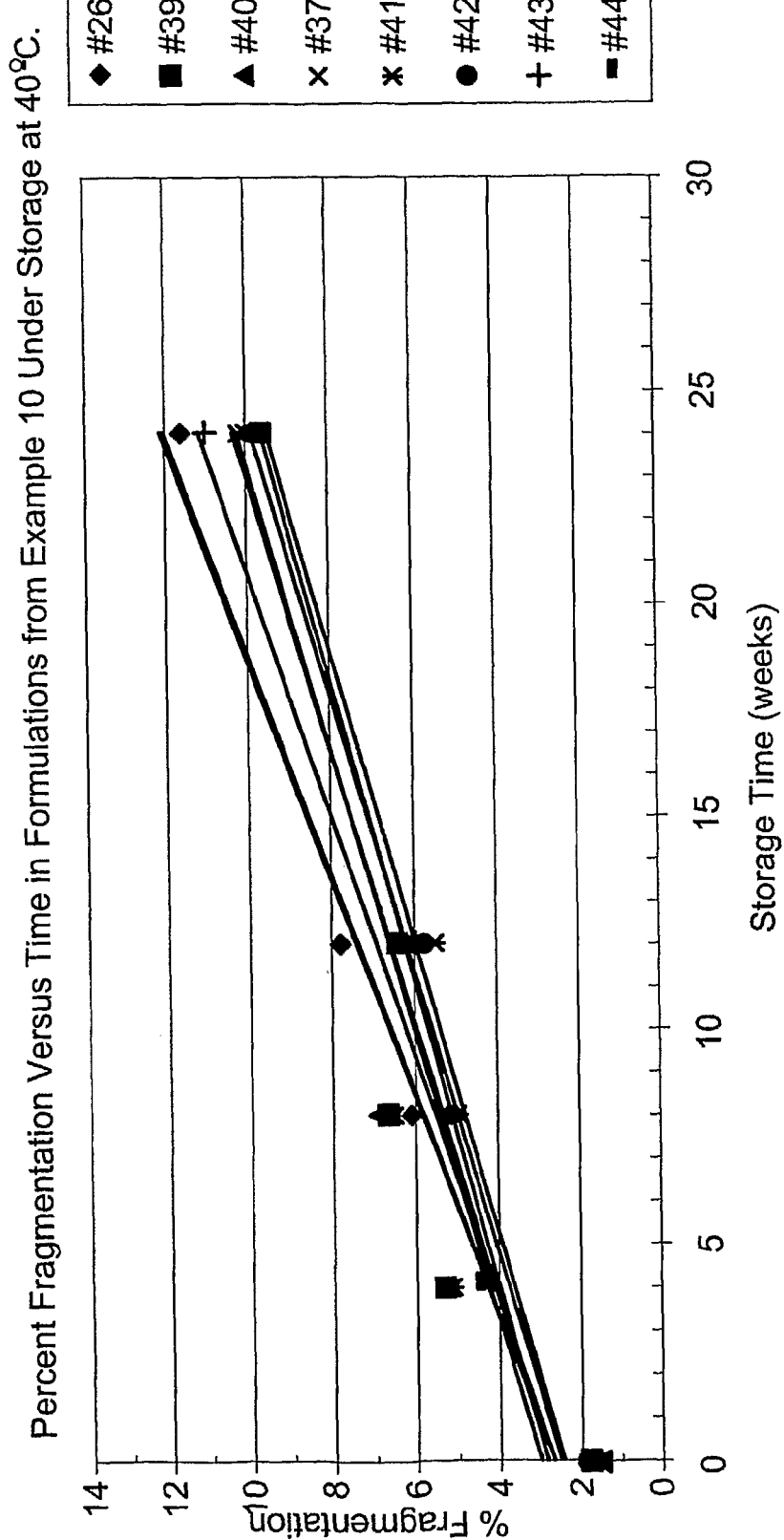
FIG. 4 is a line graph that shows the percent total (hydrolytic) impurities formation in various test formulations on storage under accelerated conditions at 40° C. for up to 24 weeks by rSDSPAGE.

As can be seen in Tables 24(a), 24(b) and FIG. 4, the EDTA-containing formulations showed reduced levels of fragmentation as compared to a formulation lacking EDTA, but having an acetate buffer and sodium chloride, after storage at 25° C. and 40° C.

Example 11

A study was conducted to compare the effect of varying concentrations of EDTA on stability of anti-CTLA-4 antibody 11.2.1 formulations. Alternatives to a histidine buffer-trehalose formulation were also tested, by replacing part of the trehalose with mannitol.

Specifically, the impact on antibody 11.2.1 stability was analyzed with regards to discoloration, aggregation, fragmentation, and oxidation.

The formulations that were evaluated are listed in Table 25 below. The procedure used to prepare the formulations is the same as the one described in Example 10.

The formulations in Table 25 were prepared by taking an 11.9 mg/ml stock solution of antibody 11.2.1 in 20 mM sodium acetate buffer pH 5.5, 140 mM sodium chloride and subjecting it to an ultrafiltration/diafiltration (UF/DF) step in a Millipore Lab Scale™ TFF System with a Pellicon® XL PBTK 30K 50 cm$^2$ membrane. Next, concentrated solutions of the antibody 11.2.1 were prepared in the 35 to 40 mg/ml range in 20 mM sodium acetate or 20 mM histidine buffers.

Concentrates of the tonicifying agent were prepared in either the sodium acetate or histidine buffer at three times the target final concentrations. A concentrated solution of polysorbate 80 was prepared at 20 mg/ml and Na$_2$EDTA.2H$_2$O at 10 mg/ml in each of the buffers. Individual formulations were prepared by diluting the concentrated solutions appropriately. EDTA concentrations (as Na$_2$EDTA.2H$_2$O) were examined in the range of 0-0.1 mg/ml. The formulations were then filtered through 0.2μ sterilizing grade filters and filled into several duplicate vials. A fill-volume of 1 ml was used in 2-ml Type 1 glass vials.

The vials were closed with Daikyo 777-1 Fluorotec® coated stoppers, crimp sealed, and stored upright in stability chambers at 25° C. and 40° C. Another set of vials was subject to 4× freeze/thaw cycles as described in Example 10. All formulations had a pH of 5.5 and an anti-CTLA-4 antibody 11.2.1 concentration of 20 mg/ml.

Several vials were immediately analyzed for levels of discoloration, aggregation, fragmentation, and oxidation and several other duplicate vials were also stored upright at 25° C. and 40° C. for 4, 8, 13, 18 and 24 weeks. At each time point, two stored vials per formulation from each condition were removed to measure the level of antibody 11.2.1 aggregation, fragmentation, and observed for discoloration as well. Tables 26 to 31 and FIGS. 5 to 10 report the results.

TABLE 25

Antibody Formulations Tested:

| No. | Acetate (mM) | Histidine (mM) | Tween 80 (mg/ml) | Mannitol (mg/ml) | Trehalose (mg/ml) | EDTA (mg/ml) | Sodium Chloride (mg/ml) |
|---|---|---|---|---|---|---|---|
| 26 | 20 | — | 0.2 | — | — | — | 8.4 |
| 40 | — | 20 | 0.2 | — | 84 | — | — |
| 45 | — | 20 | 0.2 | — | 84 | 0.001 | — |
| 46 | — | 20 | 0.2 | — | 84 | 0.005 | — |
| 47 | — | 20 | 0.2 | — | 84 | 0.01 | — |
| 48 | — | 20 | 0.2 | — | 84 | 0.05 | — |
| 37 | — | 20 | 0.2 | — | 84 | 0.1 | — |
| 49 | — | 20 | 0.2 | 10 | 70 | 0.001 | — |
| 50 | — | 20 | 0.4 | 10 | 70 | 0.01 | — |
| 51 | — | 20 | 0.2 | 10 | 70 | 0.1 | — |
| 52 | — | 20 | 0.2 | 20 | 50 | 0.001 | — |
| 53 | — | 20 | 0.2 | 20 | 50 | 0.01 | — |
| 54 | — | 20 | 0.2 | 20 | 50 | 0.1 | — |

Formulation Appearance Analysis:

Each formulation was visually evaluated after 1) initially mixing the formulation, 2) after 4 freeze/thaw cycles, and 3) after storage at 25° C. and 40° C. for 4, 8, 13, 18 and 24 weeks. The formulations were evaluated for particulate formation, color changes and turbidity changes and reported in Tables 26 to 28.

TABLE 26

Visual Evaluations of Formulations from Table 25 after Freeze/Thawing:

| Formulation No. | Initial | After 4X Freeze/Thaw Cycles |
|---|---|---|
| 26 | clear, colorless, no particulates | very slightly cloudy, no particulates |
| 40 | clear, colorless, no particulates | clear colorless, less than 3 particulates |
| 45 | clear, colorless, no particulates | clear, colorless, less than 3 particulates |
| 46 | clear, colorless, no particulates | clear, colorless, less than 3 particulates |
| 47 | clear, colorless, no particulates | clear, colorless, less than 3 particulates |
| 48 | clear, colorless, no particulates | clear, colorless, greater than 3 particulates |
| 37 | clear, colorless, no particulates | clear, colorless, no particulates |
| 49 | clear, colorless, no particulates | clear, colorless, greater than 3 particulates |
| 50 | clear, colorless, no particulates | clear, colorless, less than 3 particulates |
| 51 | clear, colorless, no particulates | clear, colorless, less than 3 particulates |
| 52 | clear, colorless, no particulates | clear, colorless, no particulates |
| 53 | clear, colorless, no particulates | clear, colorless, less than 3 particulates |
| 54 | clear, colorless, no particulates | clear, colorless, less than 3 particulates |

TABLE 27

Visual Evaluations of Formulations from Table 25 after Storage at 25° C.:

| No. | Initial | 13 weeks 25° C. | 18 weeks 25° C. | 24 weeks 25° C. |
|---|---|---|---|---|
| 26 | clear, colorless, no particulates | clear, colorless, no particulates | very slightly pink, no particulates | |
| 40 | clear, colorless, no particulates | very slightly pink, no particulates | — | clear, Y6*, no particulates |
| 45 | clear, colorless, no particulates | clear, colorless, no particulates | clear, colorless, no particulates | clear, colorless, no particulates |
| 46 | clear, colorless, no particulates | clear, colorless, no particulates | — | clear, colorless, no particulates |
| 47 | clear, colorless, no particulates | clear, colorless, no particulates | clear, colorless, no particulates | clear, colorless, no particulates |
| 48 | clear, colorless, no particulates | clear, colorless, no particulates | — | clear, colorless, no particulates |
| 37 | clear, colorless, no particulates | clear, colorless, no particulates | clear, colorless, no particulates | clear, colorless, no particulates |
| 49 | clear, colorless, no particulates | clear, colorless, no particulates | — | clear, colorless, no particulates |
| 50 | clear, colorless, no particulates | clear, colorless, less than 3 particulates | — | clear, colorless, no particulates |
| 51 | clear, colorless, no particulates | clear, colorless, less than 3 particulates | — | clear, colorless, no particulates |
| 52 | clear, colorless, no particulates | clear, colorless, no particulates | — | clear, colorless, no particulates |
| 53 | clear, colorless, no particulates | clear, colorless, no particulates | — | clear, colorless, no particulates |
| 54 | clear, colorless, no particulates | clear, colorless, less than 3 particulates | — | clear, colorless, no particulates |

*Y6 and Y4 are color scale notations on the EP Yellow scale. Y6 being less yellow than Y4. Ref: PhEur 5.0, 2005 Monograph 2.2.2).

TABLE 28

Visual Evaluations of Formulations from Table 25 after Storage at 40° C.:

| No. | Initial | 8 weeks 40° C. | 13 weeks 40° C. | 18 weeks 40° C. | 24 weeks 40° C. |
|---|---|---|---|---|---|
| 26 | clear, colorless, no particulates | very slightly pink, no particulates | very slightly pink, no particulates | pink, no particulates | pink, no particulates |
| 40 | clear, colorless, no particulates | very slightly pink, no particulates | very slightly pink, no particulates | — | clear, Y4*, no particulates |
| 45 | clear, colorless, no particulates | clear, colorless, no particulates | clear, colorless, no particulates | clear, colorless, no particulates | clear, colorless, no particulates |
| 46 | clear, colorless, no particulates | clear, colorless, no particulates | clear, colorless, no particulates | — | clear, colorless, no particulates |
| 47 | clear, colorless, no particulates | clear, colorless, no particulates | clear, colorless, less than 3 particulates | clear, colorless, no particulates | clear, colorless, no particulates |
| 48 | clear, colorless, no particulates | clear, colorless, no particulates | clear, colorless, no particulates | — | clear, colorless, no particulates |
| 37 | clear, colorless, no particulates | clear, colorless, no particulates | clear, colorless, no particulates | clear, colorless, no particulates | clear, colorless, no particulates |
| 49 | clear, colorless, no particulates | clear, colorless, less than 3 particulates | clear, colorless, no particulates | — | clear, colorless, no particulates |
| 50 | clear, colorless, no particulates | clear, colorless, less than 3 particulates | clear, colorless, less than 3 particulates | — | clear, colorless, no particulates |
| 51 | clear, colorless, no particulates | clear, colorless, no particulates | clear, colorless, no particulates | — | clear, colorless, no particulates |
| 52 | clear, colorless, no particulates | clear, colorless, no particulates | clear, colorless, less than 3 particulates | — | clear, colorless, no particulates |
| 53 | clear, colorless, no particulates | clear, colorless, no particulates | clear, colorless, no particulates | — | clear, colorless, no particulates |

TABLE 28-continued

Visual Evaluations of Formulations from Table 25 after Storage at 40° C.:

| No. | Initial | 8 weeks 40° C. | 13 weeks 40° C. | 18 weeks 40° C. | 24 weeks 40° C. |
|---|---|---|---|---|---|
| 54 | clear, colorless, no particulates | clear, colorless, no particulates | clear, colorless, less than 3 particulates | — | clear, colorless, no particulates |

*Y6 and Y4 are color scale notations on the EP Yellow scale. Y6 being less yellow than Y4. (Ref: PhEur 5.0, 2005 Monograph 2.2.2).

The results in Tables 26 through 28 indicate that antibody 11.2.1 formulations containing all tested EDTA concentrations had reduced discoloration, reduced turbidity, and reduced particulate formation as compared to those formulations without EDTA.

Overall, formulations containing sodium chloride had reduced freeze/thaw protection as evidenced by increased discoloration, turbidity, and particulate formation as compared to formulations having EDTA, but without sodium chloride.

Aggregation Analysis:

The antibody formulations prepared according to Table 25 were stored at a temperature of 25° C. and 40° C. At weeks, 0 (initial), 4, 8, 13, 18 and 24, the 25° C. and 40° C. formulations were analyzed for aggregation using size exclusion chromatography. The formulation vials were aseptically sampled at each time point. The size exclusion chromatography was carried out on the samples using a TSKgel® G3000SWXL-G2000SWXL column, mobile phase 0.2 M sodium phosphate buffer at pH 7.0, a flow rate of 1 ml/min, and UV detection at 214 nm. Table 29(a) shows the percentage of antibody 11.2.1 aggregation measured after storage at 25° C. at the relevant times for each of the formulations. Table 29(b) shows the percentage of antibody 11.2.1 aggregation measured after storage at 40° C. Aggregation levels were calculated by integrating the areas under the chromatogram peaks for each formulation and reporting the integrated areas under the high molecular weight species peaks as a percentage of total peak area (see Tables 29(a) and 29(b)).

TABLE 29(a)

Percent Aggregation for Formulations in Table 25 after Storage at 25° C.:

| No. | Initial | 4 weeks 25° C. | 8 weeks 25° C. | 13 weeks 25° C. | 18 weeks 25° C. | 24 weeks 25° C. |
|---|---|---|---|---|---|---|
| 26 | 0.8% | — | — | 1.1% | 1.6% | — |
| 40 | 0.7% | — | — | 0.7% | 0.8% | 0.8% |
| 45 | 0.7% | 0.6% | 0.6% | 0.6% | 0.7% | 0.7% |
| 46 | 0.7% | — | — | 0.6% | 0.7% | 0.7% |
| 47 | 0.7% | 0.7% | 0.6% | 0.6% | 0.7% | 0.7% |
| 48 | 0.7% | | | 0.6% | 0.7% | 0.7% |
| 37 | 0.7% | 0.6% | 0.6% | 0.6% | 0.7% | 0.7% |
| 49 | 0.7% | — | — | 0.6% | — | — |
| 50 | 0.7% | — | — | 0.6% | — | — |
| 51 | 0.7% | — | — | 0.6% | — | 0.7% |
| 52 | 0.7% | 0.6% | 0.6% | 0.6% | — | — |
| 53 | 0.7% | 0.6% | 0.6% | 0.6% | — | 0.7% |
| 54 | 0.7% | 0.6% | 0.6% | 0.6% | — | — |

Table 29(b) below reports the aggregation data that is graphically presented in FIG. 5.

TABLE 29(b)

Percent Aggregation for Formulations in Table 25 after Storage at 40° C.:

| No. | Initial | 4 weeks 40° C. | 8 weeks 40° C. | 13 weeks 40° C. | 18 weeks 40° C. | 24 weeks 40° C. |
|---|---|---|---|---|---|---|
| 26 | 0.8% | — | 3.1% | 4.3% | 5.2% | — |
| 40 | 0.7% | — | 0.9% | 1.2% | 1.8% | 2.7% |
| 45 | 0.7% | 0.6% | 0.8% | 0.8% | 1.0% | 1.4% |
| 46 | 0.7% | — | 0.7% | 0.8% | 1.0% | 1.3% |
| 47 | 0.7% | 0.6% | 0.7% | 0.8% | 0.8% | 1.1% |
| 48 | 0.7% | — | 0.7% | 0.8% | 0.9% | 1.3% |
| 37 | 0.7% | 0.7% | 0.7% | 0.8% | 1.0% | 1.1% |
| 49 | 0.7% | — | 0.8% | 0.8% | — | — |
| 50 | 0.7% | — | 0.7% | 0.8% | — | — |
| 51 | 0.7% | — | 0.8% | 0.8% | — | 1.2% |
| 52 | 0.7% | 0.6% | 0.7% | 0.8% | — | — |
| 53 | 0.7% | 0.7% | 0.7% | 0.7% | — | 1.2% |
| 54 | 0.7% | 0.6% | 0.8% | 0.7% | — | — |

Figure 5:
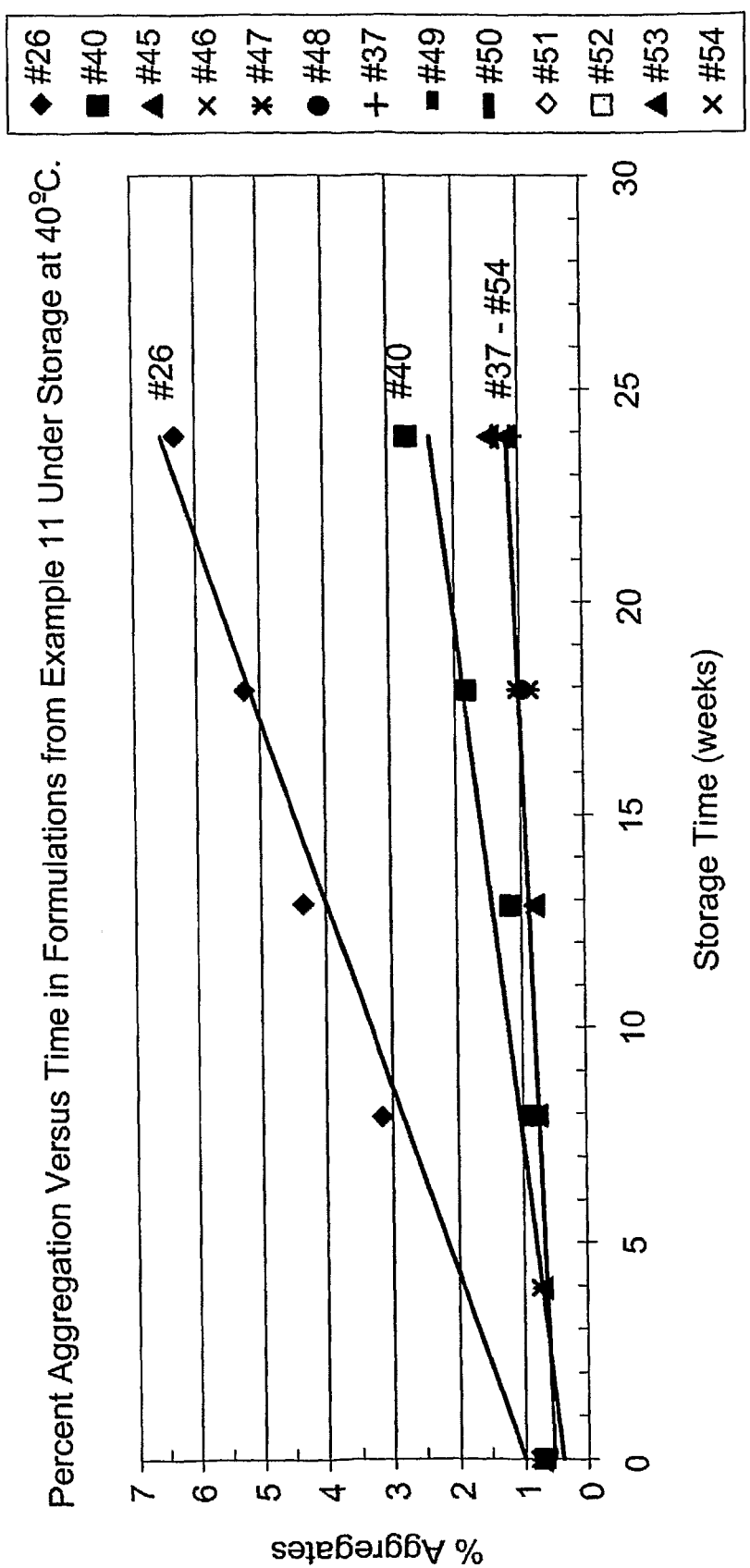
FIG. 5 is a line graph that shows the percent aggregation in various test formulations on storage under accelerated conditions at 40° C. for up to 24 weeks by SEC.
Figure 7:
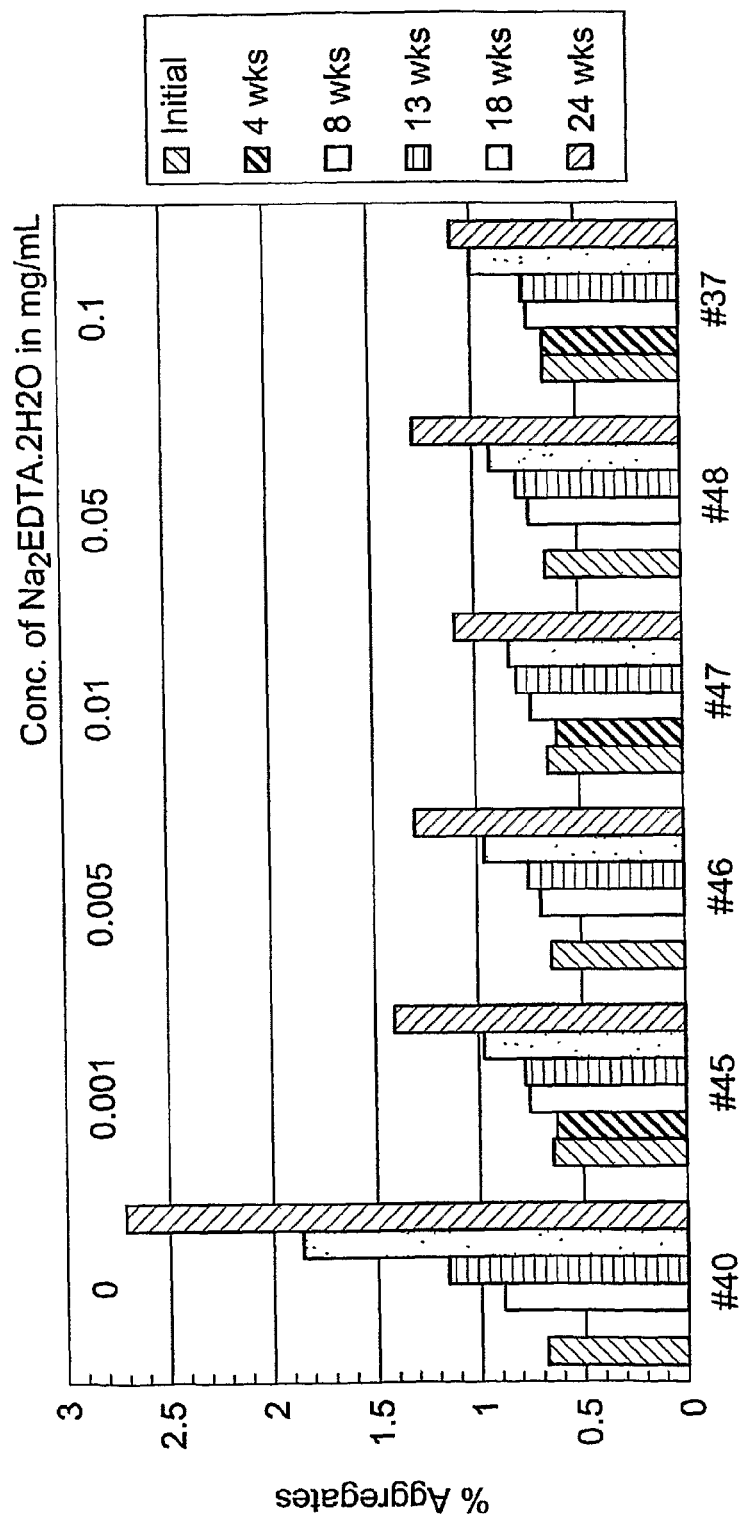
FIG. 7 is a bar graph that shows the percent aggregation in various test formulations as a function of EDTA level on storage under accelerated conditions at 40° C. for up to 24 weeks by SEC.

As can be seen in Tables 29(a), 29(b) and FIG. 5, the EDTA-containing formulations showed reduced levels of aggregation at all tested EDTA concentrations as compared to a formulation lacking EDTA, but having an acetate buffer and sodium chloride, after storage at 25° C. and 40° C. FIG. 7 graphically summarizes the reduction in percent aggregation for the formulations from Table 25 as a function of EDTA concentration.

Fragmentation Analysis:

The antibody formulations prepared according to Table 25 were stored at a temperature of 25° C. and 40° C. At weeks, 0 (initial), 4, 8, 13, 18 and 24, the 25° C. and 40° C. formulations were analyzed for total hydrolytic impurities (i.e., fragmentation) using reduced SDS-PAGE (rSDS-PAGE). The formulation vials were aseptically sampled at each time point and loaded onto NuPAGE® 4-12% bis-Tris gels with colloidal blue (Coomassie) stain. Gel reduction was achieved by use of the NuPAGE® reducing agent. The percentage impurity (i.e., fragmentation) of each sample band in the reduced gels was estimated by scanning on either a Molecular Dynamics Personal Densitometer PDQC-90 or Bio-Rad GS800 Imaging Densitometer. Fragmentation level was calculated as a percentage of total band volume (see Tables 30(a) and 30(b)).

TABLE 30(a)

Percent Fragmentation for Formulations in Table 25 after Storage at 25° C.:

| No. | Initial | 4 weeks 25° C. | 8 weeks 25° C. | 13 weeks 25° C. | 18 weeks 25° C. | 24 weeks 25° C. |
|---|---|---|---|---|---|---|
| 26 | 1.3% | — | — | 3.3% | 3.7% | — |
| 40 | 1.1% | — | — | 2.6% | 3.1% | 3.1% |
| 45 | 1.5% | 2.7% | 2.3% | 3.1% | 3.0% | 3.4% |
| 46 | 1.0% | — | — | 2.5% | 3.1% | 2.9% |
| 47 | 2.5% | 2.5% | 2.3% | 3.1% | 3.0% | 3.3% |
| 48 | 3.1% | — | — | 2.5% | 3.2% | 2.9% |

TABLE 30(a)-continued

Percent Fragmentation for Formulations in Table 25 after Storage at 25° C.:

| No. | Initial | 4 weeks 25° C. | 8 weeks 25° C. | 13 weeks 25° C. | 18 weeks 25° C. | 24 weeks 25° C. |
|---|---|---|---|---|---|---|
| 37 | 3.6% | 2.6% | 2.3% | 3.1% | 3.0% | 3.3% |
| 49 | 1.0% | — | — | 2.6% | — | — |
| 50 | 1.1% | — | — | 2.7% | — | — |
| 51 | 1.2% | — | — | 2.7% | — | 2.9% |
| 52 | 2.4% | 2.7% | 2.3% | 3.1% | — | — |
| 53 | 1.6% | 2.4% | 2.3% | 2.9% | — | 3.4% |
| 54 | 1.6% | 2.7% | 2.2% | 3.2% | — | — |

Table 30(b) below reports the fragmentation data that is graphically presented in FIG. 6.

TABLE 30(b)

Percent Fragmentation for Formulations in Table 25 after Storage at 40° C.:

| No. | Initial | 4 weeks 40° C. | 8 weeks 40° C. | 13 weeks 40° C. | 18 weeks 40° C. | 24 weeks 40° C. |
|---|---|---|---|---|---|---|
| 26 | — | — | 6.2% | 7.3% | 8.7% | 10.1% |
| 40 | — | — | 3.9% | 6.9% | 8.2% | 7.2% |
| 45 | — | 2.9% | 4.3% | 4.2% | 6.7% | 6.7% |
| 46 | — | — | 4.1% | 5.6% | 7.1% | 6.1% |
| 47 | — | 1.9% | 2.8% | 3.4% | 5.4% | 5.6% |
| 48 | — | — | 2.0% | 4.2% | 5.0% | 4.0% |
| 37 | — | 0.7% | 1.5% | 2.2% | 5.0% | 4.5% |
| 49 | — | — | 4.1% | 5.8% | — | — |
| 50 | — | — | 3.7% | 5.5% | — | — |
| 51 | — | — | 3.7% | 5.5% | — | 5.4% |
| 52 | — | 1.8% | 2.4% | 3.1% | — | — |
| 53 | — | 2.4% | 3.3% | 4.1% | — | 6.6% |
| 54 | — | 2.3% | 3.1% | 3.8% | — | — |

Figure 6:
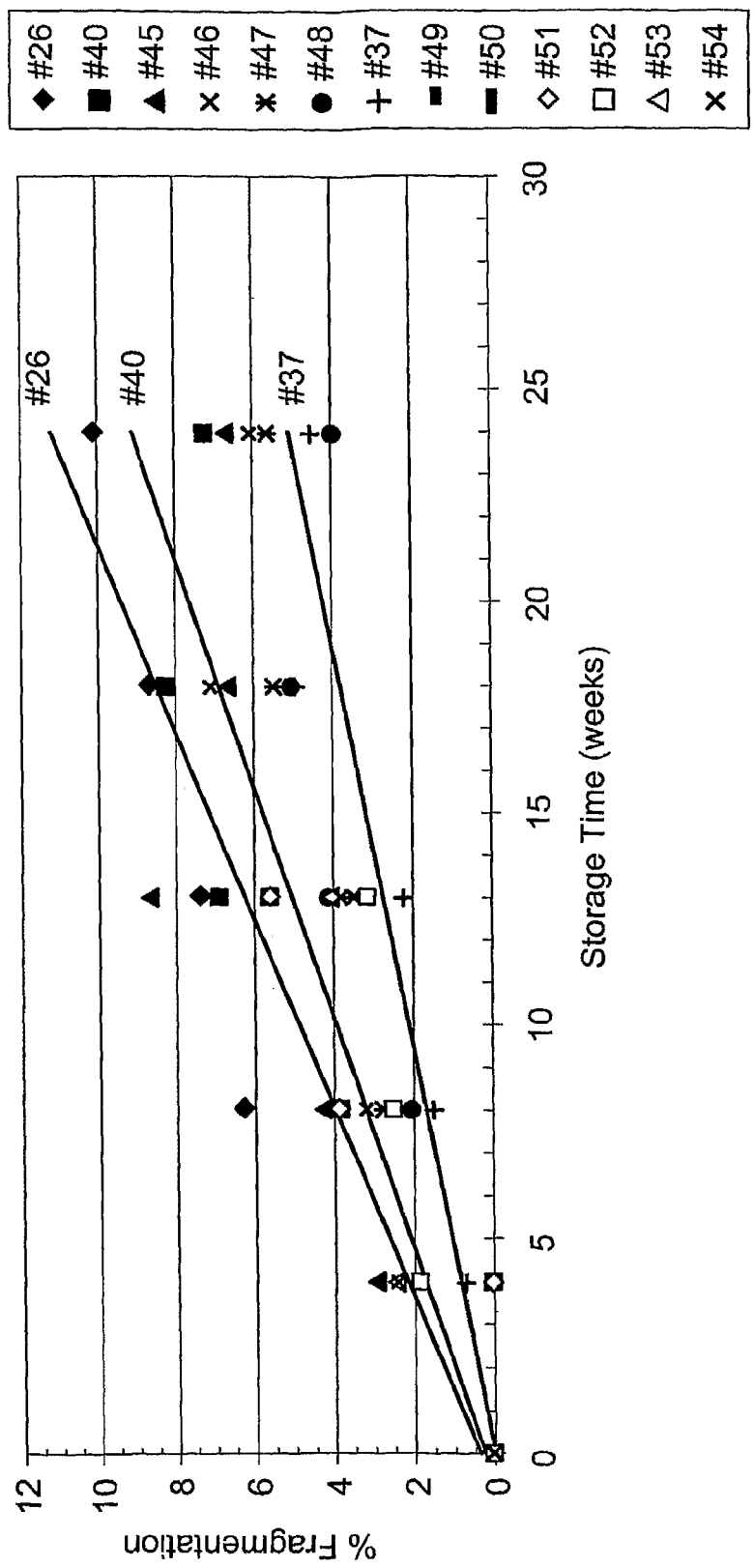
FIG. 6 is a line graph that shows the percent total (hydrolytic) impurities formation in various test formulations on storage under accelerated conditions at 40° C. for up to 24 weeks by rSDSPAGE.

As can be seen in Tables 30(a), 30(b) and FIG. 6, the EDTA-containing formulations showed reduced levels of fragmentation as compared to a formulation lacking EDTA, but having an acetate buffer and sodium chloride, after storage at 25° C. and 40° C. In addition, the formulations containing histidine and trehalose without EDTA showed reduced fragmentation over the formulation containing sodium chloride without EDTA.

Figure 8:
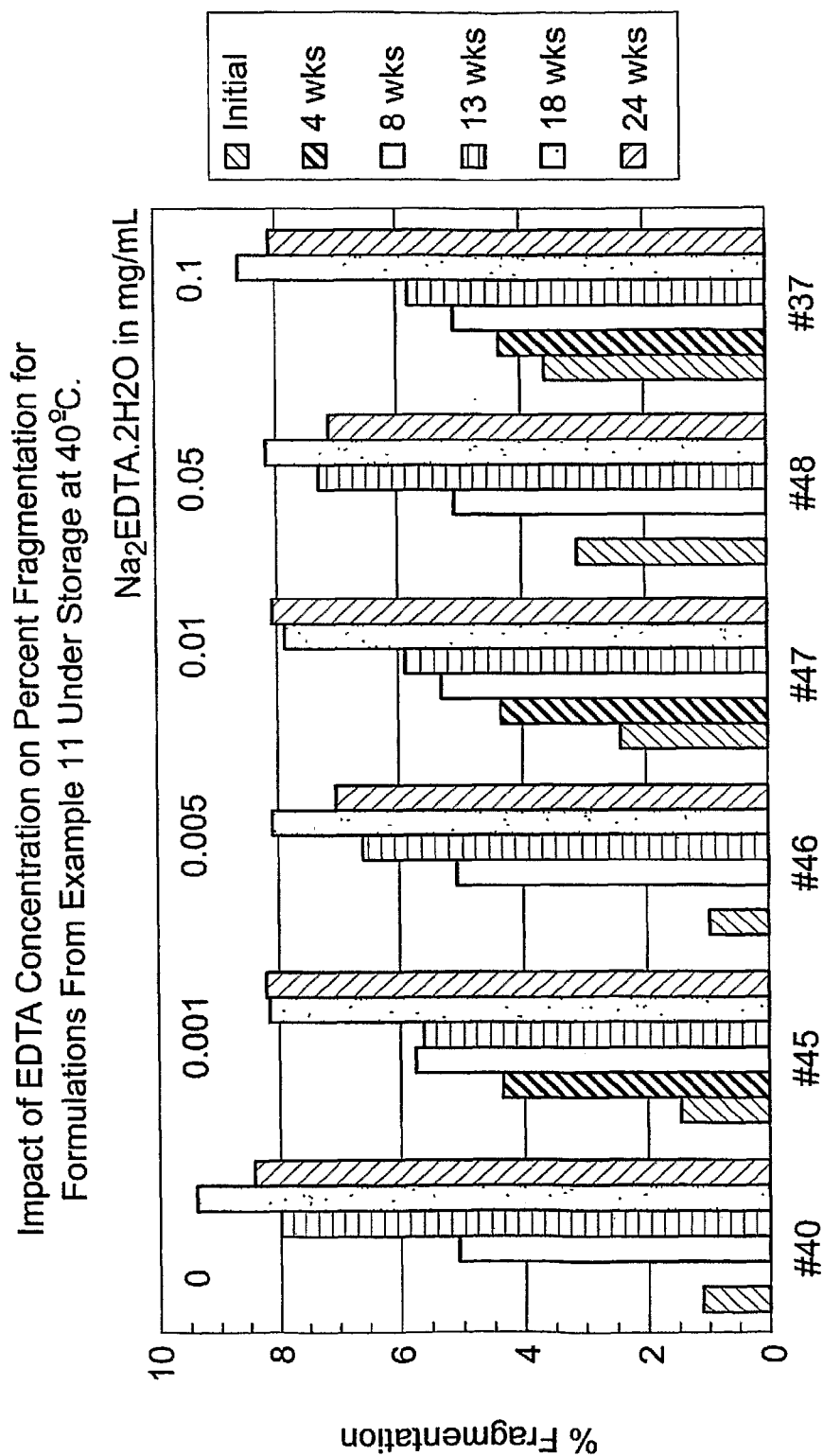
FIG. 8 is a bar graph that shows the percent total (hydrolytic) impurities formation in various test formulations as a function of EDTA level on storage under accelerated conditions at 40° C. for up to 24 weeks by rSDSPAGE.

FIG. 8 graphically summarizes the reduction in percent fragmentation for the formulations from Table 25 as a function of EDTA concentration.

Amino Acid Oxidation Analysis:

Oxidation levels of certain methionine residues at amino acid positions 256 and 432 in the anti-CTLA-4 antibody 11.2.1 were measured by a Lysine-C mapping method. The vials containing the formulations from Table 25 were aseptically sampled at the 18 week and 24 week time points after storage at 40° C. The samples were then digested with a Lysyl Endopeptidase (Lys-C) enzyme in tris buffer at pH 8.0 under standard conditions and analyzed by reversed-phase high performance liquid chromatography. Separation was accomplished using a Grace Vydac® Protein C4 analytical column with 0.1% TFA in water and 0.085% TFA in Acetonitrile gradient elution. Table 31 reports the results.

TABLE 31

Percent Oxidation of Methionine Amino Acids in Anti-CTLA-4 antibody 11.2.1 in Formulations from Table 25:

| No. | Amino Acid Residue | Initial | 18 weeks | 24 weeks |
|---|---|---|---|---|
| 26 | Met 432 | 1.6% | 5.5% | 6.9% |
|    | Met 256 | 5%   | 12.8% | 13.6% |
| 40 | Met 432 | 1.6% | 5.6% | 8.8% |
|    | Met 256 | 5%   | 14.0% | 16.1% |
| 45 | Met 432 | 1.6% | 4.8% | 6.2% |
|    | Met 256 | 5%   | 11.6% | 12.8% |
| 46 | Met 432 | 1.6% | 3.5% | 6.1% |
|    | Met 256 | 5%   | 8.8%  | 12.5% |
| 47 | Met 432 | 1.6% | 3.4% | 4.2% |
|    | Met 256 | 5%   | 8.4%  | 8.3% |
| 48 | Met 432 | 1.6% | 2.8% | 5.7% |
|    | Met 256 | 5%   | 7.6%  | 12.6% |
| 37 | Met 432 | 1.6% | 4.5% | 4.7% |
|    | Met 256 | 5%   | 11.0% | 9.4% |

As can be seen in Table 31, the presence of EDTA in the antibody 11.2.1 formulation reduces the level of methionine oxidation that occurs over time.

Example 12

A study was conducted to compare the effect mannitol and sorbitol on stability of anti-CTLA-4 antibody 11.2.1 formulations. In this Example, alternatives to a histidine-trehalose formulation were tested, by replacing part of the trehalose with varying concentrations of mannitol and/or sorbitol (Table 32). EDTA concentrations (as $Na_2EDTA \cdot 2H_2O$) were examined in the range of 0 to 0.1 mg/ml.

Specifically, the impact on antibody 11.2.1 stability was analyzed with regards to discolocation, aggregation, fragmentation, and oxidation.

The formulations that were evaluated are listed in Table 32 below. The procedure used to prepare the formulations is the same as the one described in Example 10.

The formulations in Table 32 were prepared by taking an 11.9 mg/ml stock solution of antibody 11.2.1 in 20 mM sodium acetate buffer pH 5.5, 140 mM sodium chloride and subjecting it to an ultrafiltration/diafiltration (UF/DF) step in a Millipore Lab Scale™ TFF System with a Pellicon® XL PBTK 30K 50 cm² membrane. Next, concentrated solutions of the antibody 11.2.1 were prepared in the 35 to 40 mg/ml range in 20 mM sodium acetate or 20 mM histidine buffers.

Concentrates of the tonicifying agent were prepared in either the sodium acetate or histidine buffer at three times the target final concentrations. A concentrated solution of polysorbate 80 was prepared at 20 mg/ml and $Na_2EDTA \cdot 2H_2O$ at 10 mg/ml in each of the buffers. Individual formulations were prepared by diluting the concentrated solutions appropriately. The formulations were then filtered through 0.2μ sterilizing grade filters and filled into several duplicate vials. A fill-volume of 1 ml was used in 2 ml Type 1 glass vials.

The vials were closed with Daikyo 777-1 Fluorotec® coated stoppers, crimp sealed, and stored upright in stability chambers at 25° C. and 40° C. Another set of vials was subject to 4× freeze/thaw cycles as described in Example 10. All formulations had a pH of 5.5 and an anti-CTLA-4 antibody 11.2.1 concentration of 20 mg/ml.

Several vials were immediately analyzed for levels of discoloration, aggregation, fragmentation, and oxidation and several other duplicate vials were also stored upright at 25° C. and 40° C. for 4, 8, 13, 18 and 24 weeks. At each time point, two stored vials per formulation were removed from each condition to measure the level of antibody 11.2.1 aggregation, fragmentation, and observed for discoloration as well. Tables 33 to 37 and FIGS. 10 to 11 report the results.

TABLE 32

Antibody Formulations Tested:

| No. | Sodium Acetate (mM) | Histidine (mM) | Tween 80 (mg/ml) | Mannitol (mg/ml) | Sorbitol (mg/ml) | EDTA (mg/ml) | Sodium Chloride (mg/ml) |
|---|---|---|---|---|---|---|---|
| 26 | 20 | — | 0.2 | — | — | — | 8.4 |
| 55 | — | 20 | 0.2 | — | 45 | 0.001 | — |
| 56 | — | 20 | 0.2 | — | 45 | 0.01 | — |
| 57 | — | 20 | 0.2 | — | 45 | 0.1 | — |
| 58 | — | 20 | 0.2 | 5 | 40 | 0.001 | — |
| 59 | — | 20 | 0.2 | 5 | 40 | 0.01 | — |
| 60 | — | 20 | 0.2 | 5 | 40 | 0.1 | — |
| 61 | — | 20 | 0.2 | 15 | 30 | 0.001 | — |
| 62 | — | 20 | 0.2 | 15 | 30 | 0.01 | — |
| 63 | — | 20 | 0.2 | 15 | 30 | 0.1 | — |

Formulation Appearance Analysis:

Each formulation was visually evaluated after 1) initially mixing the formulation, 2) after 4 freeze/thaw cycles (−70° C. to 5° C. along with water-filled vials in box from Example 4) and 3) after storage at 25° C. and 40° C. for 8, 13, and 24 weeks. The formulations were evaluated for particulate formation, color changes and turbidity changes and reported in Tables 33 to 35.

TABLE 33

Visual Evaluations of Formulations from Table 32 after Freeze/Thawing:

| No. | Initial | After 4X Freeze/Thaw Cycles |
|---|---|---|
| 26 | clear, colorless, no particulates | very slightly cloudy, no particulates |
| 55 | clear, colorless, no particulates | clear, colorless, less than 3 particulates |
| 56 | clear, colorless, no particulates | clear, colorless, less than 3 particulates |
| 57 | clear, colorless, no particulates | clear, colorless, no particulates |
| 58 | clear, colorless, no particulates | clear, colorless, less than 3 particulates |
| 59 | clear, colorless, no particulates | clear, colorless, less than 3 particulates |
| 60 | clear, colorless, no particulates | clear, colorless, less than 3 particulates |
| 61 | clear, colorless, no particulates | clear, colorless, no particulates |
| 62 | clear, colorless, no particulates | clear, colorless, no particulates |
| 63 | clear, colorless, no particulates | clear, colorless, no particulates |

TABLE 34

Visual Evaluations of Formulations from Table 32 after Storage at 25° C.:

| No. | Initial | 13 weeks 25° C. | 24 weeks 25° C. |
|---|---|---|---|
| 26 | clear, colorless, no particulates | clear, colorless, no particulates | — |
| 55 | clear, colorless, no particulates | clear, colorless, less than 3 particulates | clear, colorless, no particulates |
| 56 | clear, colorless, no particulates | clear, colorless, less than 3 particulates | clear, colorless, no particulates |
| 57 | clear, colorless, no particulates | clear, colorless, less than 3 particulates | clear, colorless, no particulates |
| 58 | clear, colorless, no particulates | clear, colorless, no particulates | clear, colorless, no particulates |
| 59 | clear, colorless, no particulates | clear, colorless, no particulates | clear, colorless, no particulates |
| 60 | clear, colorless, no particulates | clear, colorless, no particulates | clear, colorless, no particulates |
| 61 | clear, colorless, no particulates | clear, colorless, no particulates | clear, colorless, no particulates |
| 62 | clear, colorless, no particulates | clear, colorless, no particulates | clear, colorless, no particulates |
| 63 | clear, colorless, no particulates | clear, colorless, no particulates | clear, colorless, no particulates |

TABLE 35

Visual Evaluations of Formulations from Table 25 after Storage at 40° C.:

| No. | Initial | 8 weeks 40° C. | 13 weeks 40° C. | 24 weeks 40° C. |
|---|---|---|---|---|
| 26 | clear, colorless, no particulates | very slightly pink, no particulates | very slightly pink, no particulates | pink, no particulates |
| 55 | clear, colorless, no particulates | clear, colorless, no particulates | clear, colorless, no particulates | clear, colorless, no particulates |
| 56 | clear, colorless, no particulates | clear, colorless, no particulates | clear, colorless, no particulates | clear, colorless, no particulates |
| 57 | clear, colorless, no particulates | clear, colorless, less than 3 particulates | clear, colorless, less than 3 particulates | clear, colorless, no particulates |
| 58 | clear, colorless, no particulates | clear, colorless, no particulates | clear, colorless, less than 3 particulates | clear, colorless, no particulates |
| 59 | clear, colorless, no particulates | clear, colorless, less than 3 particulates | clear, colorless, no particulates | clear, colorless, no particulates |

TABLE 35-continued

Visual Evaluations of Formulations from Table 25 after Storage at 40° C.:

| No. | Initial | 8 weeks 40° C. | 13 weeks 40° C. | 24 weeks 40° C. |
|---|---|---|---|---|
| 60 | clear, colorless, no particulates | clear, colorless, less than 3 particulates | clear, colorless, no particulates | clear, colorless, no particulates |
| 61 | clear, colorless, no particulates | clear, colorless, no particulates | clear, colorless, less than 3 particulates | clear, colorless, no particulates |
| 62 | clear, colorless, no particulates | clear, colorless, less than 3 particulates | clear, colorless, no particulates | clear, colorless, no particulates |
| 63 | clear, colorless, no particulates | clear, colorless, no particulates | clear, colorless, no particulates | clear, colorless, no particulates |

The results in Tables 33 through 35 indicate that antibody 11.2.1 formulations containing sodium chloride, but without EDTA, had reduced freeze/thaw protection as evidenced by increased discoloration, turbidity, and particulate formation as compared to formulations having EDTA, but without sodium chloride. The results also indicate that antibody 11.2.1 formulations containing all tested EDTA concentrations had reduced discoloration, reduced turbidity, and reduced particulate formation as compared to formulations without EDTA.

Aggregation Analysis:

The antibody formulations prepared according to Table 32 were stored at a temperature of 25° C. and 40° C. At weeks, 0 (initial), 4, 8, 13, 18 and 24, the 25° C. and 40° C. formulations were analyzed for aggregation using size exclusion chromatography. The formulation vials were aseptically sampled at each time point. The size exclusion chromatography was carried out on the samples using a TSKgel® G3000SWXL-G2000SWXL column, mobile phase 0.2 M sodium phosphate buffer at pH 7.0, a flow rate of 1 ml/min, and UV detection at 214 nm. Table 36(a) shows the percentage of antibody 11.2.1 aggregation measured after storage at 25° C. at the relevant times for each of the formulations. Table 36(b) shows the percentage of antibody 11.2.1 aggregation measured after storage at 40° C. Aggregation levels were calculated by integrating the areas under the chromatogram peaks for each formulation and reporting the integrated areas under the high molecular weight species peaks as a percentage of total peak area (see Tables 36(a) and 36(b)).

TABLE 36(a)

Percent Aggregation for Formulations in Table 32 after Storage at 25° C.:

| No. | Initial | 4 weeks 25° C. | 8 weeks 25° C. | 13 weeks 25° C. | 18 weeks 25° C. | 24 weeks 25° C. |
|---|---|---|---|---|---|---|
| 26 | 0.8% | — | — | 1.1% | 1.6% | — |
| 55 | 0.7% | 0.6% | 0.6% | 0.6% | — | — |
| 56 | 0.7% | 0.6% | 0.7% | 0.6% | — | — |
| 57 | 0.7% | 0.6% | 0.6% | 0.6% | — | 0.7% |
| 58 | 0.7% | — | — | 0.6% | — | — |
| 59 | 0.7% | — | — | 0.6% | — | — |
| 60 | 0.7% | — | — | 0.6% | — | — |
| 61 | 0.7% | 0.7% | 0.6% | 0.6% | — | — |
| 62 | 0.7% | 0.6% | 0.6% | 0.6% | — | — |
| 63 | 0.7% | 0.6% | 0.8% | 0.6% | — | — |

Table 36(b) below reports the aggregation data that is graphically presented in FIG. 9.

TABLE 36(b)

Percent Aggregation for Formulations in Table 32 after Storage at 40° C.:

| No. | Initial | 4 weeks 40° C. | 8 weeks 40° C. | 13 weeks 40° C. | 18 weeks 40° C. | 24 weeks 40° C. |
|---|---|---|---|---|---|---|
| 26 | 0.8% | 3.1% | 4.3% | 5.2% | 6.4% | — |
| 55 | 0.6% | 0.7% | 0.8% | 0.8% | — | — |
| 56 | 0.6% | 0.7% | 0.8% | 0.7% | — | — |
| 57 | 0.7% | 0.7% | 0.8% | 0.8% | — | 1.2% |
| 58 | 0.7% | — | 0.8% | 0.8% | — | — |
| 59 | 0.7% | — | 0.8% | 0.8% | — | — |
| 60 | 0.6% | — | 0.7% | 0.8% | — | — |
| 61 | 0.7% | 0.7% | 0.7% | 0.8% | — | — |
| 62 | 0.6% | 0.7% | 0.8% | 0.8% | — | — |
| 63 | 0.7% | 0.7% | 0.7% | 0.8% | — | — |

Figure 9:
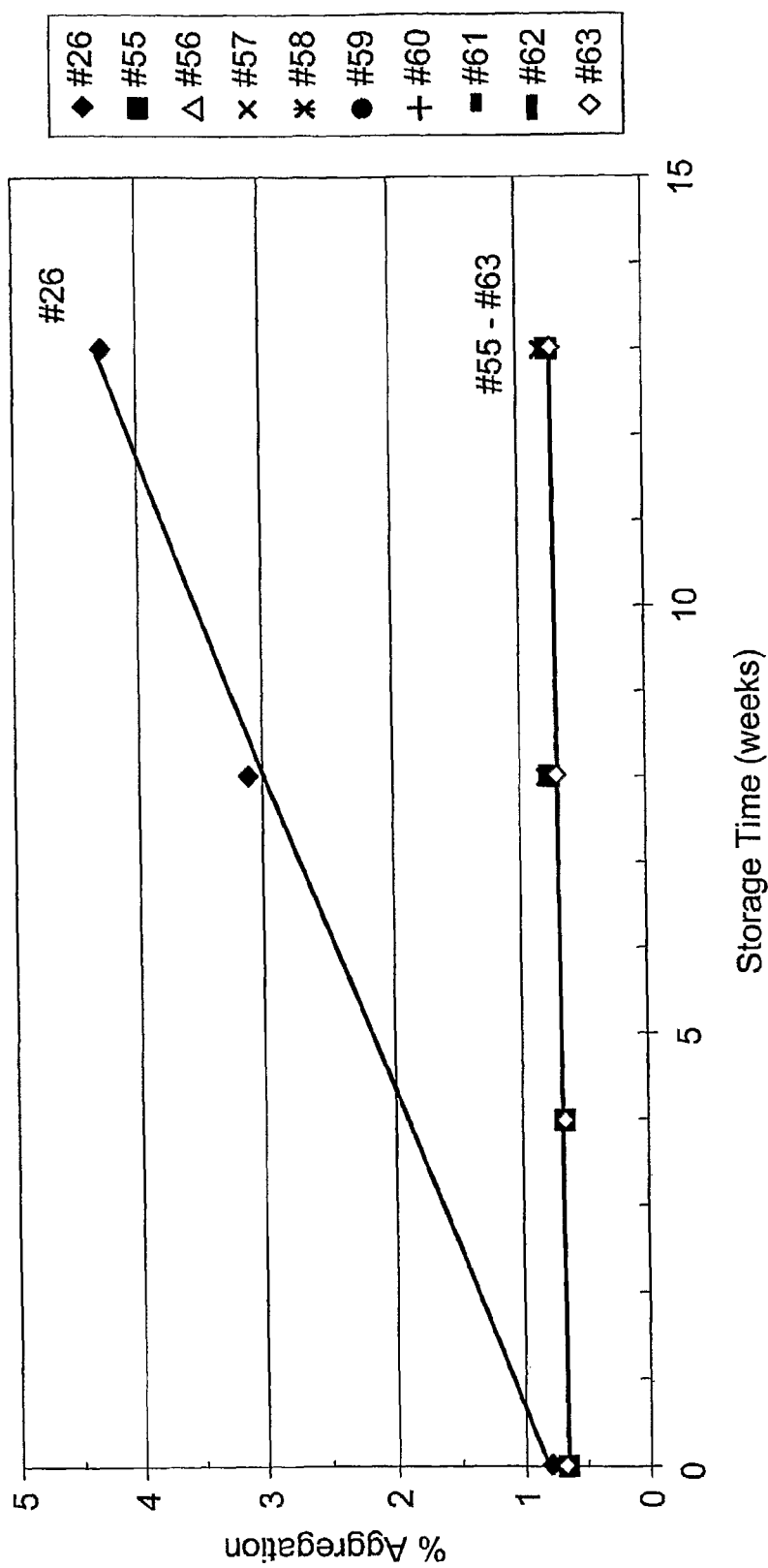
FIG. 9 is a line graph that shows the percent aggregation in various test formulations from on storage under accelerated conditions at 40° C. for up to 13 weeks by SEC.

As can be seen in Tables 36(a), 36(b) and FIG. 9, the EDTA-containing formulations showed reduced levels of aggregation at all tested EDTA concentrations as compared to a formulation lacking EDTA, but having an acetate buffer and sodium chloride (i.e., chloride ions), after storage at 25° C. and 40° C. FIG. 9 graphically summarizes the reduction in percent aggregation for the formulations from Table 32.

Fragmentation Analysis:

The antibody formulations prepared according to Table 32 were stored at a temperature of 25° C. and 40° C. At weeks, 0 (initial), 4, 8, 13, 18 and 24, the 25° C. and 40° C. formulations were analyzed for total hydrolytic impurities (i.e., fragmentation) using reduced SDS-PAGE (rSDS-PAGE). The formulation vials were aseptically sampled at each time point and loaded onto NuPAGE® 4-12% bis-Tris gels with colloidal blue (Coomassie) stain. Gel reduction was achieved by use of the NuPAGE® reducing agent. The percentage impurity (i.e., fragmentation) of each sample band in the reduced gels was estimated by scanning on either a Molecular Dynamics Personal Densitometer PDQC-90 or Bio-Rad GS800 Imaging Densitometer. Fragmentation level was calculated as a percentage of total band volume (see Tables 37(a) and 37(b)).

TABLE 37(a)

Percent Fragmentation for Formulations in Table 32 after Storage at 25° C.:

| No. | Initial | 4 weeks 25° C. | 8 weeks 25° C. | 13 weeks 25° C. | 18 weeks 25° C. | 24 weeks 25° C. |
|---|---|---|---|---|---|---|
| 26 | 1.3% | — | — | 3.3% | 3.7% | — |
| 55 | 1.6% | — | — | 2.9% | — | — |
| 56 | 1.6% | — | — | 2.5% | — | — |
| 57 | 1.6% | — | — | 2.4% | — | 2.9% |
| 58 | 1.0% | — | — | 2.5% | — | — |
| 59 | 1.1% | — | — | 2.6% | — | — |

TABLE 37(a)-continued

Percent Fragmentation for Formulations in Table 32 after Storage at 25° C.:

| No. | Initial | 4 weeks 25° C. | 8 weeks 25° C. | 13 weeks 25° C. | 18 weeks 25° C. | 24 weeks 25° C. |
|---|---|---|---|---|---|---|
| 60 | 1.2% | — | — | 2.6% | — | — |
| 61 | 1.1% | — | — | 2.5% | — | — |
| 62 | 1.0% | — | — | 2.5% | — | — |
| 63 | 1.1% | 2.3% | 2.1% | 2.6% | — | — |

Table 37(b) below reports the fragmentation data that is graphically presented in FIG. 10.

TABLE 37(b)

Percent Fragmentation for Formulations in Table 32 after Storage at 40° C.:

| No. | Initial | 4 weeks 40° C. | 8 weeks 40° C. | 13 weeks 40° C. | 18 weeks 40° C. | 24 weeks 40° C. |
|---|---|---|---|---|---|---|
| 26 | — | — | 6.2% | 7.3% | 8.7% | 10.1% |
| 55 | — | 1.6% | 2.3% | 5.7% | — | — |
| 56 | — | 1.9% | 2.3% | 4.8% | — | — |
| 57 | — | 2.0% | 2.6% | 4.7% | — | 5.3% |
| 58 | — | — | 3.7% | 5.6% | — | — |
| 59 | — | — | 3.6% | 5.7% | — | — |
| 60 | — | — | 3.5% | 5.3% | — | — |
| 61 | — | 2.5% | 3.3% | 5.5% | — | — |
| 62 | — | 2.6% | 3.6% | 5.9% | — | — |
| 63 | — | 2.6% | 3.6% | 5.3% | — | — |

Figure 10:
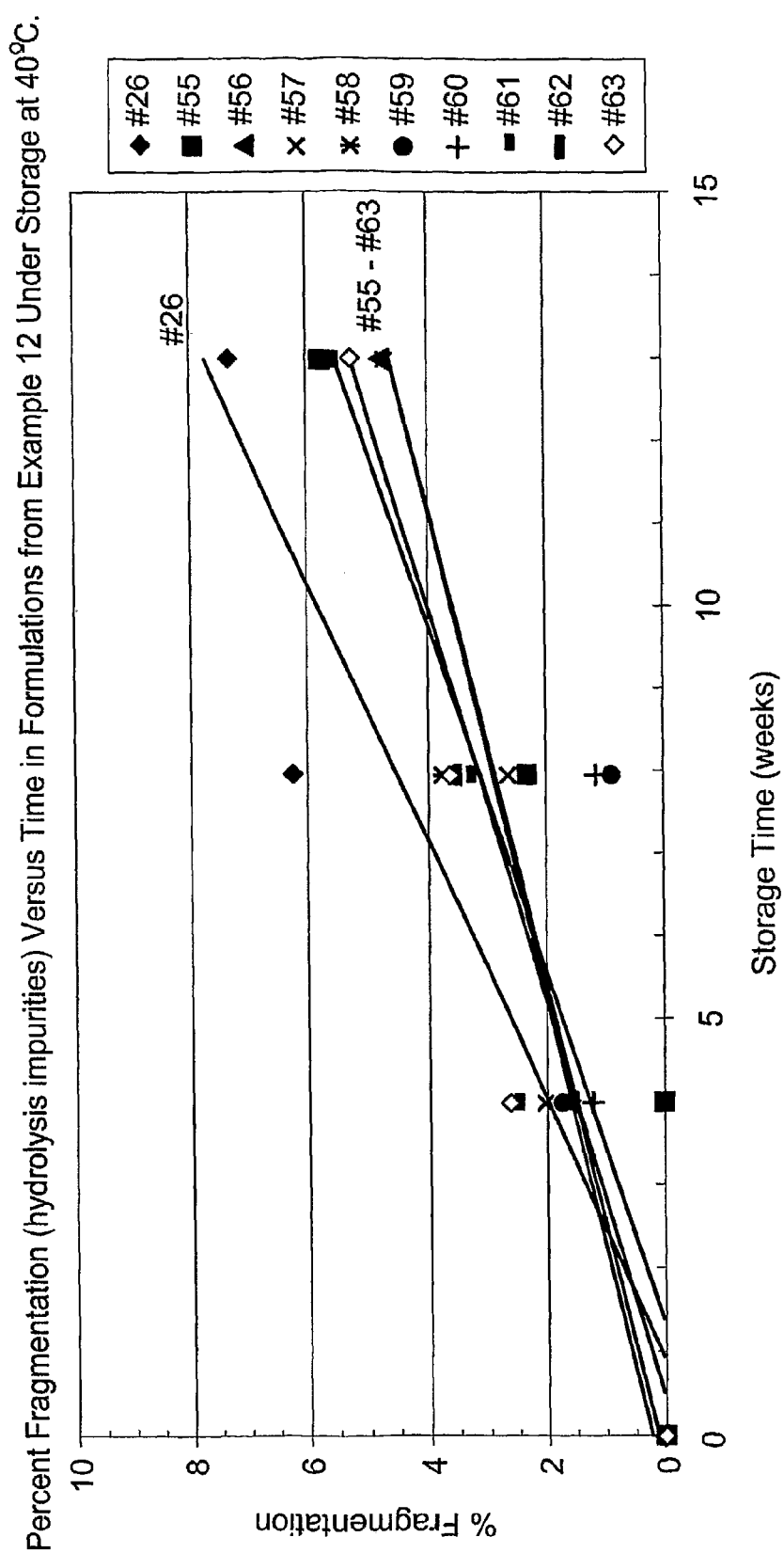
FIG. 10 is a line graph that shows the percent total (hydrolytic) impurities formation in various test formulations from on storage under accelerated conditions at 40° C. for up to 13 weeks by rSDSPAGE.

As can be seen in Tables 37(a), 37(b) and FIG. 10, the EDTA-containing formulations showed reduced levels of fragmentation as compared to a formulation lacking EDTA, but having an acetate buffer and sodium chloride (i.e., chloride ions), after storage at 25° C. and 40° C.

Example 13

This example illustrates the production of a liquid pharmaceutical composition containing anti-CTLA-4 antibody ticilimumab, L-histidine monohydrochloride monohydrate, disodium ethylenediaminetetraacetic acid dihydrate, α α-trehalose dihydrate, and polysorbate 80.

A liquid pharmaceutical composition of the present invention was formed by obtaining the following components: anti-CTLA-4 antibody ticilimumab (available from hybridoma cell line 11.2.1.4 deposited under ATCC Accession No. PTA-5169 according to Example 1 or recombinantly prepared from a mammalian cell line according to Example 2), L-histidine monohydrochloride monohydrate (available from Ajinomoto, Raleigh, N.C.), L-histidine (available from Ajinomoto, Raleigh, N.C.), disodium ethylenediaminetetraacetic acid dihydrate (available as Titriplex III® from Merck KgaA, Darmstadt, Germany), α α-trehalose dihydrate (available as Product Number T-104-1-MC, from Ferro Pfanstiehl, Waukegan Ill.), and polysorbate 80 (available as Crillet 4 HP, from Croda Inc., Mill Hall Pa.).

The liquid pharmaceutical composition was prepared by first preparing several stock solutions of anti-CTLA-4 antibody ticilimumab, L-histidine monohydrochloride monohydrate, disodium ethylenediaminetetraacetic acid dihydrate, α α-trehalose dihydrate, and polysorbate 80. A 20 mM histidine buffer pH 5.5 is prepared by dissolving 3.27 mg/mL (15.6 mM) L-Histidine HCl monohydrate and 0.68 mg/mL (4.4 mM) L-Histidine in water. A 1× Formulation buffer is prepared by dissolving 3.27 mg/mL (15.6 mM) L-Histidine HCl monohydrate and 0.68 mg/mL (4.4 mM) L-Histidine, 84 mg/mL (222 mM) α α-trehalose dihydrate, 0.2 mg/mL Polysorbate 80 and 0.1 mg/mL (0.268 mM) disodium ethylenediaminetetraacetic acid dihydrate in water. A 2× Formulation buffer is prepared by dissolving 3.27 mg/mL (15.6 mM) L-Histidine HCl monohydrate and 0.68 mg/mL (4.4 mM) L-Histidine, 168 mg/mL (444 mM) α α-trehalose dihydrate, 0.4 mg/mL Polysorbate 80 and 0.2 mg/mL (0.536 mM) disodium ethylenediaminetetraacetic acid dihydrate in water. A stock solution of anti-CTLA-4 antibody ticilimumab is prepared according to Example 2 and concentrated to between 42 and 55 mg/ml (target 45 mg/mL) in the Histidine buffer using an ultrafiltration process carried out with a membrane Type 50 kD (Biomax PES).

To prepare the pharmaceutical composition, equal volumes of the concentrated stock solution of anti-CTLA-4 antibody ticilimumab and the 2× Formulation buffer are added to a container suitable for intimate mixing of liquid compositions. After mixing, a small volume of the solution is removed and antibody concentration determined by Ultraviolet-Visible spectrometry (UV-Vis) method using an extinction coefficient of 1.43 (mg/mL)-1 cm$^{-1}$ (expected range 21 to 27.5 mg/mL, target 22.5 mg/mL). Finally, an appropriately calculated volume of 1× Formulation buffer is added and mixed to bring the antibody to the target concentration of 20 mg/mL (range 18-22 mg/mL).

The pharmaceutical compositions is then filtered through 0.2μ sterilizing grade filters and filled into vials. A nominal fill-volume of 20 milliliter was used in 20 milliliter Type 1 glass vials. The vials were closed with Daikyo 777-1 Fluorotec® coated stoppers and crimp sealed. The glass vials were sterilized as were the 20 mm Daikyo 777-1 serum stoppers.

Each single vial unit contains about 400 mg of anti-CTLA-4 antibody ticilimumab, 65.4 mg of L-histidine monohydrochloride monohydrate, 13.6 mg of L-Histidine, 2 mg of disodium ethylenediaminetetraacetic acid dihydrate, 1680 mg of α α-trehalose dihydrate, and 4 mg of polysorbate 80.

Example 14

This example illustrates the prospective production of a liquid pharmaceutical composition containing anti-CTLA-4 antibody ticilimumab, L-histidine monohydrochloride monohydrate, calcium disodium ethylenediaminetetraacetic acid, α α-trehalose dihydrate, and polysorbate 80.

A liquid pharmaceutical composition of the present invention may be formed by obtaining the following components: anti-CTLA-4 antibody ticilimumab (available from hybridoma cell line 11.2.1.4 deposited under ATCC Accession No. PTA-5169 according to Example 1 or recombinantly prepared from a mammalian cell line according to Example 2), L-histidine monohydrochloride monohydrate (available from Ajinomoto, Raleigh, N.C.), L-histidine (available from Ajinomoto, Raleigh, N.C.), calcium disodium ethylenediaminetetraacetic acid (available from Sigma-Aldrich, St. Louis, Mo.), α α-trehalose dihydrate (available as Product Number T-104-1-MC, from Ferro Pfanstiehl, Waukegan Ill.), and polysorbate 80 (available as Crillet 4 HP, from Croda Inc., Mill Hall Pa.).

The liquid pharmaceutical composition may be prepared by first preparing several stock solutions of anti-CTLA-4 antibody ticilimumab, L-histidine monohydrochloride monohydrate, disodium ethylenediaminetetraacetic acid dihydrate, α α-trehalose dihydrate, and polysorbate 80. A 20 mM histidine buffer pH 5.5 may be prepared by dissolving 3.27 mg/mL (15.6 mM) L-Histidine HCl monohydrate and 0.68 mg/mL (4.4 mM) L-Histidine in water. A 1× Formulation buffer may be prepared by dissolving 3.27 mg/mL (15.6 mM) L-Histidine HCl monohydrate and 0.68 mg/mL (4.4 mM) L-Histidine, 84 mg/mL (222 mM) α α-trehalose dihydrate, 0.2 mg/mL Polysorbate 80 and 0.1003 mg/mL (0.268 mM) calcium disodium ethylenediaminetetraacetic acid in water. A 2× Formulation buffer may be prepared by dissolving 3.27 mg/mL (15.6 mM) L-Histidine HCl monohydrate and 0.68 mg/mL (4.4 mM) L-Histidine, 168 mg/mL (444 mM) α α-trehalose dihydrate, 0.4 mg/mL Polysorbate 80 and 0.2006 mg/mL (0.536 mM) calcium disodium ethylenediaminetetraacetic acid in water. A stock solution of anti-CTLA-4 antibody ticilimumab may be prepared according to Example 2 and concentrated to between 42 and 55 mg/ml (target 45 mg/mL) in the Histidine buffer using an ultrafiltration process carried out with a membrane Type 50 kD (Biomax PES).

To prepare the pharmaceutical composition, equal volumes of the concentrated stock solution of anti-CTLA-4 antibody ticilimumab and the 2× Formulation buffer may be added to a container suitable for intimate mixing of liquid compositions. After mixing, a small volume of the solution may be removed and antibody concentration determined by Ultraviolet-Visible spectrometry (UV-Vis) method using an extinction coefficient of 1.43 (mg/mL)$^{-1}$ cm$^{-1}$ (expected range 21 to 27.5 mg/mL, target 22.5 mg/mL). Finally, an appropriately calculated volume of 1× Formulation buffer may be added and mixed to bring the antibody to the target concentration of 20 mg/mL (range 18-22 mg/mL).

The pharmaceutical compositions may then be filtered through 0.2μ sterilizing grade filters and filled into vials. A nominal fill-volume of 20 milliliter may be used in 20 milliliter Type 1 glass vials. The vials may then be closed with Daikyo 777-1 Fluorotec® coated stoppers and crimp sealed. The glass vials may be sterilized as well as the 20 mm Daikyo 777-1 serum stoppers.

Each single vial unit would contain about 400 mg of anti-CTLA-4 antibody ticilimumab, 65.4 mg of L-histidine monohydrochloride monohydrate, 13.6 mg of L-Histidine, 2.006 mg of calcium disodium ethylenediaminetetraacetic acid, 1680 mg of α α-trehalose dihydrate, and 4 mg of polysorbate 80.

Example 15

This example illustrates the prospective production of a liquid pharmaceutical composition containing anti-CTLA-4 antibody ticilimumab, L-histidine monohydrochloride monohydrate, trisodium ethylenediaminetetraacetic acid, α α-trehalose dihydrate, and polysorbate 80.

A liquid pharmaceutical composition of the present invention was formed by obtaining the following components: anti-CTLA-4 antibody ticilimumab (available from hybridoma cell line 11.2.1.4 deposited under ATCC Accession No. PTA-5169 according to Example 1 or recombinantly prepared from a mammalian cell line according to Example 2), L-histidine monohydrochloride monohydrate (available from Ajinomoto, Raleigh, N.C.), L-histidine (available from Ajinomoto, Raleigh, N.C.), trisodium ethylenediaminetetraacetic acid (available from Sigma-Aldrich, St. Louis, Mo.), α α-trehalose dihydrate (available as Product Number T-104-1-MC, from Ferro Pfanstiehl, Waukegan Ill.), and polysorbate 80 (available as Crillet 4 HP, from Croda Inc., Mill Hall Pa.).

The liquid pharmaceutical composition was prepared by first preparing several stock solutions of anti-CTLA-4 antibody ticilimumab, L-histidine monohydrochloride monohydrate, trisodium ethylenediaminetetraacetic acid, α α-trehalose dihydrate, and polysorbate 80. A 20 mM histidine buffer pH 5.5 is prepared by dissolving 3.27 mg/mL (15.6 mM) L-Histidine HCl monohydrate and 0.68 mg/mL (4.4 mM) L-Histidine in water. A 1× Formulation buffer is prepared by dissolving 3.27 mg/mL (15.6 mM) L-Histidine HCl monohydrate and 0.68 mg/mL (4.4 mM) L-Histidine, 84 mg/mL (222 mM) α α-trehalose dihydrate, 0.2 mg/mL Polysorbate 80 and 0.096 mg/mL (0.268 mM) trisodium ethylenediaminetetraacetic acid in water. A 2× Formulation buffer is prepared by dissolving 3.27 mg/mL (15.6 mM) L-Histidine HCl monohydrate and 0.68 mg/mL (4.4 mM) L-Histidine, 168 mg/mL (444 mM) α α-trehalose dihydrate, 0.4 mg/mL Polysorbate 80 and 0.192 mg/mL (0.536 mM) trisodium ethylenediaminetetraacetic acid in water. A stock solution of anti-CTLA-4 antibody ticilimumab is prepared according to Example 2 and concentrated to between 42 and 55 mg/ml (target 45 mg/mL) in the Histidine buffer using an ultrafiltration process carried out with a membrane Type 50 kD (Biomax PES).

To prepare the pharmaceutical composition, equal volumes of the concentrated stock solution of anti-CTLA-4 antibody ticilimumab and the 2× Formulation buffer are added to a container suitable for intimate mixing of liquid compositions. After mixing, a small volume of the solution is removed and antibody concentration determined by Ultraviolet-Visible spectrometry (UV-Vis) method using an extinction coefficient of 1.43 (mg/mL)$^{-1}$ cm$^{-1}$ (expected range 21 to 27.5 mg/mL, target 22.5 mg/mL). Finally, an appropriately calculated volume of 1× Formulation buffer is added and mixed to bring the antibody to the target concentration of 20 mg/mL (range 18-22 mg/mL).

The pharmaceutical compositions is then filtered through 0.2μ sterilizing grade filters and filled into vials. A nominal fill-volume of 20 milliliter was used in 20 milliliter Type 1 glass vials. The vials were closed with Daikyo 777-1 Fluorotec® coated stoppers and crimp sealed. The glass vials were sterilized as were the 20 mm Daikyo 777-1 serum stoppers.

Each single vial unit contains about 400 mg of anti-CTLA-4 antibody ticilimumab, 65.4 mg of L-histidine monohydrochloride monohydrate, 13.6 mg of L-Histidine, 1.92 mg of trisodium ethylenediaminetetraacetic acid, 1680 mg of α α-trehalose dihydrate, and 4 mg of polysorbate 80.

What is claimed is:

1. A composition comprising:
   a chelating agent at a concentration of about 0.01 mM to about 5.0 mM;
   histidine at a concentration of about 1 mM to about 100 mM;
   a surfactant at a concentration of about 0.01 mg/ml to about 10 mg/ml;
   trehalose at a concentration of about 100 mM to about 300 mM; and
   an antibody at a concentration of about 1 mg/ml to about 200 mg/ml, wherein said antibody binds to human CTLA-4 and comprises the heavy chain CDR1, CDR2, and CDR3 amino acid sequences in SEQ ID NO: 2 and the light chain CDR1, CDR2, and CDR3 amino acid sequences in SEQ ID NO: 4.

2. The composition according to claim 1, wherein the antibody is a human IgG antibody.

3. The composition according to claim 1, wherein the antibody comprises a heavy chain amino acid sequence as shown in SEQ ID NO: 2 and a light chain amino acid sequence as shown in SEQ ID NO: 4.

4. The composition according to claim 1, wherein the chelating agent is EDTA, DTPA, or DFM.

5. The composition according to claim 4, wherein the chelating agent is EDTA.

6. The composition according to claim 1, wherein the surfactant is polysorbate 80.

7. The composition according to claim 1, wherein the chelating agent is EDTA and the surfactant is polysorbate 80.

8. The composition according to claim 1, wherein the composition is a liquid composition and has a pH of 5.0-6.5.

9. The composition according to claim 8, wherein the chelating agent is EDTA.

10. The composition according to claim 1, wherein:
    the antibody is at a concentration of about 1 mg/ml to about 100 mg/ml;
    the chelating agent is at a concentration of about 0.01 mM to about 1.0 mM; and
    the composition is a liquid composition with a pH of 5.0-6.5.

11. The composition according to claim 1, wherein the composition comprises:
    the antibody at a concentration of about 1 mg/ml to about 100 mg/ml;
    EDTA at a concentration of about 0.01 mM to about 1.0 mM;
    histidine at a concentration of about 1 mM to about 50 mM;
    polysorbate 80 at a concentration of about 0.01 mg/ml to about 5 mg/ml; and
    trehalose at a concentration of about 100 mM to about 300 mM,
    wherein the composition is a liquid composition with a pH of 5.0-6.5.

12. The composition according to claim 1, wherein the composition comprises:
    about 20 mg/mL antibody;
    about 0.27 mM EDTA;
    about 20 mM histidine;
    about 0.2 mg/mL polysorbate 80; and
    about 222 mM trehalose.

13. The composition according to claim 1, wherein the composition comprises:
    about 20 mg/mL antibody;
    about 0.1 mg/mL EDTA;
    about 20 mM histidine;
    about 0.2 mg/mL polysorbate 80; and
    about 84 mg/mL trehalose, wherein the composition is a liquid composition with a pH of 5.5.

14. The composition according to claim 1, wherein after storage for a period of about 24 weeks at a temperature of about 40° C., an aggregate chromatogram peak area for the composition is at least 2% less than an aggregate chromatogram peak area for an otherwise identical composition that lacks the chelating agent and that is stored under identical conditions.

15. A process for preparing the composition according to claim 1, comprising combining the antibody, the chelating agent, the surfactant, trehalose, and histidine.

16. A method for inhibiting binding between CTLA-4 and B7-1, B7-2 or both in a subject, comprising administering to the subject the composition according to claim 1.

17. The composition according to claim 1, 12, or 13, wherein the antibody comprises the heavy chain variable domain amino acid sequence in SEQ ID NO: 2 and the light chain variable domain amino acid sequence in SEQ ID NO: 4.

18. The method according to claim 16, wherein the subject suffers from a neoplasia condition.

19. The composition according to claim 12 or 13, wherein the antibody is ticilimumab.

20. The method according to claim 18, wherein the neoplasia condition is melanoma.

* * * * *

UNITED STATES PATENT AND TRADEMARK OFFICE
CERTIFICATE OF CORRECTION

PATENT NO. : 9,487,581 B2  Page 1 of 1
APPLICATION NO. : 11/817894
DATED : November 8, 2016
INVENTOR(S) : Abate et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1876 days.

Signed and Sealed this
Twenty-fifth Day of September, 2018

Andrei Iancu
*Director of the United States Patent and Trademark Office*

UNITED STATES PATENT AND TRADEMARK OFFICE

(12)     CERTIFICATE EXTENDING PATENT TERM
UNDER 35 U.S.C. § 156

| | | | |
|---|---|---|---|
| (68) | PATENT NO. | : | 9,487,581 |
| (45) | ISSUED | : | November 8, 2016 |
| (75) | INVENTOR | : | Abate et al. |
| (73) | PATENT OWNER | : | Pfizer Inc. |
| (95) | PRODUCT | : | IMJUDO® (tremelimumab-actl) |

This is to certify that an application under 35 U.S.C. § 156 has been filed in the United States Patent and Trademark Office, requesting extension of the term of U.S. Patent No. 9,487,581 based upon the regulatory review of the product IMJUDO® (tremelimumab-actl) by the Food and Drug Administration. According to United States Patent and Trademark Office records, the original expiration date of the patent as of the date of issuance of this certificate is April 21, 2031. Because it appears that the requirements of the law have been met, this certificate extends the term of the patent for the period of

(94)                                             1,208 days subject to the payment of maintenance fees as provided by law, with all rights pertaining thereto as provided by 35 U.S.C. § 156.

I have caused the seal of the United States Patent and Trademark Office to be affixed this 6th day of August 2025.

Coke Morgan Stewart
Acting Under Secretary of Commerce for Intellectual Property and Acting Director of the United States Patent and Trademark Office